(12) United States Patent
Kameda et al.

(10) Patent No.: US 12,285,600 B2
(45) Date of Patent: Apr. 29, 2025

(54) RESISTANCE DEVICE, INTEGRATED CIRCUIT DEVICE, IMPLANTABLE DEVICE, AND CORRECTION FACTOR DETERMINING METHOD

(71) Applicant: OSAKA UNIVERSITY, Osaka (JP)

(72) Inventors: Seiji Kameda, Suita (JP); Masayuki Hirata, Suita (JP)

(73) Assignee: OSAKA UNIVERSITY, Osaka (JP)

( * ) Notice: Subject to any disclaimer, the term of this patent is extended or adjusted under 35 U.S.C. 154(b) by 557 days.

(21) Appl. No.: 17/757,966

(22) PCT Filed: Dec. 18, 2020

(86) PCT No.: PCT/JP2020/047455
§ 371 (c)(1),
(2) Date: Jun. 24, 2022

(87) PCT Pub. No.: WO2021/132084
PCT Pub. Date: Jul. 1, 2021

(65) Prior Publication Data
US 2023/0032783 A1 Feb. 2, 2023

(30) Foreign Application Priority Data

Dec. 26, 2019 (JP) ................. 2019-236730

(51) Int. Cl.
*H03F 1/30* (2006.01)
*A61N 1/02* (2006.01)
(Continued)

(52) U.S. Cl.
CPC ............. *A61N 1/025* (2013.01); *A61N 1/08* (2013.01); *G01K 7/00* (2013.01); *G05F 1/567* (2013.01);
(Continued)

(58) Field of Classification Search
CPC . A61N 1/025; A61N 1/08; G01K 7/00; G05F 1/567; H03K 17/08104;
(Continued)

(56) References Cited

U.S. PATENT DOCUMENTS 8,659,358 B2 * 2/2014 Masuda ............... H03G 3/3042
330/285
10,187,041 B2 1/2019 Ida et al.
(Continued)

FOREIGN PATENT DOCUMENTS

JP 2011-254408 A 12/2011
JP 2015-122635 A 7/2015
(Continued)

OTHER PUBLICATIONS

Asai, Shin'ichi et al, "High-resistance device consisting of subthreshold-operated CMOS differential pair", Institute of Electrical Engineers of Japan-Electronic Circuit Study Group, (Miyazaki), Oct. 2009, <http://lalsie.ist.hokudai.ac.jp/graduates/index.php?id=s_asai>.
(Continued)

*Primary Examiner* — Hieu P Nguyen
(74) *Attorney, Agent, or Firm* — Studebaker Brackett PLLC

(57) ABSTRACT

A resistance device (100) includes a field-effect transistor (TN) and a voltage applying circuit (1). The voltage applying circuit (1) applies a control voltage (Vgs) between the gate and source of the field-effect transistor (TN) according to a temperature (T) to control a resistance value (R) between the drain and source of the field-effect transistor (TN). The control voltage (Vgs) is a voltage obtained by adding a correction voltage (Vc) to a reference voltage (Vgs0). The correction voltage (Vc) depends on the temperature (T) and is set to be zero at a first temperature (T1).

14 Claims, 33 Drawing Sheets

(51) Int. Cl.
   *A61N 1/08* (2006.01)
   *G01K 7/00* (2006.01)
   *G05F 1/567* (2006.01)
   *H03G 3/10* (2006.01)
   *H03K 17/081* (2006.01)
   *H03K 17/08* (2006.01)

(52) U.S. Cl.
   CPC .............. *H03K 17/08104* (2013.01); *H03K 2017/0806* (2013.01)

(58) Field of Classification Search
   CPC .. H03K 2017/0806; H03F 2203/45526; H03F 2203/45544; H03F 3/45475
   USPC .................................. 330/285, 296, 289, 277
   See application file for complete search history.

(56) References Cited

U.S. PATENT DOCUMENTS

| | | | |
|---|---|---|---|
| 10,620,702 | B2 | 4/2020 | Imajo et al. |
| 2018/0115303 | A1 | 4/2018 | Ida et al. |
| 2018/0120937 | A1 | 5/2018 | Imajo et al. |
| 2020/0054284 | A1 | 2/2020 | Imajo et al. |

FOREIGN PATENT DOCUMENTS

| | | |
|---|---|---|
| JP | 2017-534171 A | 11/2017 |
| JP | 2018-068886 A | 5/2018 |
| WO | 2016/064380 A1 | 4/2016 |
| WO | 2018/147407 A1 | 8/2018 |

OTHER PUBLICATIONS

Wada, Yusuke "Study of Current Reference using Temperature Dependence of Resistor under Low-power Supply Voltage", Graduate School of Science and Engineering vol. 37, published on Jul. 1, 2007, <https://chuo-u.repo.nii.ac.jp/?action=pages_view_main&active_action=repository_view_main_item_detail&item_id=4572&item_no=1&page_id=13&block_id=21>.

International Search Report issued in PCT/JP2020/047455; mailed Mar. 23, 2021.

\* cited by examiner

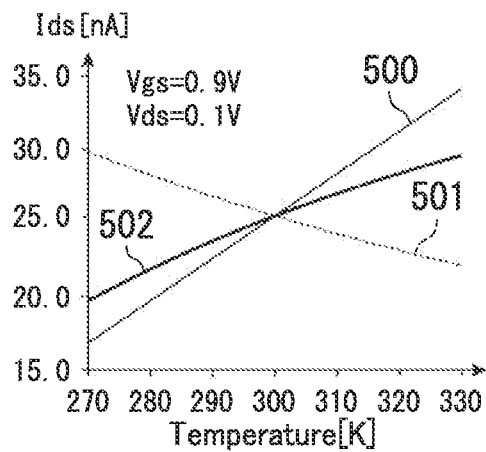
FIG. 5
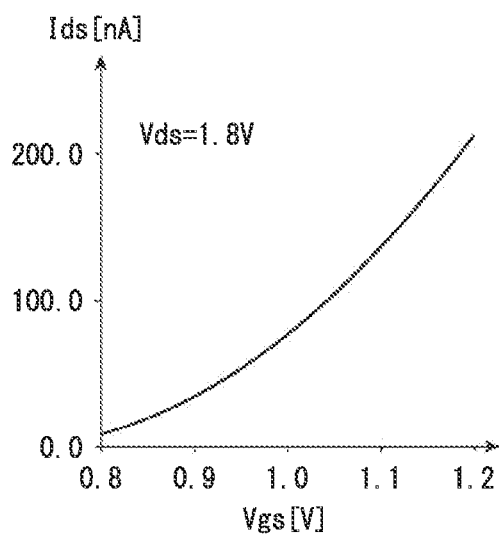
FIG. 6A
FIG. 6B

RESISTANCE DEVICE, INTEGRATED CIRCUIT DEVICE, IMPLANTABLE DEVICE, AND CORRECTION FACTOR DETERMINING METHOD

TECHNICAL FIELD

The present invention relates to a resistance device, an integrated circuit device, an implantable device, and a correction factor determining method.

BACKGROUND ART

An amplifier circuit described in Patent Literature 1 includes a field-effect transistor as a feedback resistor and a resistance correction section. The resistance correction section corrects the fluctuation in drain-source resistance of the field-effect transistor due to change in temperature.

That is, when the gate-source voltage Vgs of the field-effect transistor is constant, the drain-source resistance Rds decreases as the temperature thereof increases due to change in a threshold voltage Vth. On the other hand, as the temperature decreases, the drain-source resistance Rds increases. The resistance correction section therefore applies a gate voltage Vg equal to or lower than the threshold voltage Vth to the gate terminal of the field-effect transistor so that the difference (Vgs−Vth) between the voltage Vgs and the threshold voltage Vth becomes a constant value, thereby controlling the drain-source resistance Rds of the field-effect transistor to a predetermined value.

Specifically, the resistance correction section includes a temperature detector. The temperature detector outputs a voltage or current that varies linearly according to change in temperature. The resistance correction section applies a gate voltage Vg equal to or lower than the threshold voltage to the gate terminal of the field-effect transistor based on the current or voltage output from the temperature detector so that the drain-source resistance Rds of the field-effect transistor becomes the predetermined value.

More specifically, the resistance correction section further includes storage and an operation part. The storage stores the relationship between the current or voltage output from the temperature detector and the temperature of the temperature detector. The storage also stores the relationship between the temperature of the temperature detector and the gate voltage Vg applied to the gate terminal of the field-effect transistor.

The relationship between the current or voltage output from the temperature detector and the temperature of the temperature detector is stored in the storage by measuring the relationship between the temperature and the current or voltage output from the temperature detector in advance. The relationship between the temperature of the temperature detector and the gate voltage Vg applied to the gate terminal of the field-effect transistor is stored in the storage by determining, for each temperature, the gate voltage Vg at which the difference (Vgs−Vth) between the gate-source voltage Vgs of the field-effect transistor and the threshold voltage Vth becomes a constant value.

The operation part refers to the relationship between the current or voltage from the temperature detector stored in the storage and the temperature of the temperature detector, and finds the temperature of the temperature detector based on the current or voltage from the temperature detector. The operation part also refers to the relationship between the gate voltage Vg applied to the gate terminal of the field-effect transistor and the temperature of the temperature detector stored in the storage, and determines a gate voltage Vg to be applied to the gate terminal of the field-effect transistor based on the found temperature.

CITATION LIST

Patent Literature

Patent Literature 1: JP 2015-122635 A

SUMMARY OF INVENTION

Technical Problem

However, Patent Literature 1 does not describe any method for determining the gate voltage Vg at which the difference (Vgs−Vth) between the threshold voltage Vth and the voltage Vgs of the field-effect transistor becomes a constant value at a plurality of different temperatures.

In other words, Patent Literature 1 describes no method for determining the correction value by which the gate voltage Vg is corrected so that the resistance Rds becomes the predetermined value by reducing temperature dependence of the drain-source resistance Rds (an example of a physical quantity relating to the field-effect transistor) of the field-effect transistor.

An object of the present invention is to provide a resistance device, an integrated circuit device, an implantable device, and a correction factor determining method, which enable efficient determination of a combination of: a correction factor for correcting a control voltage across a gate and a source of a field-effect transistor to reduce temperature dependence of a desired physical quantity relating to the field-effect transistor; and the desired physical quantity relating to the field-effect transistor.

Solution to Problem

A resistance device according to an aspect of the present invention includes a field-effect transistor and a voltage applying circuit. The voltage applying circuit applies a control voltage according to a temperature between a gate and a source of the field-effect transistor to control a resistance value between a drain and the source of the field-effect transistor. The control voltage is a voltage obtained by adding a correction voltage to a reference voltage. The correction voltage depends on the temperature and is set to be zero at a first temperature.

In the resistance device according to the aspect of the present invention, preferably the voltage applying circuit includes a temperature detector and a control voltage applying section. Preferably the temperature detector outputs a detection signal according to the temperature. It is preferable that the control voltage applying section generates the control voltage so that the control voltage includes the correction voltage that varies linearly with respect to the temperature according to the detection signal and then applies the control voltage between the gate and the source of the field-effect transistor.

In the resistance device according to the aspect of the present invention, preferably the first temperature is a temperature when a physical quantity relating to the field-effect transistor is substantially constant with respect to change in a correction factor that is a factor for determining the correction voltage.

In the resistance device according to the aspect of the present invention, preferably a value of the correction factor that is a value for determining the correction voltage is a value when a target physical quantity relating to the field-effect transistor is obtained at a second temperature different from the first temperature based on the reference voltage when the target physical quantity is obtained at the first temperature.

In the resistance device according to the aspect of the present invention, preferably the temperature detector includes a first current source circuit that generates a first current and a second current source circuit that generates a second current. Preferably temperature dependence of the first current source circuit differs from temperature dependence of the second current source circuit. Preferably the first current source circuit is connected in series to the second current source circuit. Preferably a difference current between the first current and the second current is the detection signal. Preferably the first temperature is varied by the first current source circuit varying a current value of the first current and/or the second current source circuit varying a current value of the second current.

In the resistance device according to the aspect of the present invention, preferably the voltage applying circuit applies the control voltage between the gate and the source of the field-effect transistor to control a resistance value between the drain and the source, in a first operating region, of the field-effect transistor. Preferably the first operating region is a region in which a magnitude of a voltage between the gate and the source of the field-effect transistor is larger than a magnitude of a threshold voltage.

In the resistance device according to the aspect of the present invention, preferably the voltage applying circuit applies the control voltage between the gate and the source of the field-effect transistor to control a resistance value between the drain and the source, in a second operating region, of the field-effect transistor. Preferably the second operating region is a region in which a magnitude of a voltage between the gate and the source of the field-effect transistor is smaller than a magnitude of the threshold voltage.

An integrated circuit device according to another aspect of the present invention integrates the field-effect transistor and the voltage applying circuit of the resistance device.

An implantable device according to still another aspect of the present invention is allowed to be placed into a part of a body. The implantable device includes at least one of devices that include a stimulating device that gives a stimulation signal to living tissue and a measuring device that measures a biological signal. The at least one of the devices includes the integrated circuit device.

A correction factor determining method according to yet another aspect of the present invention determines a correction factor for correcting a control voltage to be applied between a gate and a source of a field-effect transistor. The correction factor determining method, in which the control voltage is represented by "Vgs" in an equation below $$Vgs=Vgs0+Vc=Vgs0+\beta(T-T1),$$

where "Vgs0" represents a reference voltage, "Vc" represents a correction voltage, "β" represents a correction factor, "T" represents a temperature as a variable, and "T1" represents a first temperature that is a temperature when the correction voltage Vc becomes zero, comprises: determining a specific voltage value that is a voltage value of the reference voltage Vgs0 when a target physical quantity relating to the field-effect transistor is obtained at the first temperature T1; and determining a specific factor value that is a value of the correction factor β when the target physical quantity is obtained at a second temperature different from the first temperature T1 and the specific voltage value of the reference voltage Vgs0.

In the correction factor determining method according to the aspect of the present invention, preferably the determining a specific voltage value that is a voltage value of the reference voltage Vgs0 includes: measuring a physical quantity relating to the field-effect transistor while varying a voltage value of the reference voltage Vgs0 at the first temperature T1; and defining, as the specific voltage value of the reference voltage Vgs0, the voltage value of the reference voltage Vgs0 when of a plurality of physical quantities measured while varying the voltage value of the reference voltage Vgs0, a physical quantity substantially matching the target physical quantity is measured. Preferably the determining a specific factor value that is a value of the correction factor β includes: measuring a physical quantity relating to the field-effect transistor while varying a value of the correction factor β at the second temperature and the specific voltage value of the reference voltage Vgs0; and defining, as the specific factor value of the correction factor β, the value of the correction factor β when of a plurality of physical quantities measured while varying the value of the correction factor β, a physical quantity substantially matching the target physical quantity is measured.

In the correction factor determining method according to the aspect of the present invention, preferably the first temperature T1 is a temperature when a physical quantity relating to the field-effect transistor is substantially constant with respect to change in the correction factor β.

In the correction factor determining method according to the aspect of the present invention, preferably the correction voltage Vc has a value based on a difference current between a first current and a second current. Preferably the first current is a current that varies linearly with respect to change in temperature. Preferably the second current is a current that varies linearly with respect to the change in the temperature. Preferably temperature dependence of the first current differs from temperature dependence of the second current. Preferably the correction factor determining method further comprises varying the first temperature T1 by varying at least one of current values that include a current value of the first current and a current value of the second current.

In the correction factor determining method according to the aspect of the present invention, preferably the target physical quantity is a physical quantity containing a resistance value of the field-effect transistor. The physical quantity is measurable from an electronic circuit including the field-effect transistor. The target physical quantity is to be set as a target value.

Advantageous Effects of Invention

The present invention makes it possible to provide the resistance device, the integrated circuit device, the implantable device, and the correction factor determining method, which enable efficient determination of a combination of: a correction factor for correcting the control voltage across the gate and the source of the field-effect transistor to reduce temperature dependence of a desired physical quantity relating to the field-effect transistor; and the desired physical quantity relating to the field-effect transistor.

BRIEF DESCRIPTION OF DRAWINGS

FIG. 5 is a graph illustrating temperature dependence of drain current of a general NMOS transistor in the linear region at Vgs>Vth.

FIG. 6A is a graph illustrating Ids-Vgs characteristics of a general NMOS transistor in the saturation region at Vgs>Vth. FIG. 6B is a graph illustrating temperature dependence of drain current of the general NMOS transistor in the saturation region at Vgs>Vth.

DESCRIPTION OF EMBODIMENTS

Figure 1:
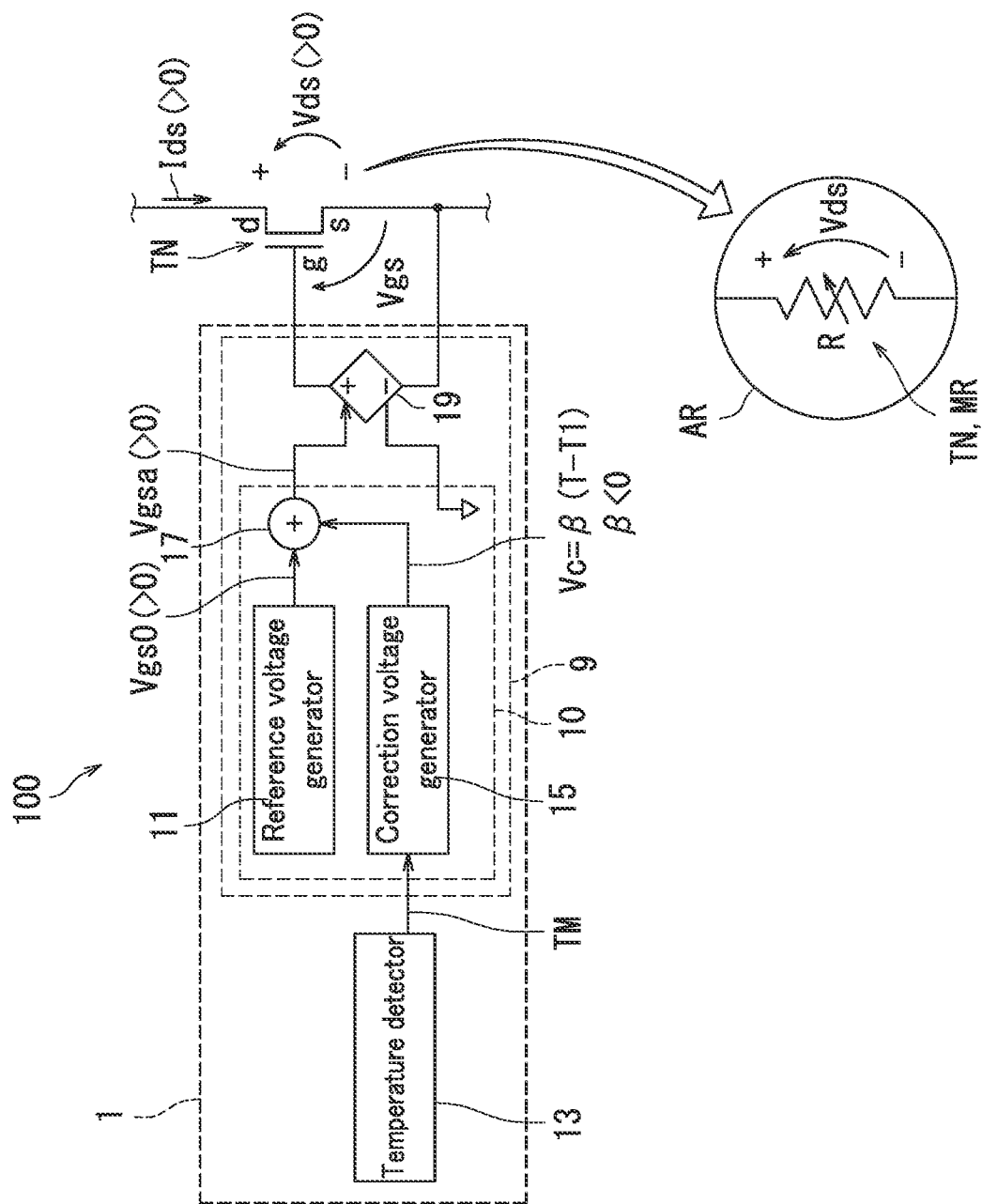
FIG. 1 is a diagram illustrating a resistance device according to a first embodiment of the present invention.

Hereinafter, embodiments of the present invention will be described with reference to the drawings. Note that elements which are the same or equivalent are labelled the same reference signs in the drawings and description thereof is not repeated. The reference sign attached to an electric current may be used as a sign representing a "current value" of the current. The reference sign attached to a voltage may be used as a sign representing a "voltage value" of the voltage. The reference sign attached to a resistor or a resistance element may be used as a sign representing a "resistance value" of the resistor or the resistance element. Further, the same symbol in a plurality of equations has the same definition, and therefore the description of the same symbol will be omitted as appropriate. Note that gate, drain, and source terminals in the drawings may be denoted by "g", "d", and "s" for ease of understanding, respectively.

First Embodiment

A resistance device 100 according to a first embodiment of the present invention will be described with reference to FIGS. 1 to 23B.

FIG. 1 is a diagram illustrating the resistance device 100 according to the first embodiment. As illustrate in FIG. 1, the resistance device 100 includes a field-effect transistor TN and a voltage applying circuit 1. In the first embodiment, the field-effect transistor TN is an n-type field-effect transistor as illustrated in FIG. 1. Specifically, the field-effect transistor TN is an n-type metal-oxide-semiconductor field-effect transistor (n-type MOSFET), namely an NMOS transistor.

Hereinafter, the field-effect transistor TN may be referred to as a "transistor TN".

Note that a back-gate terminal of the field-effect transistor TN may be connected to a source or drain terminal of the field-effect transistor TN, or a ground or an earth.

The field-effect transistor TN functions as a resistance element. Specifically, the field-effect transistor TN functions as the resistance element by resistance between the drain and source of the field-effect transistor TN. That is, the field-effect transistor TN functions as MOS resistance. Field-effect transistors functioning as MOS resistance are described in, for example, "C. A. Mead, "Analog VLSI and Neural Systems", Addison-Wesley Publishing Company, 1989." or "T. Delbruck and C. A. Mead, "Adaptive photoreceptor with wide dynamic range", Proceedings of IEEE International Symposium on Circuits and Systems, 1994."

Specifically, the field-effect transistor TN functions as a resistance element by resistance between the drain and source in a region (linear and saturation regions) where a gate-source voltage of the field-effect transistor TN is larger than a threshold voltage thereof. The field-effect transistor TN also functions as a resistance element by resistance between the drain and source in a region (subthreshold region) where the gate-source voltage of the field-effect transistor TN is smaller than the threshold voltage.

An equivalent circuit whose field-effect transistor TN functions as MOS resistance MR is illustrated in the region AR in FIG. 1. The MOS resistance MR has a resistance value R corresponding to a resistance value between the drain and source of the field-effect transistor TN. When a voltage Vds corresponding to the drain-source voltage of the field-effect transistor TN is applied across the MOS resistance MR, a current Ids corresponding to a drain current flowing between the drain and source of the field-effect transistor TN flows through the MOS resistance MR.

Hereinafter, the resistance value R between the drain and source of the field-effect transistor TN may be described as a "resistance value R of the field-effect transistor TN".

The voltage applying circuit 1 applies a control voltage Vgs according to a temperature T between the gate and source of the field-effect transistor TN to control the resistance value R between the drain and source of the field-effect transistor TN. The "between the gate and source of the field-effect transistor TN" means "between the gate and source terminals of the field-effect transistor TN". The temperature T corresponds to the ambient temperature of the resistance device 100. The control voltage Vgs has a positive value. The control voltage Vgs corresponds to a voltage between the gate and source of the field-effect transistor TN.

Hereinafter, the control voltage Vgs may be described as a "gate-source voltage Vgs". Further, the voltage Vds between the drain and source may be described as a "drain-source voltage Vds".

The control voltage Vgs is a voltage obtained by adding a correction voltage Vc to a reference voltage Vgs0. Specifically, the control voltage Vgs is expressed as Equation (1).

$$Vgs = Vgs0 + Vc \qquad \text{Equation (1):}$$

The correction voltage Vc is a voltage to be added to the reference voltage Vgs0 in order to reduce temperature dependence of a desired physical quantity relating to the field-effect transistor TN.

The physical quantity relating to the field-effect transistor TN is a physical quantity containing the resistance value R of the field-effect transistor TN, which is measurable from an electronic circuit including the field-effect transistor TN. The physical quantity relating to the field-effect transistor TN is, for example, the resistance value R between the drain and source of the field-effect transistor TN, or a cutoff frequency fc of a filter circuit including the field-effect transistor TN. The "physical quantity containing the resistance value R" is a physical quantity depending on the resistance value R. Hereinafter, a desired physical quantity relating to the field-effect transistor TN may be described as a "target physical quantity". The target physical quantity is therefore a physical quantity containing the resistance value R of the field-effect transistor TN, which is measurable from the electronic circuit including the field-effect transistor TN. The target physical quantity is a physical quantity that is set as a target value.

Specifically, the correction voltage Vc is expressed as Equation (2), where β denotes a correction factor, T denotes a temperature, and T1 denotes a first temperature. The correction factor β is a factor for determining the correction voltage Vc. In the first embodiment, the correction factor β has a negative value. The correction voltage Vc therefore becomes smaller as the temperature T becomes higher. Specifically, the correction factor β is a factor for correcting the control voltage Vgs to be applied between the gate and source of the field-effect transistor TN in order to reduce the temperature dependence of a desired physical quantity relating to the field-effect transistor TN.

$$Vc=\beta(T-T1) \quad \text{Equation (2):}$$

The correction voltage Vc depends on the temperature T and is set to be zero at the first temperature T1 as in Equation (2). In other words, the first temperature T1 is the temperature at which the correction voltage Vc becomes zero. The correction effect is therefore lost at the first temperature T1 in the first embodiment. Using the voltage applying circuit 1 such that the correction effect disappears at the first temperature T1 enables efficient determination of a combination of the correction factor β for correcting the control voltage Vgs to be applied between the gate and source of the field-effect transistor TN and a desired physical quantity relating to the field-effect transistor TN. The details will be described later.

Figure 2:
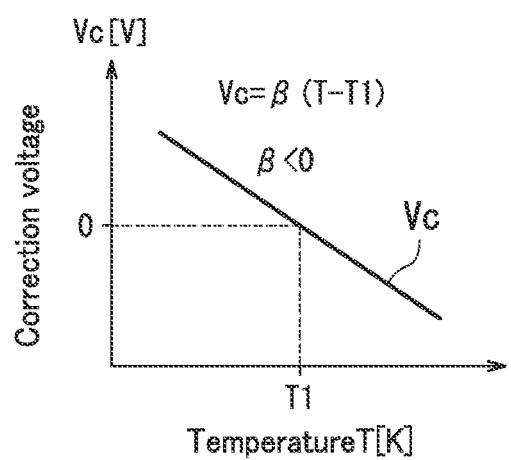
FIG. 2 is a graph illustrating temperature dependence of correction voltage generated inside a voltage applying circuit in the first embodiment.

FIG. 2 is a graph illustrating correction voltage Vc. Correction voltage Vc [V] is on the vertical axis, and temperature T [K] is on the horizontal axis. The correction voltage Vc varies linearly with respect to the temperature T as illustrated in FIG. 2. The slope of the straight line corresponding to the correction voltage Vc is denoted by the correction factor β.

Following describes, with reference to FIGS. 3 to 6, the reason why the temperature dependence of the field-effect transistor TN as the MOS resistance MR can be corrected by adding a correction voltage Vc varying linearly according to the temperature T in Equation (2) to the reference voltage Vgs0 like the control voltage Vgs expressed as Equation (1). In this case, in order to facilitate understanding, attention is paid to the resistance value R between the drain and source of the NMOS transistor in a "Vgs>Vth" region thereof. The "Vgs>Vth" region is an operating region of the NMOS transistor when the magnitude of the gate-source voltage Vgs (voltage between the gate and source) is larger than the magnitude of the threshold voltage Vth. The "Vgs>Vth" region corresponds to an example of a "first operating region of the field-effect transistor".

Figure 3A:
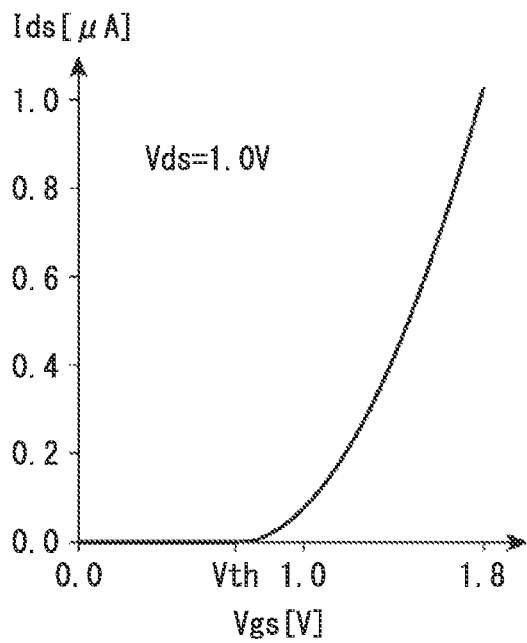
FIG. 3A is a graph illustrating Ids-Vgs characteristics of a general NMOS transistor in the saturation region at Vgs>Vth.

FIG. 3A is a graph illustrating Ids-Vgs characteristics of a general NMOS transistor in a saturation region of the "Vgs>Vth" region. Gate-source voltage Vgs [V] is on the horizontal axis, and drain current Ids [pA] is on the vertical axis.

Figure 3B:
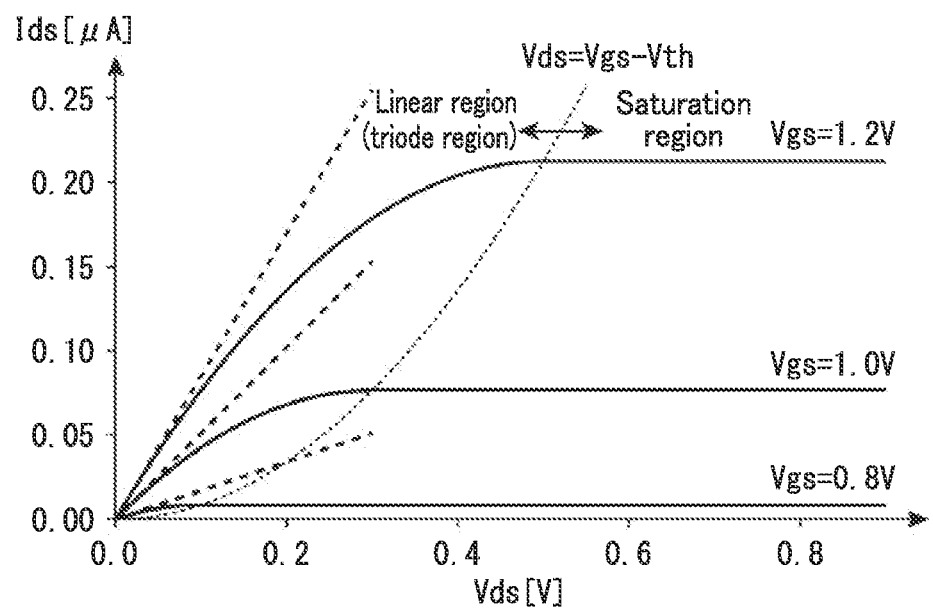
FIG. 3B is a graph illustrating Ids–Vds characteristics of the general NMOS transistor at Vgs>Vth.

FIG. 3B is a graph illustrating Ids–Vds characteristics of the general NMOS transistor. Drain-source voltage Vds [V] is on the horizontal axis, and drain current Ids [µA] is on the vertical axis. FIG. 3B illustrates respective drain currents Ids at Vgs=0.8V, 1.0V, and 1.2V.

Of the "Vgs>Vth" region, a region of "Vds>Vgs−Vth" is the saturation region of the NMOS transistor. The drain current Ids in the saturation region is expressed as Equation (3), where Cox denotes gate capacitance of the NMOS transistor, µn denotes electron mobility of the NMOS transistor, L denotes a gate length of the NMOS transistor, and W denotes a gate width of the NMOS transistor.

The simulation results using standard circuit parameters according to Equation (3) are illustrated in the "saturation region" of FIGS. 3A and 3B. As illustrated in FIG. 3A, when the gate-source voltage Vgs is larger than the threshold voltage Vth, the drain current Ids flows. As illustrated in FIG. 3B, the drain current Ids is saturated at a substantially constant value in the saturation region. That is, the drain current Ids does not depend on the drain-source voltage Vds in the saturation region. The region basically used in the NMOS transistor is the saturation region.

[Math. 1]

$$I_{ds} = \frac{1}{2}\mu_n C_{ox} \frac{W}{L}(V_{gs} - V_{th})^2 \quad \text{Equation (3)}$$

On the other hand, a region of "Vds<Vgs−Vth" of the "Vgs>Vth" region is a linear region of the NMOS transistor. The drain current Ids in the linear region is expressed as Equation (4). The simulation results using standard circuit parameters according to Equation (4) are illustrated in the "linear region" in FIG. 3B. In the "linear region", the drain current Ids varies linearly with respect to the drain-source voltage Vds as illustrated in FIG. 3B.

[Math. 2]

$$I_{ds} = \mu_n C_{ox} \frac{W}{L}\left[(V_{gs} - V_{th})V_{ds} - \frac{1}{2}V_{ds}^2\right] \quad \text{Equation (4)}$$

That is, in the linear region, the Ids–Vds characteristics can be linearly approximated, and therefore the NMOS transistor can be easily used as the MOS resistance as a preferable example. Specifically, from the tangent equation based on Equation (4) at Vds=0, the drain current Ids can be linearly approximated according to Equation (5).

[Math. 3]

$$I_{ds} = \frac{\partial I_{ds}}{\partial V_{ds}} V_{ds} = \mu_n C_{ox} \frac{W}{L}(V_{gs} - V_{th})V_{ds} \quad \text{Equation (5)}$$

As can be seen from Equation (5), the gate-source voltage Vgs enables control of the drain current Ids. The Vgs enabling control of the drain current Ids is synonymous with Vgs enabling control of the resistance value R of the NMOS transistor because of R=Vds/Ids. The straight lines depicted by the broken lines in FIG. 3B illustrate simulation results using standard circuit parameters according to Equation (5) at Vgs=0.8V, 1.0V, and 1.2V. The smaller Vgs, the smaller the slope of the straight line depicted by each broken line. That is, the smaller the Vgs, the higher the resistance value R.

Figure 4A:
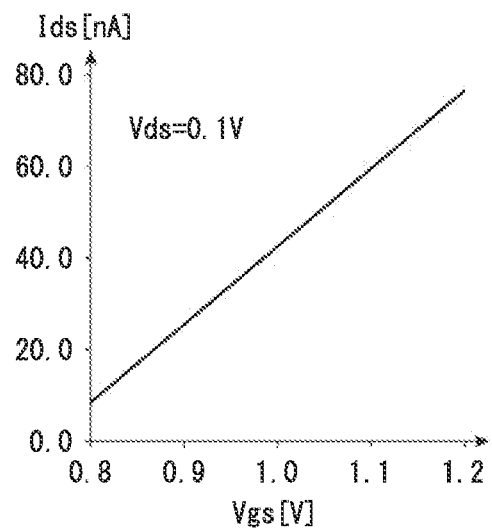
FIG. 4A is a graph illustrating Ids-Vgs characteristics of a general NMOS transistor in the linear region at Vgs>Vth.
Figure 4B:
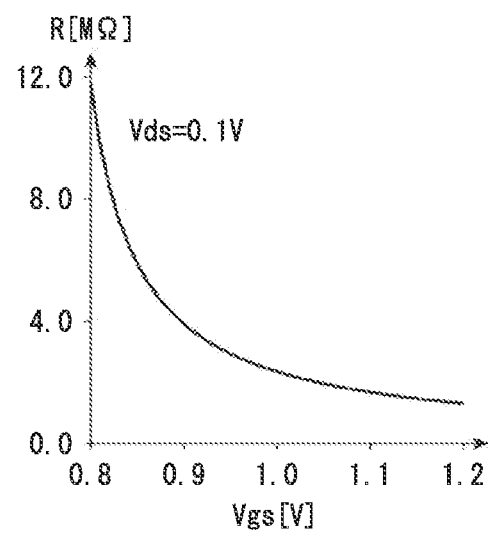
FIG. 4B is a graph illustrating the relationship between Vgs and resistance value of the general NMOS transistor in the linear region at Vgs>Vth.

FIGS. 4A and 4B therefore illustrate how the gate-source voltage Vgs [V] has relationships with the drain current Ids [nA] and the resistance value R [MΩ]. FIGS. 4A and 4B illustrate simulation results using standard circuit parameters based on Equation (4).

In an example illustrated in FIG. 4A, the drain current Ids increases linearly with the gate-source voltage Vgs increasing in the range of several hundred mV. That is, the drain current Ids is proportional to the gate-source voltage Vgs in the range of several hundred mV.

The resistance value R of the NMOS transistor as the MOS resistance can be expressed as Equation (6), and is therefore inversely proportional to the gate-source voltage Vgs as illustrated in FIG. 4B.

$$R = Vds/Ids \qquad \text{Equation (6):}$$

Note that the conditions for the simulation using the standard circuit parameters in FIGS. 3A to 4B are μn·Cox=170.0 μA/V², W=0.6 μm, L=60.0 μm, αth=−1.7 mV/K, αμ=−1.5, Vth=0.7V, T0=300K, and C=800.0 fF.

As described above with reference to FIGS. 3A to 4B, the MOS resistance of the NMOS transistor can be used as linear resistance in the linear region of the "Vgs>Vth" region. For example, the current flowing through the MOS resistance is proportional to the gate-source voltage Vgs, and the cutoff frequency fc of the RC filter composed of the MOS resistance is proportional to the gate-source voltage Vgs. That is, Vgs enables liner control of the current flowing through the MOS resistance and the cutoff frequency fc of the RC filter.

Each of the electron mobility μn and the threshold voltage Vth of the NMOS transistor however has temperature dependence. The threshold voltage Vth considering the temperature dependence is expressed as Equation (7), where uth denotes a temperature coefficient of the threshold voltage Vth and Vth_T0 denotes the threshold voltage Vth at a temperature T0. That is, the threshold voltage Vth varies from Vth_T0 according to change from T0 in temperature with the threshold voltage Vth_T0 obtained as an observed value at an arbitrary temperature T0 being as a boundary, as in Equation (7).

[Math. 4]

$$Vth = V_{th\_}T_0 + \alpha_{th}(T - T_0) \qquad \text{Equation (7):}$$

The electron mobility μn considering the temperature dependence is expressed as Equation (8), where up denotes a temperature coefficient of the electron mobility μn and μn_T0 denotes electron mobility μn at the temperature T0. That is, the electron mobility μn varies from μn_T0 according to change from T0 in temperature with the electron mobility obtained as an observed value at an arbitrary temperature T0 being as a boundary, as in Equation (8).

[Math. 5]

$$\mu_n = \mu_{n\_}T_0 \cdot (T/T_0)^{\alpha_\mu} \qquad \text{Equation (8):}$$

Equation (9) expresses the drain current Ids reflecting both temperature dependence of the threshold voltage Vth and temperature dependence of the electron mobility μn of the NMOS transistor in the linear region based on Equations (4), (7), and (8).

[Math. 6]

$$I_{ds} = \mu_{n\_}T_0 \cdot (T/T_0)^{\alpha_\mu} \cdot C_{ox}\frac{W}{L}\left[(V_{gs} - V_{th\_}T_0 - \alpha_{th}(T - T_0))V_{ds} - \frac{1}{2}V_{ds}^2\right] \qquad \text{Equation (9)}$$

FIG. 5 is a graph illustrating the temperature dependence of the drain current Ids of a general NMOS transistor in the linear region of the "Vgs>Vth" region. Temperature [K] is on the horizontal axis, and drain current Ids [nA] is on the vertical axis. In FIG. 5, Line 500 represents the drain current Ids where only the temperature dependence of the threshold voltage Vth is reflected with αμ=0 in Equation (9). Line 501 represents the drain current Ids where only the temperature dependence of the electron mobility μn is reflected with αth=0 in Equation (9). Line 502 represents the drain current Ids, according to Equation (9), where both the temperature dependence of the electron mobility μn and the temperature dependence of the threshold voltage Vth are reflected.

The temperature coefficient uth of the threshold voltage Vth in Equations (7) and (9) takes a negative value. The drain current Ids therefore increases linearly with rising temperature as in Line 500 of FIG. 5, when considering only the temperature dependence of the threshold voltage Vth because the threshold voltage Vth qualitatively decreases as the number of movable charged particles increases with rising temperature.

Further, the temperature coefficient up of the electron mobility μn in Equations (8) and (9) takes a negative value. The drain current Ids decreases substantially linearly with rising temperature as in Line 501 of FIG. 5, when considering only the temperature dependence of the electron mobility μn because the movement of charged particles is qualitatively hindered by the thermal vibration of the silicon crystal lattice when temperature rises.

That is, as in Lines 500 and 501, it is possible to linearly approximate the drain current Ids reflecting the temperature dependence of the threshold voltage Vth and the drain current Ids reflecting the temperature dependence of the electron mobility μn.

It is therefore possible to linearly approximate the drain current Ids reflecting both the temperature dependence of the threshold voltage Vth and the temperature dependence of the electron mobility μn, as in Line 502.

Specifically, the drain current Ids increases substantially linearly with rising temperature as in Line 502 because the temperature dependence of the threshold voltage Vth has a greater effect on the drain current Ids than the temperature dependence of the electron mobility μn. In other words, the influence of the temperature dependence of the threshold voltage Vth is suppressed by the influence of the temperature dependence of the electron mobility μn.

In an example, the temperature coefficient uth of a standard threshold voltage Vth is −1.7 mV/K, and therefore the temperature rise of 50 degrees lowers the threshold voltage Vth by 85 mV. Further, the decrease width (85 mV) of the threshold voltage Vth is narrowed (less than 85 mV) by the suppression effect due to the temperature dependence of the electron mobility μn.

On the other hand, as an example, the amount of increase in the drain current Ids when the gate-source voltage Vgs is increased by 100 mV can be linearly approximated as illustrated in FIG. 4A.

The temperature dependence of the drain current Ids can therefore be suppressed by linearly decreasing the gate-source voltage Vgs in response to the drain current Ids (Line 502 in FIG. 5) increasing linearly with rising temperature to linearly decrease the drain current Ids. This enables correction to the temperature dependence of the NMOS transistor as the MOS resistance in the linear region of the "Vgs>Vth" region.

It can be seen from the above that the temperature dependence of the transistor TN as the MOS resistance MR can be corrected by adding the correction voltage Vc varying linearly according to temperature T in Equation (2) to the reference voltage Vgs0, like the control voltage Vgs, in Equation (1), to be applied between the gate-source of the transistor TN in the linear region of the "Vgs>Vth" region.

Similarly, the temperature dependence of the transistor TN as the MOS resistance can be corrected by adding the correction voltage Vc varying linearly according to the temperature T in Equation (2) to the reference voltage Vgs0 like the control voltage Vgs in Equation (1) even in the saturation region of the "Vgs>Vth" region of the transistor TN. The details will be described with reference to FIGS. 6A and 6B.

FIG. 6A is a graph illustrating the drain current Ids with respect to the gate-source voltage Vgs of a general NMOS transistor according to Equation (3) in the saturation region of the "Vgs>Vth" region. Although the drain current Ids has a non-linearity as compared with the linear region in FIG. 4A, it can be linearly approximated in the range of about 100 mV as illustrated in FIG. 6A.

On the other hand, Equation (10) expresses the drain current Ids, in the saturation region, of the NMOS transistor reflecting the temperature dependence based on Equations (3), (7), and (8).

[Math. 7]

$$I_{ds} = \frac{1}{2}\mu_{n\_} T_0 \cdot (T/T_0)^{\alpha\mu} \cdot C_{ox}\frac{W}{L}(V_{gs} - V_{th\_}T_0 - \alpha_{th}(T - T_0))^2$$

Equation (10)

FIG. 6B is a graph illustrating the temperature dependence of the drain current Ids of the general NMOS transistor in the saturation region of the "Vgs>Vth" region. Temperature [K] is on the horizontal axis, and drain current Ids [nA] is on the vertical axis. In FIG. 6B, Line 503 represents the drain current Ids where only the temperature dependence of the threshold voltage Vth is reflected as αμ=0 in Equation (10). Line 504 represents the drain current Ids where only the temperature dependence of the electron mobility μn is reflected as αth=0 in Equation (10). Line 505 represents the drain current Ids, according to Equation (10), where both the temperature dependence of the electron mobility μn and the temperature dependence of the threshold voltage Vth are reflected.

As in line 505, the drain current Ids reflecting both the temperature dependence of the threshold voltage Vth and the temperature dependence of the electron mobility μn can also be linearly approximated even in the saturation region of the "Vgs>Vth" region like in the linear region. In an example, the temperature coefficient αth of the standard threshold voltage Vth is −1.7 mV/K, and a suppression effect is obtained due to the temperature dependence of the electron mobility μn. Accordingly, the decrease in the threshold voltage Vth with the temperature rise of 50 degrees is less than 85 mV even in the saturation region like the linear region. On the other hand, as an example, the amount of increase in drain current Ids when the gate-source voltage Vgs is increased by 100 mV can be linearly approximated as illustrated in FIG. 6A.

The temperature dependence of the drain current Ids can therefore be suppressed by linearly decreasing the gate-source voltage Vgs in response to the drain current Ids (Line 505 in FIG. 6B) increasing linearly with rising temperature to linearly decrease the drain current Ids. This enables correction to the temperature dependence of the NMOS transistor as the MOS resistance in the saturation region of the "Vgs>Vth" region.

It can be seen from the above that the temperature dependence of the transistor TN as the MOS resistance MR can be corrected by adding the correction voltage Vc varying linearly according to the temperature T in Equation (2) to the reference voltage Vgs0 even in the saturation region of the "Vgs>Vth" region like the control voltage Vgs, in Equation (1), applied between the gate and source of the transistor TN.

Note that the conditions for simulation using the standard circuit parameters in FIGS. 5 to 6B are μn_T0·Cox=170.0 μA/V², W=0.6 μm, L=60.0 μm, αth=−1.7 mV/K., αμ=−1.5, Vth_T0=0.7V, T0=300K, and C=800.0 fF.

As described above with reference to FIGS. 3A to 6B, the temperature dependence of the transistor TN as the MOS resistance MR can be corrected by adding the correction voltage Vc varying linearly according to the temperature T in Equation (2) to the reference voltage Vgs0 in the "Vgs>Vth" region where the gate-source voltage Vgs is larger than the threshold voltage Vth regardless of the linear and saturation regions, like the control voltage Vgs, in Equation (1), applied between the gate and source of the transistor TN.

The voltage applying circuit 1 in FIG. 1 is one example of a circuit that corrects the temperature dependence of the MOS resistance MR composed of the transistor TN according to the method based on Equations (1) and (2). The details of the voltage applying circuit 1 will be described with reference to FIG. 1 again. The voltage applying circuit 1 is placed between the gate and source terminals of the transistor TN. The potential (hereinafter, may be referred to as "source potential Vs") at the source terminal can take any value. Specifically, the two terminals of the drain and source terminals of the transistor TN are used as two terminals, both ends, of the MOS resistance MR, and are therefore used in a state electrically independent of earth or ground (0 [V])(for example, in a floating state). The source potential Vs can consequently take any value.

The voltage applying circuit 1 includes a control voltage applying section 9 and a temperature detector 13. The temperature detector 13 detects a temperature T and outputs a detection signal TM corresponding to the temperature T to the control voltage applying section 9. The configuration of the temperature detector 13 is not particularly limited as long as the temperature detector 13 can detect the temperature T to output a detection signal TM containing a physical quantity (for example, current or voltage) representing the temperature T or to output a detection signal TM containing a physical quantity (for example, current or voltage) correlated with the temperature T. For example, the temperature detector 13 may include a temperature sensor such as a thermistor. For example, the temperature detector 13 may include a field-effect transistor or a bipolar transistor and utilize the temperature-dependent characteristics of the field-effect transistor or the bipolar transistor. For example, the temperature detector 13 may include a proportional to absolute temperature (PTAT) circuit. The PTAT circuit outputs a current proportional to the absolute temperature as the detection signal TM. For example, the temperature detector 13 is configured by a temperature detection circuit that detects the temperature T and outputs the detection signal TM.

The control voltage applying section 9 applies the control voltage Vgs according to the detection signal TM representing the temperature T between the gate and source of the transistor TN. Specifically, the control voltage applying section 9 generates the control voltage Vgs containing the correction voltage Vc varying linearly with respect to the temperature T according to the detection signal TM. The control voltage applying section 9 then applies the control voltage Vgs between the gate and source of the transistor TN. The first embodiment therefore enables appropriate reduction in the temperature dependence of the resistance value R of the transistor TN according to the detection signal TM representing the temperature T.

Specifically, the control voltage applying section 9 includes a control voltage generator 10 and a voltage-controlled voltage source 19. Further, the control voltage generator 10 includes a reference voltage generator 11, a correction voltage generator 15, and an addition section 17. The reference voltage generator 11 generates the reference voltage Vgs0 in Equation (1) and outputs the reference voltage Vgs0 to the addition section 17. Based on the detection signal TM representing temperature, the correction voltage generator 15 generates the correction voltage Vc varying linearly with respect to the temperature T, and outputs the correction voltage Vc to the addition section 17. The addition section 17 adds the reference voltage Vgs0 and the correction voltage Vc to generate a control voltage Vgsa as an addition result. In this way, the control voltage generator 10 generates the control voltage Vgsa. The control voltage Vgsa may be described as a "reference control voltage Vgsa". The control voltage Vgsa is expressed as Equation (11).

$$Vgsa = Vgs0 + Vc \qquad \text{Equation (11):}$$

As is clear from Equations (1) and (11), the control voltage Vgsa and the control voltage Vgs include the same voltage component (reference voltage Vgs0 and correction voltage Vc) and the same voltage value. Also in Equation (11), the correction voltage Vc is expressed as Equation (2). The correction voltage Vc in Equation (2) decreases linearly with the rising temperature T as illustrated in FIG. 2. That is, in the case of the transistor TN, the correction factor β takes a negative value. Changing the correction factor β enables adjustment to the ratio of lowering the control voltage Vgsa according to the temperature T.

Here, the control voltage Vgsa is specifically a voltage with a reference designated 0 [V] (that is, a potential difference with a reference designated 0 [V]). On the other hand, a source potential Vs of the transistor TN can take any value. Therefore, the control voltage Vgsa is applied directly between the gate and source, and then "Vgsa−Vs" becomes a voltage between the gate and source of the transistor TN when the source potential Vs of the transistor TN takes an arbitrary value independently of earth or ground (0 [V]). The resistance value R of the transistor TN may consequently vary according to the source potential Vs. Therefore, in the first embodiment, the control voltage Vgsa is indirectly applied between the gate and source of the transistor TN. As a preferred example in this case in the first embodiment, the control voltage applying section 9 includes the voltage-controlled voltage source 19. The control voltage Vgsa may however be applied directly between the gate and source of the transistor TN, for example, when the source potential Vs of the transistor TN takes a constant value and/or when the change in the resistance value R due to the fluctuation of the source potential Vs is acceptable, The voltage-controlled voltage source 19 is connected between the gate and source terminals of the transistor TN. The voltage-controlled voltage source 19 includes two terminals for input and two terminals for output. The voltage-controlled voltage source 19 is a voltage source in which a potential difference between the two output terminals is determined according to a potential difference between the two input terminals. The control voltage Vgsa with a reference designated 0 [V] and the voltage 0 [V] as the reference are input from the control voltage generator 10 to the voltage-controlled voltage source 19, whereby the control voltage Vgsa is input as the potential difference. The two output terminals of the voltage-controlled voltage source 19 are connected to the gate and source terminals of the transistor TN, respectively. The control voltage Vgs having the same voltage value as the control voltage Vgsa is accordingly applied between the gate and source of the transistor TN. At this time, even if the source potential Vs fluctuates, the potential difference between the two output terminals of the voltage-controlled voltage source 19, that is, the control voltage Vgs does not fluctuate.

Further, the control voltage Vgsa as the potential difference may be input to the voltage-controlled voltage source 19, and therefore the voltage 0 [V] as the reference may be set to an arbitrary value. In this case, if the voltage as the reference is Vref and the output voltage from the control voltage generator 10 is "Vgsa+Vref", a potential difference input to the voltage-controlled voltage source 19 becomes Vgsa by "Vgsa+Vref−Vref".

From the above, the voltage applying circuit 1 in FIG. 1 can apply an arbitrary control voltage Vgs expressed as Equation (1) between the gate and source of the transistor TN. Specifically, the drain current Ids through the MOS resistance MR composed of the transistor TN increases substantially linearly with the rising temperature T (Line 502 in FIG. 5 and Line 505 in FIG. 6B). Here, the correction factor β of the correction voltage Vc (FIG. 2) is appropriately set in the voltage applying circuit 1. Accordingly, the voltage applying circuit 1 linearly lowers the control voltage Vgs according to the temperature T, and linearly reduces the drain current Ids. It is consequently possible to suppress the temperature dependence of the drain current Ids. If the temperature dependence of the drain current Ids can be suppressed, the temperature dependence of the physical quantity relating to the transistor TN can be suppressed.

Figure 7A:
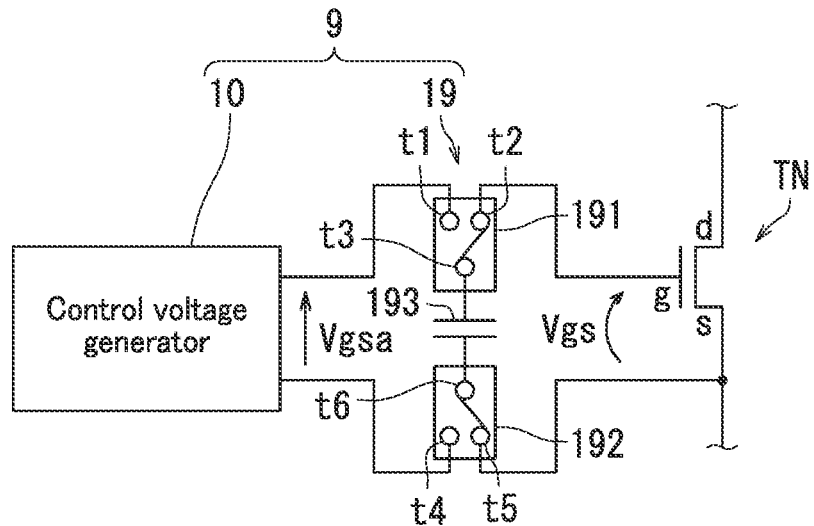
FIG. 7A is a circuit diagram illustrating a first example of a voltage-controlled voltage source in the first embodiment.

A specific circuit will be described first with reference to FIGS. 7A and 7B as an example of the voltage-controlled voltage source 19. FIG. 7A is a circuit diagram illustrating a first example of the voltage-controlled voltage source 19. As illustrated in FIG. 7A, the voltage-controlled voltage source 19 in the first example includes a first switch circuit 191, a second switch circuit 192, and a capacitor 193.

The first switch circuit 191 includes terminals t1 to t3. The terminal t1 is connected to a control voltage generator 10. The terminal t2 is connected to the gate terminal of a transistor TN. The terminal t3 is connected to a first terminal of the capacitor 193.

The second switch circuit 192 includes terminals t4 to t6. The terminal t4 is connected to the control voltage generator 10. The terminal t5 is connected to the source terminal of the transistor TN. The terminal t6 is connected to a second terminal of the capacitor 193.

The control voltage generator 10 generates a control voltage Vgsa. The first switch circuit 191 connects the terminal t3 and the terminal t1. In addition, the second switch circuit 192 connects the terminal t6 and the terminal t4. The capacitor 193 consequently holds the control voltage Vgsa. The first switch circuit 191 subsequently connects the terminal t3 and the terminal t2. In addition, the second switch circuit 192 connects the terminal t6 and the terminal t5. The control voltage Vgsa held in the capacitor 193 is consequently applied as a control voltage Vgs between the gate and source of the transistor TN.

Figure 7B:
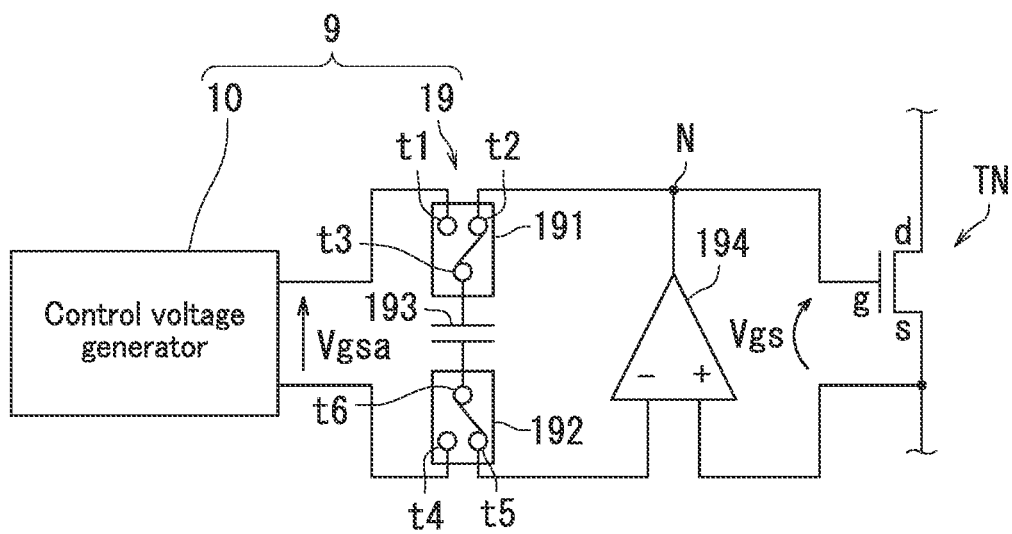
FIG. 7B is a circuit diagram illustrating a second example of the voltage-controlled voltage source in the first embodiment.

FIG. 7B is a circuit diagram illustrating a second example of the voltage-controlled voltage source 19. As illustrated in FIG. 7B, the voltage-controlled voltage source 19 in the second example further includes an operational amplifier 194 in addition to the configuration of the voltage-controlled voltage source 19 in the first example. Hereinafter, components of the second example differing from those of the first example will be mainly described.

In the second example, an output terminal of the operational amplifier 194 is connected to a node N. The node N is located on a line connecting a terminal t2 and the gate terminal of a transistor TN. An inverting input terminal of the operational amplifier 194 is connected to a terminal t5. A non-inverting input terminal of the operational amplifier 194 is connected to the source terminal of the transistor TN. When the operational amplifier 194 forms a feedback circuit as illustrated in FIG. 7B, the non-inverting input terminal and the inverting input terminal have substantially the same potential (virtual short circuit). The potential at the inverting input terminal consequently becomes equal to the source potential Vs of the transistor TN. As a result, the control voltage Vgsa is held in the capacitor 193, and therefore the potential at the node N, which is the output terminal of the operational amplifier 194, becomes "Vgsa+Vs" when the capacitor 193 is connected to the operational amplifier 194. The gate-source voltage Vgs of the transistor TN therefore becomes substantially equal to the control voltage Vgsa.

That is, the operation of the voltage-controlled voltage source 19 in the second example is the same as the operation of the voltage-controlled voltage source 19 in the first example. In the second example, the influence of the capacitive load between the gate and source terminals of the transistor TN can be reduced compared with the first example in particular because the source terminal of the transistor TN is connected to the non-inverting input terminal of the operational amplifier 194.

Note that the configuration of the voltage-controlled voltage source 19 is not particularly limited as long as the voltage-controlled voltage source 19 can be inserted between any two terminals that are electrically floating.

The configuration of the control voltage generator 10 may be, but not particularly limited, configured by any control voltage generating circuit as long as the control voltage Vgsa expressed as Equation (11) can be generated.

Note that FIG. 1 illustrates a physical or logical configuration of the control voltage generator 10. Therefore, when FIG. 1 illustrates the physical configuration of the control voltage generator 10, for example, the reference voltage generator 11 is configured by a reference voltage generating circuit that generates the reference voltage Vgs0. The correction voltage generator 15 is configured by a correction voltage generating circuit that generates the correction voltage Vc based on the detection signal TM by the temperature detector 13. The addition section 17 is configured by an addition circuit that adds the correction voltage Vc to the reference voltage Vgs0.

When FIG. 1 illustrates the logical configuration of the control voltage generator 10, the circuit constituting the control voltage generator 10 is not particularly limited as long as the control voltage generator 10 generates the control voltage Vgsa expressed as Equation (11), for example even when the reference voltage generator 11, the correction voltage generator 15, and the addition section 17 are not clearly distinguished as the physical configuration.

Also regarding the configuration of the temperature detector 13 and the correction voltage generator 15, FIG. 1 illustrates a physical or logical configuration of the temperature detector 13 and the correction voltage generator 15. Therefore, when the temperature detector 13 and the correction voltage generator 15 have the logical configuration, they may be, but not particularly limited, configured by any temperature detecting circuit and correction voltage generating circuit as long as the correction voltage Vc expressed as Equation (2) can be generated, for example even when the temperature detector 13 and the correction voltage generator 15 are not clearly distinguished as the physical configuration.

Figure 8:
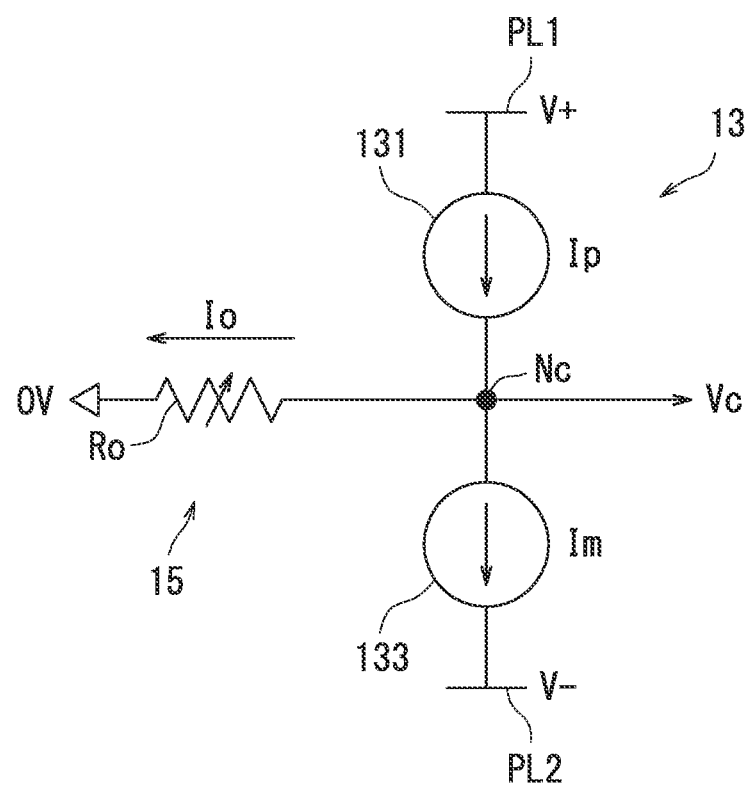
FIG. 8 is a circuit diagram illustrating respective examples of a temperature detector and a correction voltage generator in the first embodiment.

An example of the temperature detector 13 and the correction voltage generator 15 will be described with reference to FIG. 8. FIG. 8 is a circuit diagram illustrating the example of the temperature detector 13 and the correction voltage generator 15. The temperature detector 13 and the correction voltage generator 15 include a first current source circuit 131, a second current source circuit 133, and a variable resistor Ro. The first current source circuit 131 and the second current source circuit 133 are connected in series between a first power supply line PL1 and a second power supply line PL2. A first terminal of the variable resistor Ro is connected to a node Nc between the first current source circuit 131 and the second current source circuit 133. A second terminal of the variable resistor Ro is grounded. In this case, the potential on the first power supply line PL1 takes a positive value, and the first power supply line PL1 is connected to, for example a positive power supply that supplies a positive power supply voltage. On the other hand, the potential on the second power supply line PL2 takes a negative value, and the second power supply line PL2 is connected to, for example a negative power supply that supplies a negative power supply voltage.

The first current source circuit 131 generates a first current Ip. The second current source circuit 133 generates a second current Im. A differential current Jo flows through the variable resistor Ro. The differential current Jo is a current corresponding to a difference between the first current Ip and the second current Im. Specifically, the differential current Jo is a current obtained by subtracting the second current Im from the first current Ip (Io=Ip−Im). When the difference current Jo flows through the variable resistor Ro, a potential difference Vc is generated between both ends of the variable resistor Ro. The potential difference Vc has a value obtained by multiplying the resistance value Ro by the current value Jo (Vc=Ro×Io).

Figure 9A:
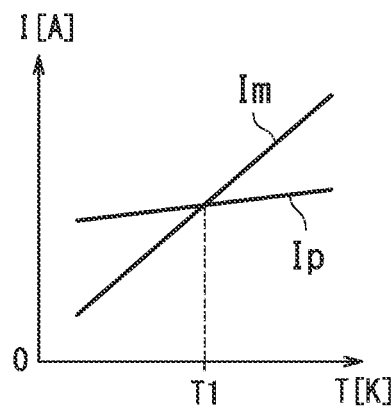
FIG. 9A is a graph illustrating temperature dependence of first current and temperature dependence of second current in the first embodiment.

Although the temperature detector 13 and the correction voltage generator 15 are not clearly distinguished in the circuit of FIG. 8, the temperature dependence in the first current source circuit 131 and the second current source circuit 133 is used for temperature detection. FIG. 9A is a graph illustrating the temperature dependence of the first current Ip and the temperature dependence of the second current Im. Temperature T [K] is on the horizontal axis, and current value I [A] of each current source circuit is on the vertical axis. As illustrated in FIG. 9A, each of the first current Ip and the second current Im varies linearly with respect to change in temperature T. The temperature dependence of the first current Ip differs from the temperature dependence of the second current Im. That is, in the temperature detector 13, the temperature dependence of the first current source circuit 131 differs from the temperature dependence of the second current source circuit 133.

Figure 9B:
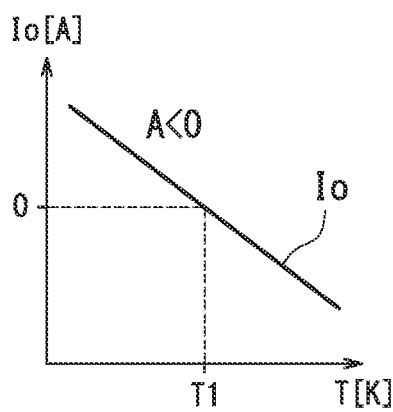
FIG. 9B is a graph illustrating temperature dependence of differential current in the first embodiment.

In the example of FIG. 9A, the temperature dependence of the first current Ip is lower than the temperature dependence of the second current Im. That is, the temperature dependence of the first current source circuit 131 is lower than the temperature dependence of the second current source circuit 133. FIG. 9B illustrates the temperature dependence of the differential current Io (=Ip−Im) flowing through the variable resistor Ro in this case. Temperature T [K] is on the horizontal axis, and differential current value Io [A] is on the vertical axis. As illustrated in FIG. 9B, the differential current Io has a negative temperature characteristic. That is, the slope A of the straight line representing the differential current Io has a negative value. A first temperature T1 in FIG. 9A is a temperature T when the first current Ip coincides with the second current Im. The differential current Io becomes zero at the first temperature T1 as illustrated in FIG. 9B. The differential current Io is therefore expressed as Equation (12). Here, it may be considered that the first current source circuit 131 and the second current source circuit 133 connected in series constitute the temperature detector 13 in FIG. 1. Further, the differential current Io may be considered as the detection signal TM by the temperature detector 13 in FIG. 1.

$$Io = A \times (T - T1) \qquad \text{Equation (12):}$$

Figure 9C:
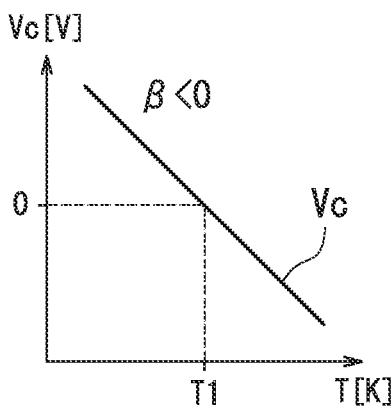
FIG. 9C is a graph illustrating temperature dependence of correction voltage in the first embodiment.

The correction voltage Vc when the differential current Jo is input to the variable resistor Ro is expressed as Equation (13). FIG. 9C is a graph illustrating temperature dependence of the correction voltage Vc. Temperature T [K] is on the horizontal axis, and correction voltage Vc [V] is on the vertical axis. The differential current Jo has a negative temperature characteristic, and therefore the correction voltage Vc also has a negative temperature characteristic as illustrated in FIG. 9C. That is, it coincides with the graph of the temperature dependence of the correction voltage Vc in FIG. 2. The correction voltage Vc becomes zero at the first temperature T1 as illustrated in FIG. 9C. Here, the correction factor β is "Ro×A" as in Equation (13), and takes a negative value like the slope A in Equation (12). It can be seen that if the correction factor β is desired to be varied, the variable resistor Ro should be varied. The variable resistor Ro may be considered as the correction voltage generator 15 in FIG. 1. As is clear from Equation (13), the correction voltage Vc has a value based on the differential current Io.

$$Vc = Ro \times Io = Ro \times A \times (T - T1) = \beta(T - T1) \qquad \text{Equation (13):}$$

Here, the first temperature T1 at which the differential current Io and the correction voltage Vc become zero can be varied by the following method. A method of varying the first temperature T1 in Equations (2), (12) and (13) will be described with reference to FIGS. 8 and 10A to 10C.

Figure 10A:
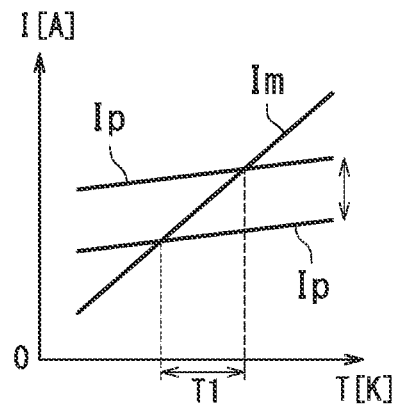
FIG. 10A is a graph illustrating temperature dependence of first current and temperature dependence of second current when current value of first current is varied, in the first embodiment.

FIG. 10A is a graph illustrating temperature dependence of the first current Ip and temperature dependence of the second current Im when the current value of the first current Ip is varied. A first temperature T1 in FIG. 10A is a temperature at which the first current Ip equals the second current Im. The first temperature T1 therefore increases as the current value of the first current Ip increases. That is, the first current source circuit 131 can vary the first temperature T1 by varying the current value of the first current Ip.

Figure 10B:
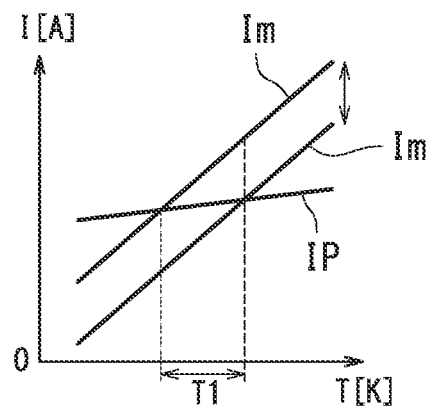
FIG. 10B is a graph illustrating temperature dependence of first current and temperature dependence of second current when current value of second current is varied, in the first embodiment.

The second current source circuit 133 can also vary the first temperature T1 by varying the current value of the second current Im. FIG. 10B is a graph illustrating temperature dependence of the first current Ip and temperature dependence of the second current Im when the current value of the second current Im is varied. The first temperature T1 however decrease when the current value of the second current Im increases as illustrated in FIG. 10B.

Figure 10C:
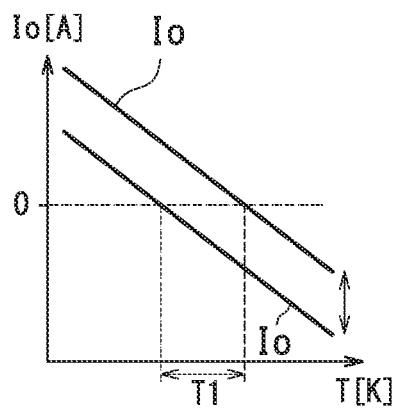
FIG. 10C is a graph illustrating temperature dependence of differential current when current value of differential current is varied, in the first embodiment.

When the current values of the first current Ip and/or the second current Im are varied, the temperature dependence of the differential current Jo also varies according to the current value. FIG. 10C is a graph illustrating temperature dependence of the differential current Jo when the current value of the differential current Jo is varied. The first temperature T1, which is the temperature T at which the differential current Jo becomes zero, increases when the current value of the differential current Jo increases according to the varied current value of the first current Ip and/or the second current Im as illustrated in FIG. 10C. Further, the correction voltage Vc is zero when the differential current Jo is zero.

That is, the circuit example of FIG. 8 in the first embodiment is provided with the first current source circuit 131 and the second current source circuit 133. The first current Ip and/or the second current Im are varied and the differential current Jo is varied, whereby the first temperature T1, which is the temperature T at which the correction voltage Vc becomes zero, can be easily varied.

Note that the second power supply line PL2 may be grounded. In this case, the first terminal of the variable resistor Ro is connected to the node Nc, and the second terminal of the variable resistor Ro is connected to a reference voltage source that generates a reference voltage Vref (0<Vref<PL1 potential). The output voltage of the correction voltage generator 15 is "β(T−T1)+Vref". Therefore, by setting the output voltage of the reference voltage generator 11 to "Vgs0−Vref", Vgsa=Vgs0+β(T−T1) is obtained like Equation (11).

Although the slopes of the straight lines representing the first current Ip and the second current Im have positive values in the examples of FIGS. 9A and 10, they do not necessarily have the positive values. In the first embodiment, in order that the correction factor β of the correction voltage Vc becomes negative in order to correct the temperature dependence of the transistor TN, it is sufficient that the slope of the second current Im is larger than the slope of the first current Ip. The sign of the slope is irrelevant.

As described above, the configuration of the resistance device 100 of FIG. 1 in the first embodiment enables correction to the temperature dependence of the transistor TN by appropriately setting the correction factor β of the correction voltage Vc. According to this configuration, Equations (1) and (2) are substituted into Equation (9), whereby the drain current Ids of the transistor TN is expressed as Equation (14) reflecting the correction factor β in the linear region (Vds<Vgs−Vth) of the "Vgs>Vth" region.

[Math. 8]

$$I_{ds} = \mu_{n\_} T_0 \cdot (T/T_0)^{\alpha \mu} \cdot \qquad \text{Equation (11)}$$

$$C_{ox} \frac{W}{L} \left[ (V_{gs0} + \beta(T - T_1) - V_{th\_} T_0 - \alpha_{th}(T - T_0)) V_{ds} - \frac{1}{2} V_{ds}^2 \right]$$

Equations (1) and (2) are substituted into Equation (1), whereby the drain current Ids of the transistor TN is expressed as Equation (15) reflecting the correction factor β in the saturation region (Vds>Vgs−Vth) in the "Vgs>Vth" region.

[Math. 9]

$$I_{ds} = \frac{1}{2} \mu_{n\_} T_0 \cdot (T/T_0)^{\alpha \mu} \cdot \qquad \text{Equation (12)}$$

$$C_{ox} \frac{W}{L} (V_{gs0} + \beta(T - T_1) - V_{th\_} T_0 - \alpha_{th}(T - T_0))^2$$

Equations (14) and (15) include a correction element that varies linearly with respect to temperature T, that is, the correction voltage Vc (=β(T−T1)). Further, the resistance value R of the transistor TN is expressed as Equation (16) in both the linear region and the saturation region of the "Vgs>Vth" region.

$$R = Vds/Ids \qquad \text{Equation (16):}$$

By appropriately setting the correction factor β, the temperature dependence of the drain current Ids of the transistor TN is eliminated. In other words, by appropriately setting the correction factor β, the temperature dependence of the resistance value R (Equation (16)) based on the drain current Ids is eliminated. An example of a method for determining the correction factor β that determines the correction voltage Vc will be described with reference to FIG. 11A. In this example, we focus on the saturation region of the transistor TN.

Figure 11A:
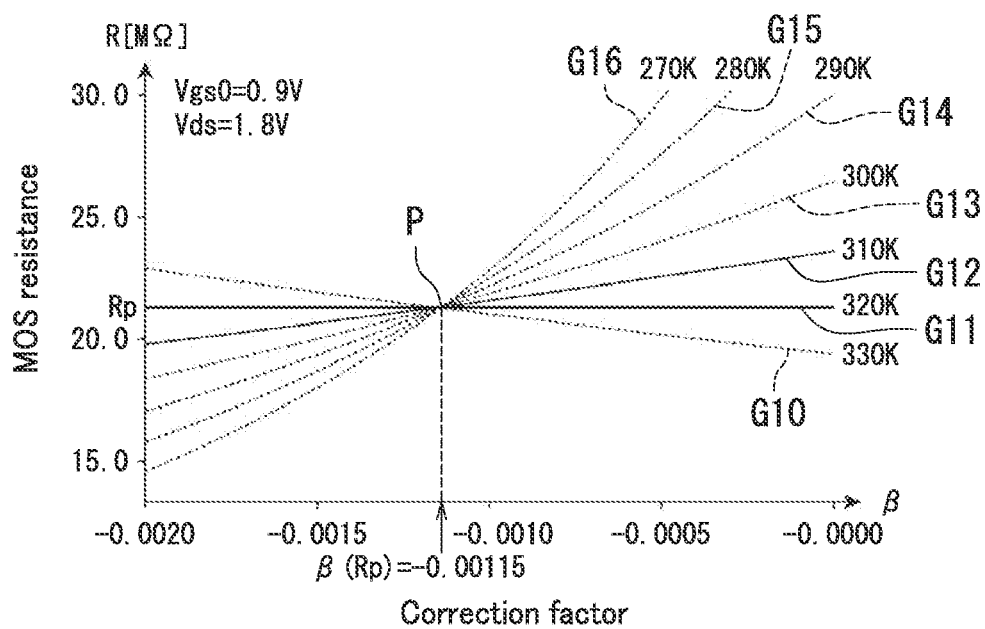
FIG. 11A is a graph illustrating the relationship between correction factor and resistance value of the transistor at a plurality of different temperatures in the first embodiment.

FIG. 11A is a graph illustrating the relationship between the correction factor β and the resistance value R of the transistor TN at a plurality of different temperatures. Correction factor β is on the horizontal axis, and resistance value R [MΩ] is on the vertical axis.

As illustrated in FIG. 11A, R-β curves G10 to G16 are obtained by simulating the resistance value R based on Equations (15) and (16) in the saturation region of the "Vgs>Vth" region. Simulation conditions using standard circuit parameters are $\mu n\_T0 \cdot Cox=170.0\ \mu A/V^2$, W=0.6 μm, L=60.0 μm, αth=−1.7 mV/K, αμ=−1.5, Vth_T0=0.7V, T0=300K, and T1=320K. The reference voltage Vgs0 is 0.9V, and the drain-source voltage Vds is 1.8V.

The R-β curves G10, G11, G12, G13, G14, G15, and G16 illustrate the relationship between the resistance value R and the correction factor at T=330K, 320K, 310K, 300K, 290K, 280K, and 270K, respectively.

The gradients of the R-β curves G10 to G16 depend on temperature T and differ from each other. The R-β curves G10 to G16 intersect at almost one-point P. As can be understood from FIG. 11A, at the intersection P, the resistance value R of the transistor TN is substantially independent of the temperature T.

The correction factor β and the resistance value R of the transistor TN at the intersection P are "β (Rp)" and "Rp", respectively. In Equation (2), the correction factor is set to β (Rp). In this case, the temperature dependence of the transistor TN can be cancelled by the correction voltage Vc including the correction factor β (Rp). The temperature dependence of the resistance value R of the transistor TN can consequently be reduced. In other words, the resistance value R of the transistor TN can be maintained substantially constant with respect to fluctuations in the temperature T. Hereinafter, the fact that the resistance value R is almost independent of temperature may be described as "temperature-independent" or "without temperature dependence".

In order to obtain the correction factor β (Rp), at least two R-β curves may be found. Note that as can be understood from Equations (15) and (16), when the reference voltage Vgs0 varies, the R-β curve also varies. The position of the intersection P therefore varies when the reference voltage Vgs0 varies. The correction factor β (Rp) consequently varies when the reference voltage Vgs0 varies.

Here, preferably at two or more temperatures T, two or more R-β curves are obtained by actually measuring the resistance value R of the transistor TN in the resistance device 100 in FIG. 1 while varying the correction factor β. The correction factor β (Rp) at the intersection P of the two or more R-β curves is then obtained. Further, the correction factor β (Rp) is set to the correction factor β of the correction voltage generator 15 in the resistance device 100. R-β curves are actually measured in particular, and therefore the correction factor β (Rp) suitable for the transistor TN actually used can be determined. It is consequently possible to further reduce the temperature dependence of the resistance value R of the transistor TN.

Note that the temperature T which corresponds to the ambient temperature of the resistance device 100 is set through, for example a constant temperature chamber in which the resistance device 100 is placed.

As described above with reference to FIG. 11A, the first embodiment enables acquisition of the correction factor β (Rp) when the resistance value R is independent of the temperature T based on the intersection of the R-β curves G10 to G16.

Figure 12A:
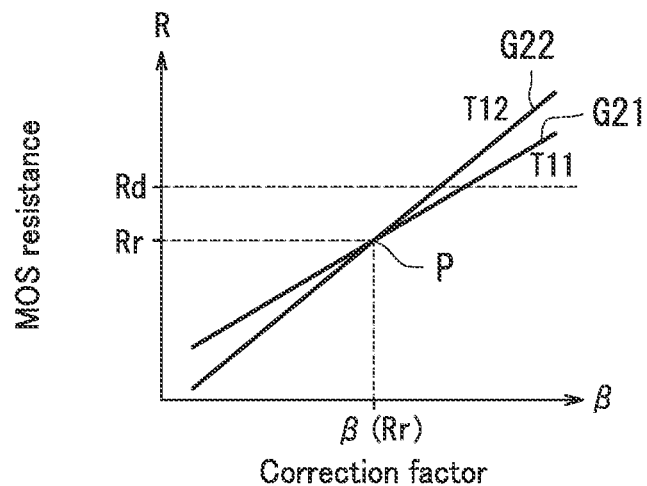
FIG. 12A is a graph illustrating R-β curves of resistance value of the transistor against correction factor at any two different temperatures in the first embodiment.

Next, a more preferable example of the correction factor (β) determining method will be described with reference to FIGS. 12A and 12B. FIG. 12A is a graph illustrating R-β curves G21 and G22, at any two different temperatures T11 and T12, each of which represents the resistance value R of the transistor TN with respect to the correction factor β. Correction factor β is on the horizontal axis represents, and resistance value R is on the vertical axis.

Two R-β curves G21 and G22 are first obtained by measuring the resistance value R of the transistor TN in the resistance device 100 while varying the correction factor β at each of the temperature T11 and the temperature T12. A correction factor β (Rr) is then acquired from the intersection P of the two R-β curves G21 and G22. The resistance value R when the correction factor β is the correction factor β (Rr) is a resistance value Rr without temperature dependence. The correction factor β (Rr) is therefore set to the correction factor β of the correction voltage generator 15 in the resistance device 100, so that the correction voltage Vc enables effective reduction in the temperature dependence of the resistance value R of the transistor TN.

However, the resistance value Rr without temperature dependence at the intersection P basically do not match a desired resistance value Rd (hereinafter, may be referred to as a "target resistance value Rd"). This is because, as illustrated in FIG. 12A, the resistance value R of the transistor TN at each of arbitrary temperatures T11 and T12 fluctuates according to the correction factor β, and it is therefore unknown what the resistance value Rr at the intersection P will be at the time of obtaining the R-β curve at each temperature.

In this case, what is required to match the resistance value Rr with the target resistance value Rd is measuring the resistance value R with respect to the correction factor β at each of two different temperatures while varying the reference voltage Vgs0 to repeatedly search for the intersection of the R-β curves with respect to the reference voltage Vgs0 until the target resistance value Rd and the resistance value Rr at the intersection coincide with each other.

Attention is therefore paid to the R-β curve G11 when the temperature T in FIG. 11A is 320K, in order to more efficiently determine the correction factor β (Rd) corresponding to the target resistance value Rd. In the example of FIG. 11A, when the temperature T is 320K, the resistance value R of the transistor TN becomes substantially constant Rp without depending on the correction factor β as illustrated in the R-β curve G11.

There is therefore no effect of correction by the correction voltage Vc containing the correction factor β when the temperature T is 320K. In other words, the correction voltage Vc is zero when the temperature T is 320K. Moreover, the temperature T of 320K is a temperature at which the correction voltage Vc becomes zero. The temperature T of 320K therefore corresponds to the first temperature T1 in Equation (2).

Figure 12B:
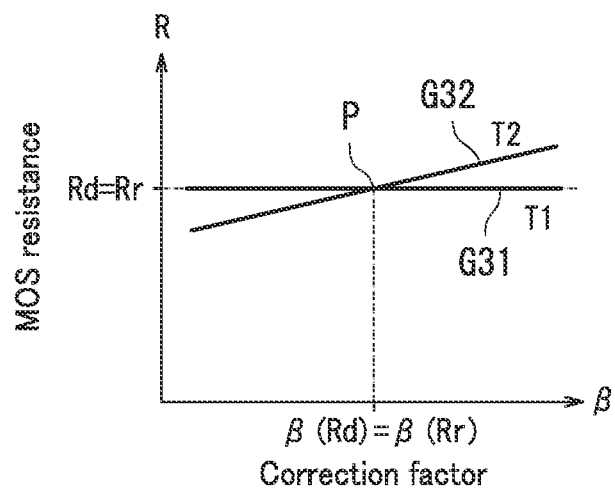
FIG. 12B is a graph illustrating R-β curves of resistance values of the transistor against correction factors at first temperature and second temperature in the first embodiment.

FIG. 12B is a graph illustrating the relationship between an R-β curve G31 representing the resistance value R of the transistor TN with respect to the correction factor β at the first temperature T1 and an R-β curve G32 representing the resistance value R of the transistor TN with respect to the correction factor β at the second temperature T2. Correction factor β is on the horizontal axis, and resistance value R is on the vertical axis.

As illustrated in FIG. 12B, the R-β curve G31 represents the resistance value R of the transistor TN at the first temperature T1. The first temperature T1 is a temperature when the physical quantity relating to the transistor TN is substantially constant with respect to change in the correction factor β. In the example of FIG. 12B, the first temperature T1 is a temperature when the resistance value R of the transistor TN is substantially constant with respect to change in the correction factor β. That is, the first temperature T1 is a temperature at which the correction voltage Vc becomes zero. The resistance value R is a resistance value Rr without temperature dependence at the first temperature T1.

At the first temperature T1 which is a temperature when the correction voltage Vc becomes zero, the resistance value R of the resistance device 100 is actually measured while the reference voltage Vgs0 is being varied, so that the reference voltage Vgs0 (Rd) when the resistance value R becomes the target resistance value Rd is obtained.

The resistance device 100 subsequently obtains the R-β curve G32 by setting the reference voltage Vgs0 and the temperature T to the reference voltage Vgs0 (Rd) and the second temperature T2 different from the first temperature T1, respectively, and actually measuring the resistance value R while varying the correction factor β. The R-β curve G32 represents the resistance value R of the transistor TN at the second temperature T2.

The correction factor β (Rr) at the intersection P of the R-β curve G31 at the first temperature T1 and the R-β curve G32 at the second temperature T2 is then acquired. The resistance value Rr, without temperature dependence, corresponding to the correction factor β (Rr) always coincides with the target resistance value Rd. In this case, the correction factor β (Rr) at the intersection P also coincides with the correction factor β (Rd) with respect to the target resistance value Rd. In the first embodiment, the correction factor β (Rd) is therefore set to the correction factor β of the correction voltage generator 15 in the resistance device 100, so that the correction voltage Vc enables effective reduction in the temperature dependence of the resistance value R of the transistor TN. The resistance value R of the transistor TN can consequently be maintained at the target resistance value Rd.

The plurality of R-β curves G10 to G16 do not exactly intersect at one point due to the influence of non-linearity in particular as described with reference to FIG. 11A. It is therefore preferable that the correction factor β (Rd) is obtained by setting the second temperature T2 to a value near the temperature at which the transistor TN is actually used. For example, when the transistor TN is used near the body temperature as in an electronic device that detects biological information, the second temperature T2 is set to 310K, which is a value near the human body temperature, and the first temperature T1 is set to 320K, which is a value near the temperature T2.

Note that the correction factor β (Rp) is −0.00115 at the intersection of the R-β curve G11 corresponding to the first temperature T1 of 320K and the R-β curve G12 corresponding to the second temperature T2 of 310K in FIG. 11A, for example. The correction factor β (Rp) is set to −0.00115 in Equation (15), and the resistance value R of the transistor TN is calculated from Equations (15) and (16).

Figure 11B:
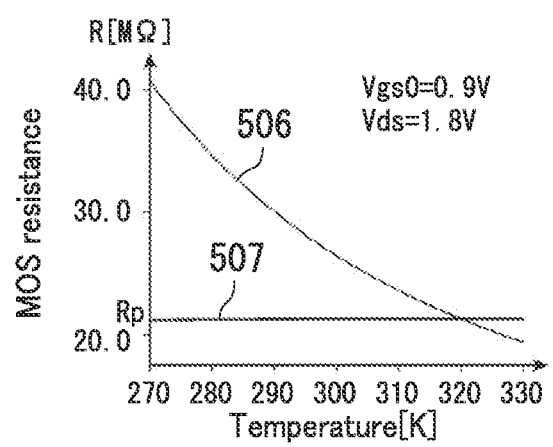
FIG. 11B is a graph illustrating the effect of temperature correction to temperature dependence of resistance value of the transistor in the first embodiment.

FIG. 11B is a graph illustrating the effect of temperature correction to the temperature dependence of the resistance value R of the transistor TN. The curve 506 represents values when the temperature correction is not performed, and the curve 507 represents values when the temperature correction is performed. Temperature T [K] is on the horizontal axis, and resistance value R [MΩ] is on the vertical axis. In the case of no temperature correction, the correction factor β in Equation (15) was set to zero, the resistance value R was calculated from Equation (16), and the curve 506 was plotted. As is clear from the curve 506, when the correction is not performed, the resistance value R depends strongly on temperature.

In the case of performance of temperature correction, the correction factor β in Equation (15) was set to −0.00115 of the correction factor β (Rp) obtained from FIG. 11A, the resistance value R was calculated from Equation (16), and the curve 507 was plotted. As is clear from the curve 507, the resistance value R is substantially constant, and has a value Rp. That is, the correction based on the correction factor β (Rp) makes it possible to strongly suppress the temperature dependence of the resistance value R of the transistor TN.

The above describes the methods of the first embodiment, for obtaining a combination of the correction factor β (Rd) and the target resistance value Rd without temperature dependence. In the methods, a method of repeatedly finding and searching for the intersection of R-β curves at arbitrary two different temperatures while varying the reference voltage Vgs0 has been described with reference to FIG. 12A. Another method of uniquely identifying the intersection P of the R-β curve at the first temperature T1 that does not depend on the correction factor β and the R-β curve at the second temperature T2 different from the first temperature T1. The latter can determine the combination at a higher speed than the former. The voltage applying circuit 1 including the correction voltage generator 15 that generates a correction voltage Vc by which the correction effect disappears at the first temperature T1 is suitable for realization of the decision method of the correction factor β (Rd) and the target resistance value Rd without temperature dependence in particular.

Note that the target resistance value Rd corresponds to an example of the "target physical quantity relating to the field-effect transistor". That is, the target resistance value Rd is a resistance value of the field-effect transistor TN, which is measurable from an electronic circuit including the field-effect transistor TN. The target resistance value Rd is a resistance value that is set as a target value.

Figure 13A:
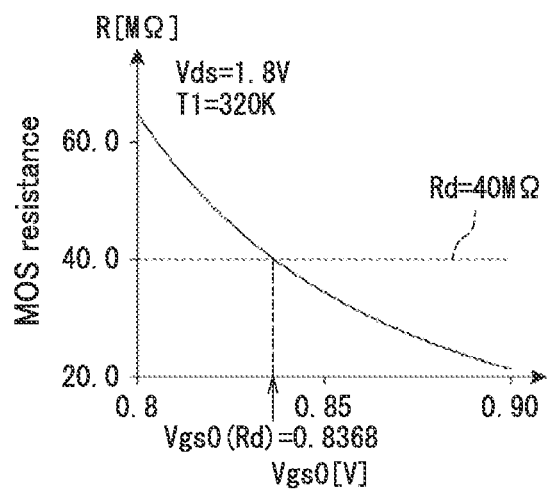
FIG. 13A is a graph illustrating the relationship between reference voltage and resistance value of the transistor at first temperature in the first embodiment.
Figure 13B:
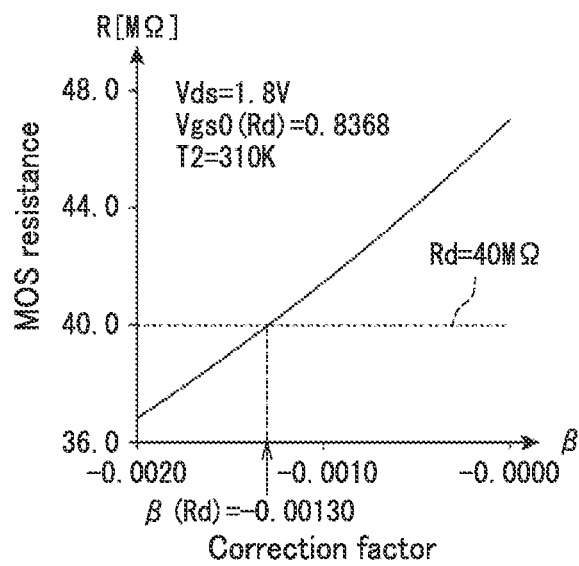
FIG. 13B is a graph illustrating the relationship between correction factor and resistance value of the transistor at second temperature in the first embodiment.

Next, a more preferable example of the method for determining the correction factor will be described with reference to FIGS. 13A to 13C. FIG. 13A is a graph illustrating the relationship between the resistance value R of the transistor TN and the reference voltage Vgs0 at the first temperature T1 (=320K). FIG. 13B is a graph illustrating the relationship between the resistance value R of the transistor TN and the correction factor β at the second temperature T2 (=310K). In FIG. 13A, reference voltage Vgs0 [V] is on the horizontal axis. In FIG. 13B, correction factor β is on the horizontal axis. In FIGS. 13A and 13B, resistance value R [MΩ] is on the vertical axis. The correction factor β is determined by (Procedure 1) and (Procedure 2) described below.

(Procedure 1)

As illustrated in FIG. 13A, at the first temperature T1 where the correction voltage Vc becomes zero, the reference voltage Vgs0 (Rd) when the resistance value R of the transistor TN in the resistance device 100 becomes the target resistance value Rd (40 MΩ in the example of FIG. 13A). Note that at the first temperature T1, the correction voltage Vc is zero and therefore the correction factor β may be any value, and the reference voltage Vgs0 (Rd) coincides with the control voltage Vgsa in FIG. 1 and Equation (11).

Specifically, the resistance device 100 is first placed in a constant temperature chamber, and the ambient temperature of the resistance device 100 is set to the first temperature T1 by the constant temperature chamber. The resistance value R is then measured while the voltage value of the reference voltage Vgs0 is being varied. The reference voltage Vgs0 (Rd) when the resistance value R corresponds to the target resistance value Rd is then determined.

(Procedure 2)

As illustrated in FIG. 13B, at the second temperature T2 and the reference voltage Vgs0 (Rd), the correction factor β (Rd) when the resistance value R of the transistor TN becomes the target resistance value Rd (40 MΩ in the example of FIG. 13B) is determined.

Specifically, the resistance device 100 is first placed in a constant temperature chamber, and the ambient temperature of the resistance device 100 is set to the second temperature T2 by the constant temperature chamber. The reference voltage Vgs0 is then set to the reference voltage Vgs0 (Rd) determined in (Procedure 1). The resistance value R is then measured while the value of the correction factor β is being varied. The correction factor β (Rd) when the resistance value R corresponds to the target resistance value Rd is then determined.

The performance of (Procedure 2) means the acquisition of the correction factor β(Rd) at the intersection P of the R-β curve G31 at the first temperature T1 and the R-β curve G32 at the second temperature T2. The reason is as follows. As illustrated in FIG. 12B, at the second temperature T2, the resistance value R coincides with the target resistance value Rd only at the intersection P. Therefore, the correction factor β when the resistance value R corresponds to the target resistance value Rd at the second temperature T2 always coincides with the correction factor β (Rd) at the intersection P. At the intersection P, the resistance value R corresponds to the resistance value Rr without temperature dependence, so that the target resistance value Rd coincides with the resistance value Rr without temperature dependence.

As described above with reference to FIGS. 13A and 13B, in the first embodiment, the correction factor β (Rd) in which the target resistance value Rd matching the resistance value Rr without temperature dependence is determined through (Procedure 1) and (Procedure 2). There is therefore unnecessary to repeatedly obtain the intersection of the R-β curves at any two different temperatures while varying the reference voltage Vgs0. It is consequently possible to uniquely and quickly identify the combination of the correction factor β (Rd) and the target resistance value Rd without temperature dependence.

That is, in the first embodiment, the value of the correction factor β (Rd) corresponds to a value when the target resistance value Rd is obtained at the second temperature T2 different from the first temperature T1 based on the reference voltage Vgs0 (Rd) when the target resistance value Rd of the transistor TN is obtained at the first temperature T1.

The voltage applying circuit 1 including the correction voltage generator 15 that generates the correction voltage Vc by which the correction effect disappears at the first temperature T1 is suitable for realization of (Procedure 1) and (Procedure 2) in particular.

Here, the resistance value R in FIGS. 13A and 13B is derived from the simulation results based on Equations (15) and (16). Simulation conditions using standard circuit parameters are $\mu n\_T0 \cdot Cox = 170.0$ µA/V$^2$, W=0.6 µm, L=60.0 µm, αth=−1.7 mV/K, αµ=−1.5, Vth_T0.=0.7V, and T0=300K. Further, in FIG. 13A, T=T1=320K. In FIG. 13B, T=T2=310K.

In FIGS. 13A and 13B, Vgs0 (Rd)=0.8368V and β (Rd)=−0.00130.

Figure 13C:
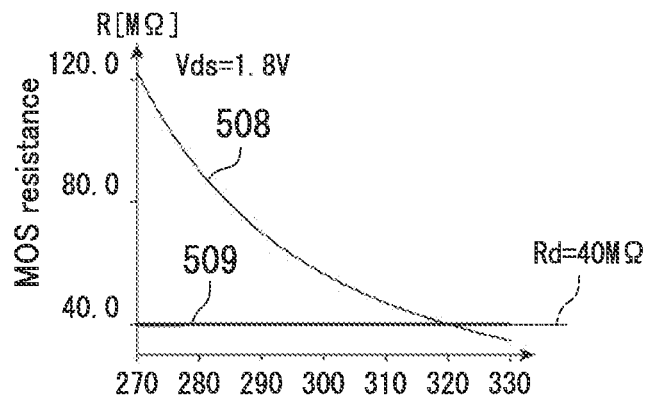
FIG. 13C is a graph illustrating the effect of temperature correction to temperature dependence of resistance value of the transistor in the first embodiment.

FIG. 13C is a graph illustrating the effect of temperature correction to the temperature dependence of the resistance value R of the transistor TN. The curve 508 represents values when the temperature correction is not performed, and the curve 509 represents values when the temperature correction is performed. Temperature T [K] is on the horizontal axis, and resistance value R [MΩ] is on the vertical axis. In the case of no temperature correction, the correction factor β in Equation (15) was set to zero, the reference voltage Vgs0 was set to 0.8368V as Vgs0 (Rd) obtained in (Procedure 1), the resistance value R was calculated from Equation (16), and the curve 508 was plotted. As is clear from the curve 508, when the correction is not performed, the resistance value R depends strongly on temperature.

On the other hand, in the case of performance of temperature correction, the correction factor β in Equation (15) was set to −0.00130 as β (Rd) obtained in (Procedure 2), the resistance value R was calculated from Equation (16), and the curve 509 was plotted. As is clear from the curve 509, the resistance value R is substantially constant, and has a value Rd. That is, the correction based on the correction factor β (Rd) makes it possible to strongly suppress the temperature dependence of the resistance value R of the transistor TN.

As described above with reference to FIGS. 11B and 13C, it has been confirmed that in the saturation region (Vds>Vgs−Vth) with strong non-linearity of the "Vgs>Vth" region, the temperature correction to the drain current Ids and the resistance value R (MOS resistance) can be appropriately performed based on the correction factor β (Rp) or the correction factor β (Rd).

That is, the voltage applying circuit 1 in FIG. 1 applies the control voltage Vgs (=Vgs0+R (T−T1)) between the gate and source of the transistor TN, and controls the resistance value R between the drain and source of the transistor TN in the saturation region. This makes it possible to strongly suppress the temperature dependence of the resistance value R of the transistor TN.

As described with reference to FIGS. 11B and 13C, it has been confirmed that the temperature correction to the drain current Ids and the resistance value R (MOS resistance) can be appropriately performed even in the saturation region with strong non-linearity. The temperature correction to the drain current Ids and the resistance value R (MOS resistance) can therefore be performed more precisely in the linear region (Vds<Vgs−Vth) with high linearity of the "Vgs>Vth" region. Also in this case, the correction factor β (Rp) corresponding to the resistance value Rp without temperature dependence or the correction factor β (Rd) corresponding to the resistance value Rd without temperature dependence is determined by the procedure similar to the procedures described with reference to FIGS. 11A to 13C.

That is, preferably the voltage applying circuit 1 in FIG. 1 applies the control voltage Vgs (=Vgs0+3 (T−T1)) between the gate and source of the transistor TN, and controls the resistance value R between the drain and source of the transistor TN in the linear region.

As described above, the voltage applying circuit 1 in FIG. 1 applies the control voltage Vgs between the gate and source of the transistor TN to control the resistance value R between the drain and source of the transistor TN in the "Vgs>Vth" region.

Here, if the subthreshold region of the transistor TN is used, a higher resistance value R can be realized without changing the size (gate length L and gate width W) of the transistor TN. The subthreshold region corresponds to the operating region (Vgs<Vth) of the transistor TN when the magnitude of the gate-source voltage Vgs (voltage between the gate and source) is smaller than the magnitude of the threshold voltage Vth. In the subthreshold region, for example, when the aspect ratio (W/L) of the transistor TN is 0.01, a resistance value R of several MΩ to several tens of TΩ can be realized. The subthreshold region corresponds to an example of the "second operating region of the field-effect transistor".

The configuration of the voltage applying circuit 1 in FIG. 1 can be adopted even when the subthreshold region of the transistor TN is used. The voltage applying circuit 1 therefore applies the control voltage Vgs (=Vgs0+3 (T−T1)) between the gate and source of the transistor TN to control the resistance value R between the drain and source of the transistor TN in the subthreshold region.

In the subthreshold region, the drain current Ids increases exponentially with respect to the gate-source voltage Vgs. The operating characteristics of the transistor TN as the MOS resistance therefore differs from the saturation region and the linear region in the "Vgs>Vth" region.

Therefore, the reason why the control voltage Vgs can be corrected even in the subthreshold region by the linear function expressed as Equation (2) will be described with reference to FIGS. 14A to 16B.

Figure 14A:
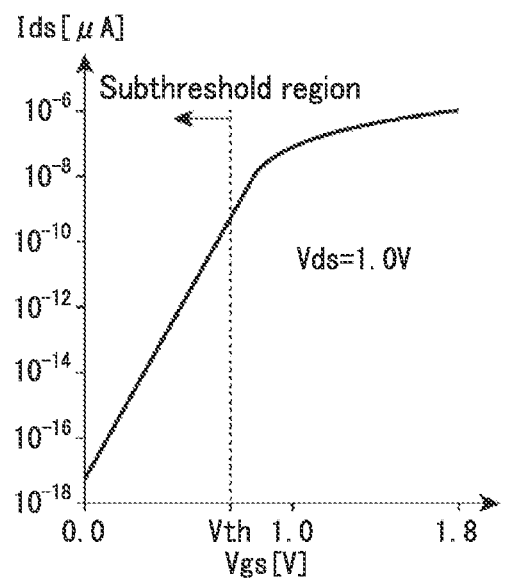
FIG. 14A is a semi-log graph illustrating Ids-Vgs characteristics of a general NMOS transistor.

FIG. 14A is a semi-logarithmic graph illustrating Ids-Vgs characteristics of a general NMOS transistor. Gate-source voltage Vgs [V] is on the horizontal axis, and drain current Ids [μA] on a logarithmic scale is on the vertical axis. As illustrated in FIG. 14A, the region represented by "Vgs<Vth" is the subthreshold region. In the subthreshold region, the logarithm $\log_{10}$ Ids of the drain current Ids is proportional to the gate-source voltage Vgs.

Figure 14B:
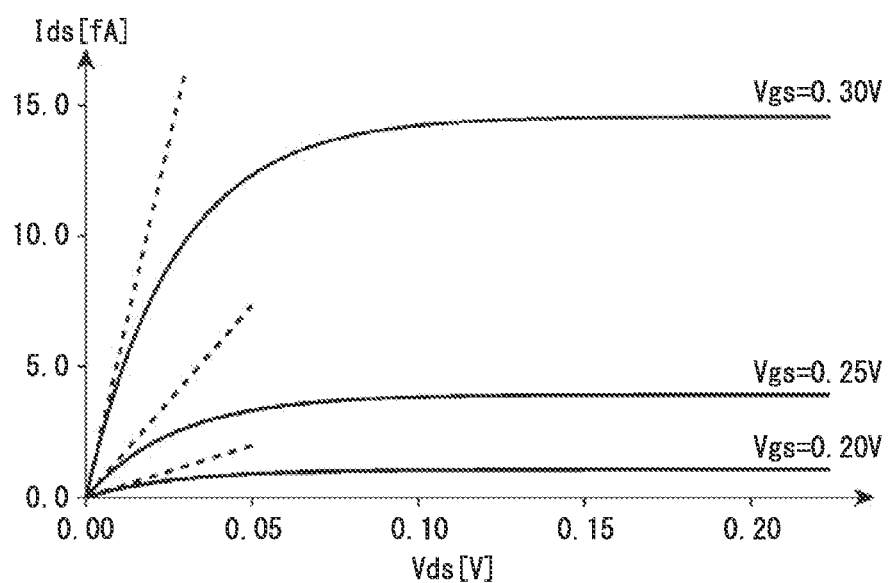
FIG. 14B is a graph illustrating Ids–Vds characteristics of the general NMOS transistor in the subthreshold region.

FIG. 14B is a graph illustrating the Ids–Vds characteristics of the general NMOS transistor in the subthreshold region. Drain-source voltage Vds [V] is on the horizontal axis, and drain current Ids [fA] is on the vertical axis. FIG. 14B illustrates the drain currents Ids at Vgs=0.20V, 0.25V, and 0.30V.

The drain current Ids in the subthreshold region is expressed as Equation (17). The Vt in Equation (17) is called a thermal voltage and expressed as Equation (18). In Equation (18), k denotes Boltzmann's constant and q denotes an elementary charge. Further, i in Equation (17) is expressed as Equation (19). In Equation (19), Cd denotes depletion layer capacity. FIG. 14A illustrates the simulation result by Equation (17). As can be understood from Equation (17), the drain current Ids of the transistor TN increases according to an exponential function with increasing gate-source voltage Vgs. Therefore, in the subthreshold region, the logarithm of the drain current Ids is proportional to the gate-source voltage Vgs as illustrated in FIG. 14A.

[Math. 10]

$$I_{ds} = \mu_n C_{ox} \frac{W}{L}(\eta-1)V_t^2 e^{\frac{V_{gs}-V_{th}}{\eta V_t}}\left(1 - e^{-\frac{V_{ds}}{V_t}}\right) \quad \text{Equation (17)}$$

$$V_t = kT/q \quad \text{Equation (18)}$$

$$\eta = 1 + (Cd/Cox) \quad \text{Equation (19)}$$

In the subthreshold region, the range in which the Ids–Vds characteristics can be linearly approximated is as narrow as Vds<several tens of mV. Therefore, as an example, an NMOS transistor is used as non-linear MOS resistance having a high resistance value. Specifically, the drain current Ids can be linearly approximated as in Equation (20) from the tangent equation based on Equation (17) at Vds=0. The straight lines depicted by the broken lines in FIG. 14B are derived from simulation results using standard circuit parameters according to Equation (20) at Vgs=0.20V, 0.25V, and 0.30V. It can be seen from the example of FIG. 14B that linear approximation is possible in the range of Vds<several tens of mV. The smaller the Vgs, the smaller the slope of the straight line depicted by each broken line in FIG. 14B. The Ids–Vds characteristics in the range of Vds<several tens of mV correspond to the linear region of the "Vgs>Vth" region.

[Math. 11]

$$I_{ds} = \mu_n C_{ox} \frac{W}{L}(\eta-1)V_t e^{\frac{V_{gs}-V_{th}}{\eta V_t}} \cdot V_{ds}$$

On the other hand, when Vds becomes large, the drain current Ids of the transistor TN is saturated at a constant value. In the example of FIG. 14B, it can be seen that the drain current Ids is saturated at a constant value in the range of Vds>100 mV. The Ids–Vds characteristics in the range of Vds>100 mV correspond to the saturation region of the "Vgs>Vth" region.

That is, the drain current Ids of the transistor TN in the subthreshold region (Vgs<Vth) is expressed as Equation (17). The drain current Ids of the transistor TN in the linear region of the "Vgs>Vth" region is expressed as Equation (4). The drain current Ids of the transistor TN in the saturation region is expressed as Equation (3). Here, Equation (17) represents both the characteristics in Equation (4) and the characteristics in Equation (3) in one Equation. Even in the subthreshold region, the resistance value R of the transistor TN is expressed as Equation (21).

$$R = V_{ds}/I_{ds} \quad \text{Equation (21):}$$

As can be understood from Equation (17), the drain current Ids can be controlled exponentially by the gate-source voltage Vgs. The fact that the drain current Ids can be controlled by Vgs is synonymous with the fact that the resistance value R of the NMOS transistor can be controlled by Vgs because of Equation (21): R=Vds/Ids.

Figure 15A:
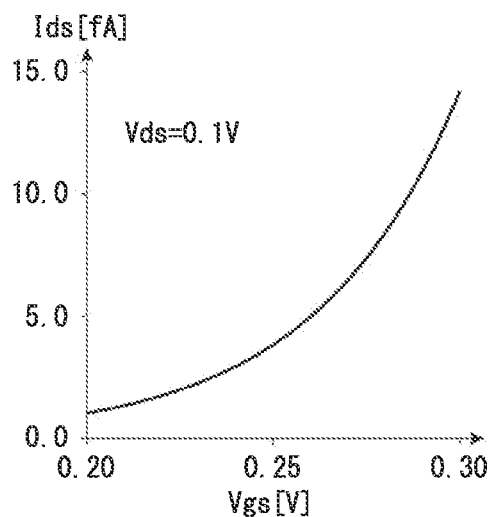
FIG. 15A is a graph illustrating Ids-Vgs characteristics of a general NMOS transistor in the subthreshold region.
Figure 15B:
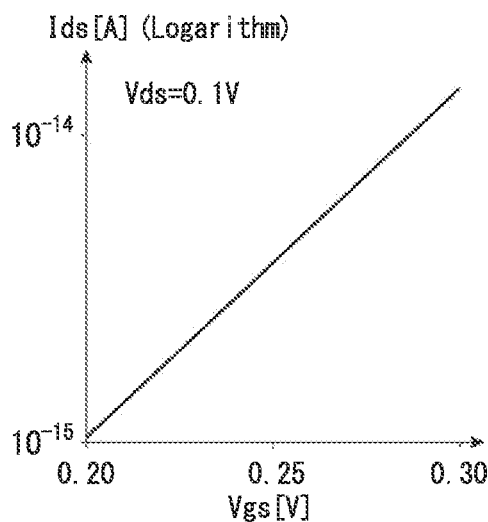
FIG. 15B is a semi-logarithmic graph illustrating Ids-Vgs characteristics of the general NMOS transistor in the subthreshold region.
Figure 15C:
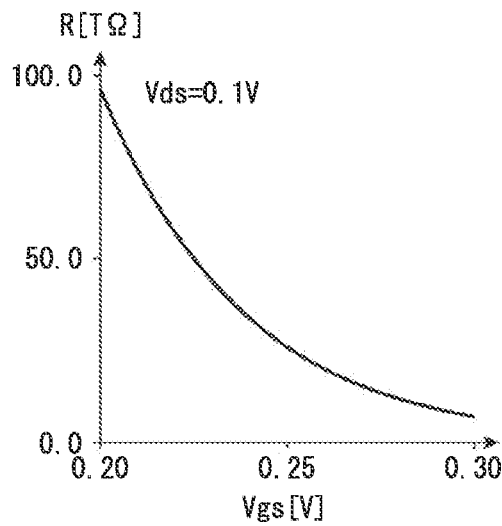
FIG. 15C is a graph illustrating the relationship between Vgs and resistance value of the general NMOS transistor in the subthreshold region.

Therefore, FIG. 15 illustrates how gate-source voltage Vgs has relationships with the drain current Ids and the resistance value R of a general NMOS transistor in the subthreshold region. FIG. 15 illustrates simulation results using standard circuit parameters based on Equation (17). In FIGS. 15A to 15C, gate-source voltage Vgs [V] is on the horizontal axis. In FIG. 15A, drain current Ids [fA] is on the vertical axis. In FIG. 15B, drain current Ids [A] of the semi-logarithmic graph is on the vertical axis on a logarithmic scale. In FIG. 15C, the graph of drain current Ids in FIG. 15A is converted into the resistance value R by Equation (21), and resistance value R [TΩ] is on the vertical axis. In this case, Vds is 0.1V.

As illustrated in FIG. 15A, in the subthreshold region, the drain current Ids increases exponentially with respect to the gate-source voltage Vgs. A $\log_{10}$ Ids of the drain current Ids is therefore proportional to the gate-source voltage Vgs in the subthreshold region as illustrated in FIG. 15B. Further, a high resistance value R (=Vds/Ids) of tera (T) Ω or more can be realized as an example in the subthreshold region as illustrated in FIG. 15C.

On the other hand, the electron mobility μn and the threshold voltage Vth of the NMOS transistor have temperature dependence even in the subthreshold region. The electron mobility μn considering the temperature dependence is expressed as Equation (8). Based on Equations (8) and (17), the drain current Ids reflecting both the temperature dependence of the electron mobility μn and the temperature dependence of the threshold voltage Vth in the subthreshold region is expressed as Equation (22). The temperature dependence of the threshold voltage Vth is contained in Vt (=q/kT) in Equation (22).

[Math. 12]

$$I_{ds} = \mu_{n\_} T_0 \cdot (T/T_0)^{\alpha\mu} \cdot C_{ox} \frac{W}{L} (\eta-1) V_t^2 e^{\frac{V_{gs}-V_{th}}{\eta V_t}} \left(1 - e^{-\frac{V_{ds}}{V_t}}\right) \quad \text{Equation (22)}$$

Figure 16A:
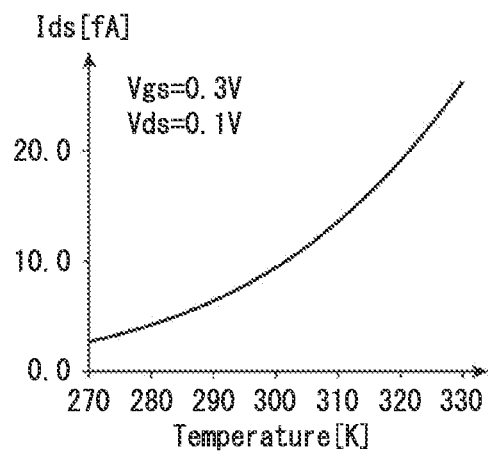
FIG. 16A is a graph illustrating temperature dependence of drain current of a general NMOS transistor in the subthreshold region.
Figure 16B:
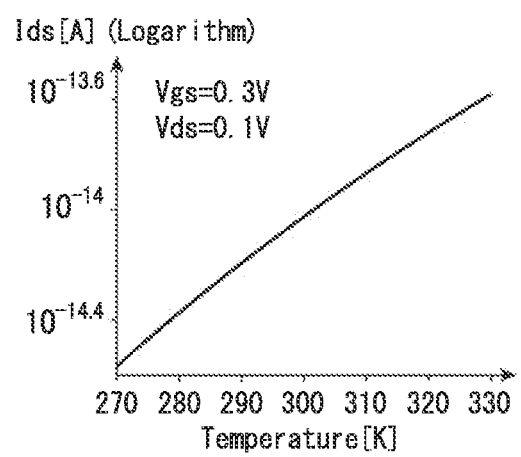
FIG. 16B is a semi-log graph illustrating temperature dependence of drain current of the general NMOS transistor in the subthreshold region.

FIG. 16A is a graph illustrating the temperature dependence of the drain current Ids of the NMOS transistor in the subthreshold region, expressed as Equation (22). Temperature [K] is on the horizontal axis, and drain current Ids [fA] is on the vertical axis. FIG. 16B is a semi-logarithmic graph with the vertical axis of FIG. 16A on a logarithmic scale. Temperature [K] is on the horizontal axis, and drain current Ids [A] is on the vertical axis on a logarithmic scale. FIGS. 16A and 16B illustrate simulation results using standard circuit parameters.

As illustrated in FIG. 16A, the drain current Ids reflecting both the temperature dependence of the electron mobility μn and the temperature dependence of the threshold voltage Vth increases exponentially with rising temperature T. Therefore, the logarithm $\log_{10}$ Ids of the drain current Ids is substantially proportional to the temperature T as illustrated in FIG. 16B.

On the other hand, the drain current Ids increases exponentially with increasing gate-source voltage Vgs as illustrated in FIG. 15A. The logarithm $\log_{10}$ Ids of the drain current Ids is therefore proportional to the gate-source voltage Vgs as illustrated in FIG. 15B.

Therefore, the gate-source voltage Vgs is linearly lowered according to the drain current Ids that exponentially increases with rising temperature, and the drain current Ids is exponentially reduced, thereby enabling suppression of the temperature dependence of the drain current Ids. As a result, the temperature dependence of the NMOS transistor as the MOS resistance can be corrected in the subthreshold region.

As described above, the control voltage Vgs to be applied between the gate and source of the transistor TN can be corrected in the subthreshold region according to the linear function (correction voltage Vc) of Equation (2). In this case as well, the correction factor β (Rp) corresponding to the resistance value Rp without temperature dependence or the correction factor β (Rd) corresponding to the target resistance value Rd without temperature dependence are determined by the procedure similar to the procedures described with reference to FIGS. 11A to 13C.

Note that the simulation conditions using standard circuit parameters in FIGS. 14A to 16B are μn·Cox=170.0 μA/V², μn_T0·Cox=170.0 μA/V², W=0.6 μm, L=60.0 μm, η=1/0.7, αμ=−1.5, η=1/0.7, k=1.381×10⁻²³ J/K, q=1.602×10⁻¹⁹ C, Vth=0.7V, and T0=300K. In FIGS. 14A to 15C, T=310K.

Here, when the correction factor β for correcting the temperature dependence of the transistor TN is reflected in Equation (22), the drain current Ids of the transistor TN in the subthreshold region is expressed as Equation (23).

[Math. 13]

$$I_{ds} = \mu_{n\_} T_0 \cdot (T/T_0)^{\alpha\mu} \cdot C_{ox} \frac{W}{L} (\eta-1) V_t^2 e^{\frac{V_{gs0}-\beta(T-T_1)-V_{th}}{\eta V_t}} \left(1 - e^{-\frac{V_{ds}}{V_t}}\right) \quad \text{Equation (23)}$$

Figure 17A:
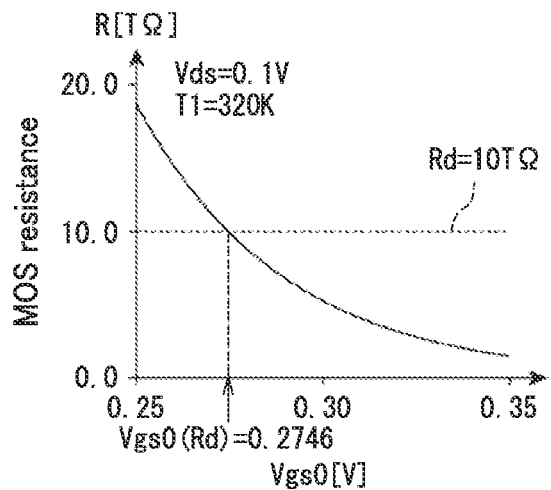
FIG. 17A is a graph illustrating the relationship between reference voltage and resistance value of the transistor at first temperature in the subthreshold region in the first embodiment.
Figure 17B:
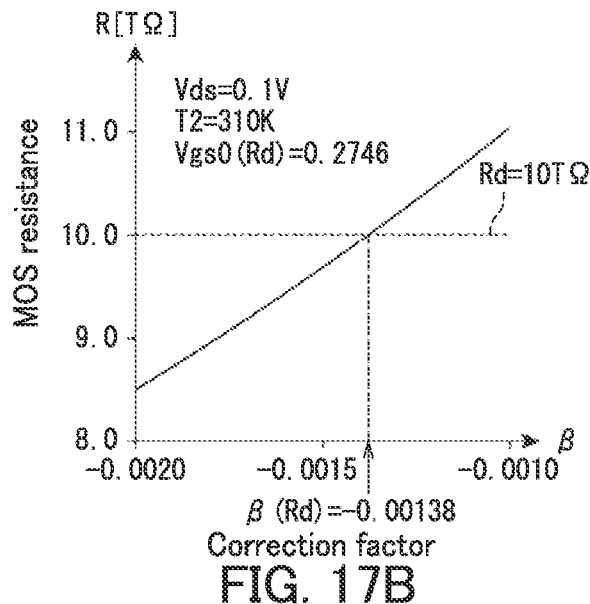
FIG. 17B is a graph illustrating the relationship between correction factor and resistance value of the transistor at second temperature in the subthreshold region in the first embodiment.

Next, an example of a correction factor (β) determining method in the subthreshold region will be described with reference to FIGS. 17A to 17C. FIG. 17A is a graph illustrating the relationship between the resistance value R of the transistor TN and the reference voltage Vgs0 at the first temperature T1 (=320K). FIG. 17B is a graph illustrating the relationship between the resistance value R of the transistor TN and the correction factor β at the second temperature T2 (=310K). In FIG. 17A, voltage value [V] is on the horizontal axis. In FIG. 17B, correction factor β is on the horizontal axis. In FIGS. 17A and 17B, resistance value R [TΩ] is on the vertical axis. The correction factor β is determined by (Procedure 1) and (Procedure 2) described below.

(Procedure 1)

As illustrated in FIG. 17A, the reference voltage Vgs0 (Rd) when the resistance value R corresponds to the target resistance value Rd (10 TΩ in the example of FIG. 17A) is determined, at the first temperature T1 where the correction voltage Vc becomes zero, by measuring the resistance value R of the resistance device 100 while varying the voltage value of the reference voltage Vgs0. Note that the correction factor β may be any value because the correction voltage Vc is zero at the first temperature T1.

(Procedure 2)

As illustrated in FIG. 17B, the reference voltage Vgs0 in the resistance device 100 is set to the reference voltage Vgs0 (Rd) determined in (Procedure 1). The correction factor β(Rd) when the resistance value R corresponds to the target resistance value Rd (10 TΩ in the example of FIG. 17B) is determined, at the second temperature T2, by measuring the resistance value R while varying the value of the correction factor β.

Here, the resistance values R in FIGS. 17A and 17B are derived from the simulation results based on Equations (21) and (23). Simulation conditions using standard circuit parameters are μn_T0·Cox=170.0 μA/V², W=0.6 μm, L=60.0 μm, αμ=−1.5, η=1/0.7, k=1.381×10⁻²³ J/K, q=1.602×10⁻¹⁹ C, Vth=0.7V, and T0=300K. Further, in FIG. 17A, T=T1=320K. In FIG. 17B, T=T2=310K.

In FIGS. 17A and 17B, Vgs0 (Rd)=0.2746V and β (Rd)=−0.00138.

Figure 17C:
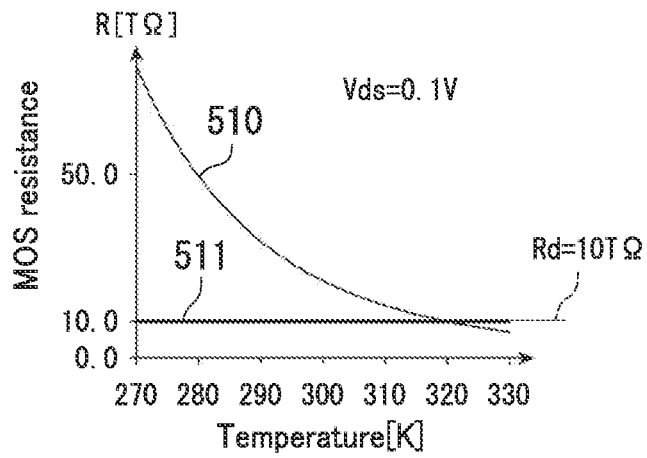
FIG. 17C is a graph illustrating the effect of temperature correction to temperature dependence of resistance value of the transistor in the subthreshold region in the first embodiment.

FIG. 17C is a graph illustrating the effect of temperature correction to the temperature dependence of the resistance value R of the transistor TN. The curve 510 represents values when the temperature correction is not performed, and the curve 511 represents values when the temperature correction is performed. Temperature T [K] is on the horizontal axis, and resistance value R [TΩ] is on the vertical axis. In the case of no temperature correction, the correction factor β in Equation (23) was set to zero, the reference voltage Vgs0 was set to 0.2746V as Vgs0 (Rd) obtained in (Procedure 1), the resistance value R was calculated from Equation (21), and the curve 510 was plotted. As is clear from the curve 510, the resistance value R depends strongly on temperature when the correction is not performed.

On the other hand, in the case of performance of temperature correction, the correction factor β in Equation (23) was set to −0.00138 as β (Rd) obtained in (Procedure 2), the resistance value R was calculated from Equation (23), and the curve 511 was plotted. As is clear from the curve 511, the resistance value R is substantially constant, and has a value Rd. That is, the correction based on the correction factor β (Rd) enables strong suppression of the temperature dependence of the resistance value R of the transistor TN.

As described above with reference to FIG. 17C, it has been confirmed that in the subthreshold region (Vgs<Vth), the temperature correction to the drain current Ids and the resistance value R (MOS resistance) can be appropriately performed based on the correction factor β (Rd). That is, the temperature correction to the gate-source voltage can be performed in the entire range of Vgs<Vth (subthreshold region) and Vgs>Vth ("Vgs>Vth" region). In addition, the temperature correction to the drain-source voltage can be performed in the entire range from the region (linear region) where the drain current Ids of the transistor TN can be linearly approximated to the region (saturation region) where it is saturated at a constant value.

Next, an example of a method for measuring the resistance value R (for example, FIGS. 11A, 12B, 13A·13B, 17A, 17B) of the transistor TN when the reference voltage Vgs0 and the correction factor 3 are determined will be described with reference to FIGS. 18A and 18B. Note that in FIGS. 18A and 18B, the temperature detector 13 is omitted for the sake of simplification of the drawings.

Figure 18A:
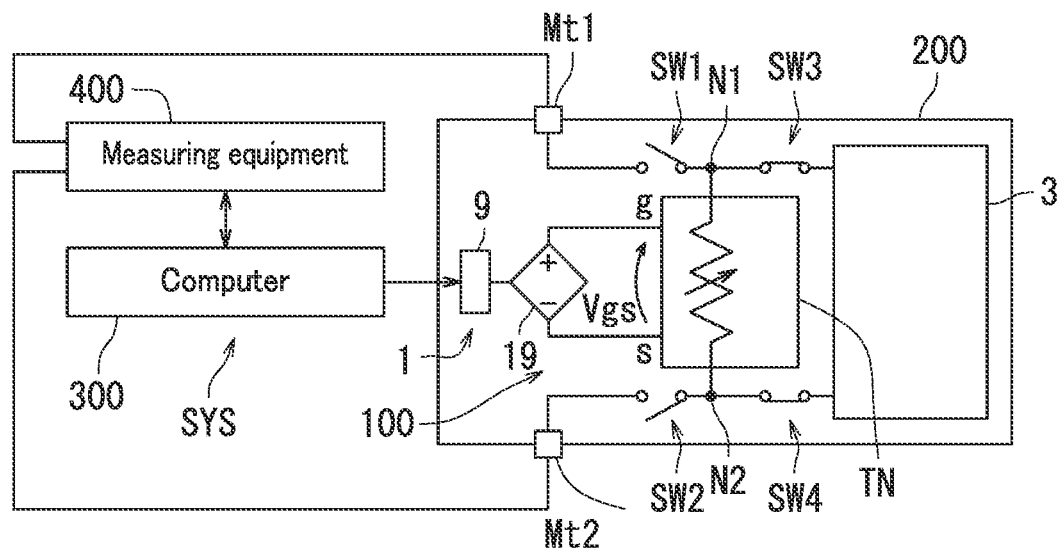
FIG. 18A illustrates a first example of a method for measuring a resistance value of the transistor in the first embodiment.

FIG. 18A illustrates a first example of a measuring method of the resistance value R of the transistor TN in the first embodiment. As illustrated in FIG. 18A, the resistance device 100 is mounted on an electronic circuit device 200. The electronic circuit device 200 is, for example an integrated circuit device.

The electronic circuit device 200 includes a resistance device 100, switches SW1 to SW4, an electronic circuit 3, a monitor terminal Mt1, and a monitor terminal Mt2. A transistor TN of the resistance device 100 is connected to the electronic circuit 3 via the switches SW3 and SW4.

The switches SW1 and SW3 are connected in series between the monitor terminal Mt1 and the electronic circuit 3. A first end (drain terminal) of the transistor TN in the resistance device 100 is connected to a node N1 between the switch SW1 and the switch SW3. The switches SW2 and SW4 are connected in series between the monitor terminal Mt2 and the electronic circuit 3. A second end (source terminal) of the transistor TN in the resistance device 100 is connected to a node N2 between the switch SW2 and the switch SW4.

When the resistance value R of the transistor TN is measured and the reference voltage Vgs0 and the correction factor 3 are determined, the switches SW1 and SW2 connect the transistor TN to the monitor terminals Mt1 and Mt2. The switches SW3 and SW4 also disconnect the transistor TN from the electronic circuit 3.

When the electronic circuit device 200 is operated alone, the reference voltage Vgs0 and the correction factor β which have been determined are set to a control voltage applying section 9, and the switches SW1 and SW2 disconnect the transistor TN and the electronic circuit 3 from the monitor terminals Mt1 and Mt2. The switches SW3 and SW4 also connect the transistor TN to the electronic circuit 3.

A measurement system SYS measures the resistance value R of the transistor TN and processes the measurement data. The measurement system SYS includes a computer 300 and a measuring equipment 400.

The measuring equipment 400 is connected to the monitor terminals Mt1 and Mt2. The measuring equipment 400 applies a voltage Vds to both ends of a resistance of the transistor TN via the monitor terminals Mt1 and Mt2 and measures a current Ids flowing through the resistor, thereby measuring the resistance value R of the transistor TN.

The computer 300 sets the voltage value of the reference voltage Vgs0 to a reference voltage generator 11 of the control voltage applying section 9. When searching for the reference voltage Vgs0 (Rd) with respect to the target resistance value Rd, the computer 300 varies the voltage value of the reference voltage Vgs0 to be set to the reference voltage generator 11.

The computer 300 sets the value of the correction factor β for a correction voltage generator 15 of the control voltage applying section 9. When searching for the correction factor β (Rd) with respect to the target resistance value Rd, the computer 300 varies the value of the correction factor β to be set to the correction voltage generator 15.

The computer 300 controls the measuring equipment 400. The computer 300 then acquires measurement data on the resistance value R of the transistor TN from the measuring equipment 400. The computer 300 processes the measurement data to determine the correction factor 3 (Rd) and the reference voltage Vgs0 (Rd) with respect to the target resistance value Rd.

As described above with reference to FIG. 18A, in the first example of the measuring method, the transistor TN is connected to the monitor terminals Mt1 and Mt2, and the resistance value R of the transistor TN is directly measured. Therefore, the resistance value R can be measured with high precision. In particular, the first example of the measuring method is effective in the case where connecting the monitor terminals Mt1 and Mt2 to the transistor TN and connecting the switches SW3 and SW4 between the transistor TN and the electronic circuit 3 do not affect the characteristics of the transistor TN and the operation of the electronic circuit 3.

Figure 18B:
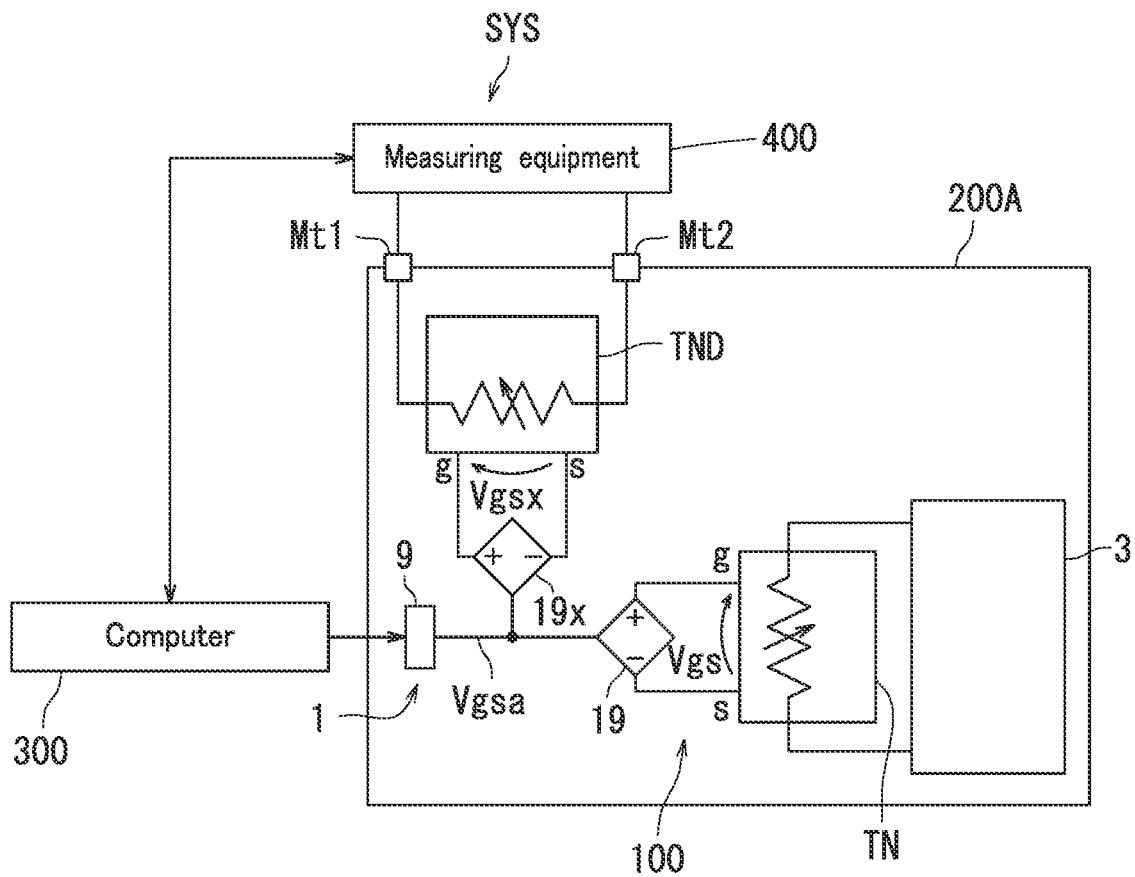
FIG. 18B illustrates a second example of a method for measuring a resistance value of the transistor in the first embodiment.

FIG. 18B illustrates a second example of the measuring method of the resistance value R of the transistor TN in the first embodiment. Hereinafter, components of the second example different from those of the first example will be mainly described.

As illustrated in FIG. 18B, a resistance device 100 is mounted on an electronic circuit device 200A. The electronic circuit device 200A is, for example an integrated circuit device.

The electronic circuit device 200A includes the resistance device 100, an electronic circuit 3, a monitor terminal Mt1, a monitor terminal Mt2, a voltage-controlled voltage source 19x, and a transistor TND.

The configuration of the transistor TND is the same as the configuration of the transistor TN. The transistor TND is placed in close proximity to the transistor TN. The second example measures the resistance value (hereinafter referred to as a "resistance value Rx") of the transistor TND having the same configuration as the transistor TN, and estimates that the resistance value Rx would be the resistance value R of the transistor TN.

A first terminal (drain terminal) of the transistor TND is connected to the monitor terminal Mt1, and a second terminal (source terminal) is connected to the monitor terminal Mt2. On the other hand, a transistor TN is connected to the electronic circuit 3.

The configuration of the voltage-controlled voltage source 19x is the same as the configuration of the voltage-controlled voltage source 19. The voltage-controlled voltage source 19x is connected to a control voltage applying section 9. Therefore, the voltage-controlled voltage source 19x generates, based on a control voltage Vgsa, a control voltage (hereinafter, referred to as a "measurement control voltage Vgsx") having the same voltage value as a control voltage Vgs generated by the voltage-controlled voltage source 19. The voltage-controlled voltage source 19x then applies the measurement control voltage Vgsx between the gate and source of the transistor TND.

The measuring equipment 400 applies a voltage Vds between both ends of a resistor formed by the transistor TND via the monitor terminals Mt1 and Mt2 and measures a drain current flowing through the resistor, thereby measuring the resistance value Rx of the transistor TND. The computer 300 then acquires measurement data on the resistance value Rx of the transistor TND from the measuring equipment 400. The computer 300 further processes the measurement data to determine a reference voltage Vgs0 (Rd) and a correction factor β (Rd) with respect to a target resistance value Rd. That is, the computer 300 estimates that the resistance value Rx of the transistor TND is the resistance value R of the transistor TN, and determines the reference voltage Vgs0 (Rd) and the correction factor β (Rd).

As described above with reference to FIG. 18B, the second example of the measurement method measures the resistance value Rx of the transistor TND having the same configuration as the transistor TN connected to the electronic circuit 3, thereby indirectly measuring the resistance value R of the transistor TN. It is therefore possible to prevent the monitor terminals Mt1 and Mt2 from affecting the characteristics of the transistor TN and the operation of the electronic circuit 3.

In the second example of the measurement method, it is preferable to arrange the transistor TND as close to the transistor TN as possible in particular because the variation in characteristics between the transistor TND and the transistor TN can be suppressed, and the degree of coincidence between the resistance value Rx and the resistance value R is further improved.

Here, in FIGS. 18A and 18B, the configuration of the electronic circuit 3 is not particularly limited as long as the transistor TN is connected to the electronic circuit 3. The electronic circuit 3 may include, for example at least one of devices that include a transistor, a diode, a capacitor, an inductor, and a resistor.

So far, in order to correct the temperature of the resistance value R of the transistor TN in the resistance device 100, the method of measuring the resistance value R of the target transistor TN has been described as an example. It is however possible to correct the temperature of the resistance value R of the transistor TN even in a physical quantity other than the resistance value R. In other words, it is possible to determine the correction factor 3 and the reference voltage Vgs0 for temperature correction by using the physical quantity (hereinafter referred to as a "physical quantity G") that is measurable from an electronic circuit including the resistance device 100 that performs the temperature correction. Hereinafter, the physical quantity G that is measurable from the electronic circuit may be described as a "physical quantity G of the electronic circuit".

Figure 19A:
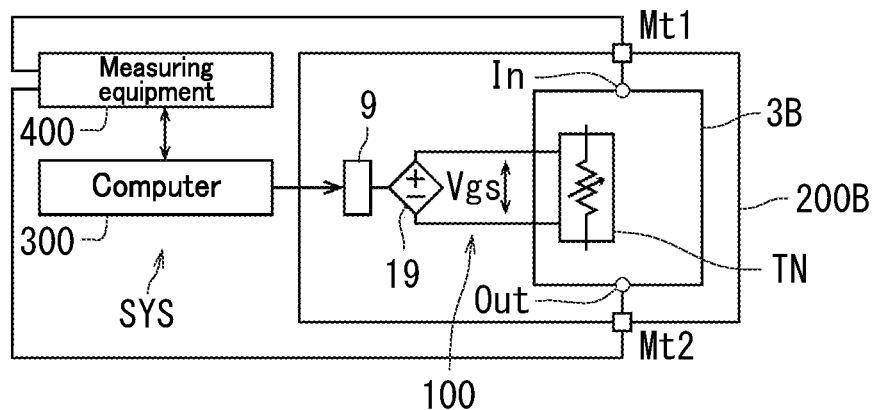
FIG. 19A is a diagram illustrating an electronic circuit device including the resistance device in the first embodiment.

It is described with reference to FIG. 19A that temperature correction can be performed by using a physical quantity G measurable from an electronic circuit including a resistance device 100 to determine a reference voltage Vgs0 and a correction factor β. FIG. 19A is a diagram illustrating an electronic circuit device 200B including the resistance device 100. Note that in FIG. 19A, a temperature detector 13 is omitted for the sake of simplification of the drawings.

As illustrated in FIG. 19A, the electronic circuit device 200B includes an electronic circuit 3B and the resistance device 100. A transistor TN (MOS resistance MR) of the resistance device 100 is built in the electronic circuit 3B as a circuit element of the electronic circuit 3B. An input terminal In and an output terminal Out of the electronic circuit 3B are connected to a terminal Mt1 and a terminal Mt2 of the electronic circuit device 200B, respectively. Here, FIG. 19A illustrates one input terminal In and one output terminal Out in the electronic circuit 3B, and also illustrates one terminal Mt1 and one terminal Mt2 in the electronic circuit device 200B. However, the number of terminals is not particularly limited. A measuring equipment 400 and the electronic circuit 3B may be connected with terminals. The number of terminals connecting a measuring equipment 400 and the electronic circuit 3B may be any number necessary for measuring the physical quantity G of the electronic circuit 3B.

A measuring system SYS includes a computer 300 and the measuring equipment 400. The measuring equipment 400 is connected to the input and output terminals In and Out of the electronic circuit 3B via the terminals Mt1 and Mt2, and measures the physical quantity G of the electronic circuit 3B. The computer 300 controls the measuring equipment 400 and acquires measurement data from the measuring equipment 400.

The physical quantity G that is measurable by the measuring equipment 400 from the electronic circuit 3B including the transistor TN (MOS resistance MR) of the resistance device 100 can be generalized and expressed as a function of the resistance value R of the transistor TN as in Equation (24). Specifically, the resistance value R can be generalized and expressed as a function of temperature T, reference voltage Vgs0, and correction factor β. Therefore, the physical quantity G expressed as the function of the resistance value R can also be generalized and expressed as the function of temperature T, reference voltage Vgs0, and correction factor β.

$$G=G(R)=G(R(T,Vgs0,\beta))$$   Equation (24):

The temperature dependence of the physical quantity G, in Equation (24), which is the function of the resistance value R of the transistor TN is also corrected by temperature correction to the resistance value R of the transistor TN in the resistance device 100. In the electronic circuit 3B, the temperature dependence of the transistor TN in the resistance device 100 is dominant. For example, when the temperature dependence of other circuit elements constituting the electronic circuit 3B can be sufficiently ignored, if the temperature correction to the resistance value R of the transistor TN is properly performed, the temperature dependence of the physical quantity G, in Equation (24), which is the function of the resistance value R of the transistor TN is also effectively corrected.

Figure 19B:
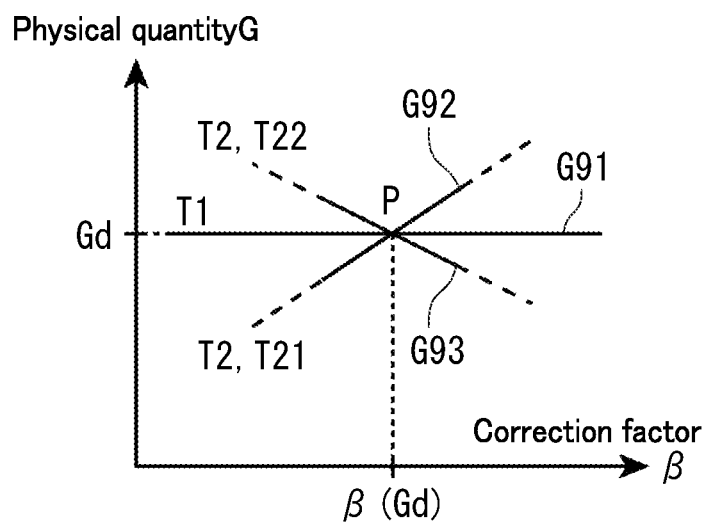
FIG. 19B is a graph generalizing the relationship between correction factor and physical quantity measurable from the electronic circuit in the first embodiment.

FIG. 19B is a graph generalizing the relationship between the physical quantity G measurable from the electronic circuit 3B and the correction factor β of the resistance value R of the transistor TN in the resistance device 100 included in the electronic circuit 3B. The curve G91 is a G-β curve representing the physical quantity G with respect to the correction factor β at a first temperature T1 at which a correction voltage Vc of the transistor TN becomes zero. Here, two second temperatures T2 different from the first temperature T1 are introduced. One of the two second temperatures T2 is described as a second temperature T21, and the other of the two second temperatures T2 is described as a second temperature T22. The second temperature T21 differs from the second temperature T22. The curve G92 and the curve G93 are a G-β curve at the second temperature T21 and a G-β curve at the second temperature T22, respectively. As described above, each G-β curve illustrates the relationship between the physical quantity G and the correction factor β.

In the electronic circuit 3B, for example, when only the transistor TN of the resistance device 100 is included as the circuit element with temperature dependence, if the temperature dependence of the resistance value R of the transistor TN is appropriately corrected, the temperature dependence of the physical quantity G of the electronic circuit 3B is also eliminated. That is, in FIG. 19B, when the temperature dependence of the resistance value R of the transistor TN is appropriately corrected, the physical quantity G at the first temperature T1 where the correction voltage Vc is zero coincides with the physical quantity G at the second temperature T21. In addition, the physical quantity G at the first temperature T1 where the correction voltage Vc is zero coincides with the physical quantity G at the second temperature T22. In other words, the intersection of the curve G91 at the first temperature T1, the curve G92 at the second temperature T21 and the intersection of the curve G91 at the first temperature T1, and the curve G93 at the second temperature T22 coincide with each other at an intersection P. Moreover, the intersection of the curve G91 at the first temperature T1 and an arbitrary G-β curve at an arbitrary temperature different from the first temperature T1 coincides with the intersection P that is one point. That is, the curve G91 at the first temperature T1 and the two or more G-β curves corresponding to two or more arbitrary temperatures different from the first temperature T1 intersect at the intersection P that is one point. The correction factor β (Gd) and the physical quantity Gd without temperature dependence are uniquely identified by the intersection P of the curve G91 at the first temperature T1 where the correction voltage Vc is zero and the G-β curve (for example, curve G92) at one temperature (for example, second temperature T21) different from the first temperature T1.

As illustrated in FIG. 19B, the correction voltage Vc becomes zero at the first temperature T1. Therefore, the resistance value R of the transistor TN is substantially constant regardless of the correction factor β, and the physical quantity G, in Equation (24), of the electronic circuit 3B is also substantially constant. The reference voltage Vgs0 and the correction factor β can therefore be uniquely identified by searching for the reference voltage Vgs0 (Gd) that is a target physical quantity Gd at the first temperature T1, setting the reference voltage Vgs0 of the resistance device 100 to Vgs0 (Gd), and searching for the correction factor β (Gd) for the target physical quantity Gd at the second temperature T2 different from the first temperature T1.

The method of determining the reference voltage Vgs0 and the correction factor β has been described with reference to FIGS. 11 to 13 and 17. In this method, the "resistance value R" of the transistor TN in the resistance device 100 is replaced with the "physical quantity G" of the electronic circuit 3B including the resistance device 100. Further, the "target resistance value Rd" is replaced with the "target physical quantity Gd". In this case, the reference voltage Vgs0 and the correction factor β can be determined for the "physical quantity G" by the same procedure as for the "resistance value R". In addition, in the method for determining the reference voltage Vgs0 and the correction factor β described with reference to FIGS. 11 to 13 and 17, the "resistance value" is replaced with the "physical quantity" and the "R-β curve" is replaced with the "G-β curve".

When the other circuit elements constituting the electronic circuit 3B, which are different from the transistor TN of the resistance device 100, have temperature dependence, the curves G91, G92 and G93 do not intersect at one-point P in FIG. 19B. That is, multiple intersections exist. For example, the intersection of the curves G91 and G92, the intersection of the curves G91 and G93, and the intersection of the curves G92 and G93 exist. In other words, multiple intersections of G-β curves exist at any two different temperatures. However, if the temperature dependence of the other circuit elements is sufficiently small compared to the temperature dependence of the transistor TN of the resistance device 100, multiple intersections of G-β curves at any two different temperatures will have close values. The temperature dependence of the physical quantity G of the electronic circuit 3B can therefore be suppressed by, for example defining the average value or the median value of correction factors R determined from the intersections as the final correction factor β to appropriately determine the correction factor β.

Note that the value of the correction factor β (Gd) is a value when the target physical quantity Gd is obtained at the second temperature T2 different from the first temperature T1 based on the reference voltage Vgs0 (Gd) when the target physical quantity Gd for the transistor TN is obtained at the first temperature T1.

Figure 20A:
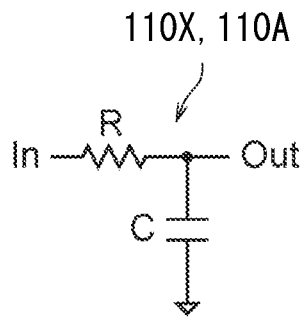
FIG. 20A is a circuit diagram of an integral filter as an RC filter circuit in the first embodiment.
Figure 20B:
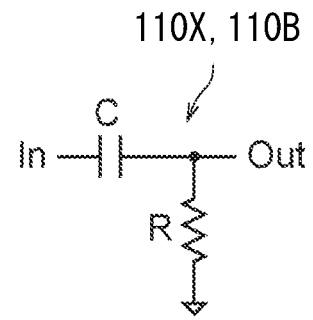
FIG. 20B is a circuit diagram of a differential filter as the RC filter circuit in the first embodiment.

Here, a specific example of the temperature correction method of the electronic circuit 3B including the transistor TN of the resistance device 100 illustrated in FIG. 19A will be described using an RC filter circuit. FIG. 20A is a circuit diagram illustrating an RC integral filter 110A in the first embodiment. FIG. 20B is a circuit diagram illustrating an RC differential filter 110B in the first embodiment. Each of the RC integral filter 110A and the RC differential filter 110B is an example of the RC filter circuit. Hereinafter, the RC integral filter 110A and the RC differential filter 110B may be collectively referred to as an "RC filter circuit 110X".

As illustrated in FIGS. 20A and 20B, the RC filter circuit 110X is one of basic electronic circuits, and includes a resistance element R having a resistance value R and a capacitor C having a capacitance value C. The RC filter circuit 110X includes an input terminal In and an output terminal Out. Note that a voltage input to the input terminal In may be described as an "input voltage In", and a voltage output from the output terminal Out may be described as an "output voltage Out".

A specific circuit example of the electronic circuit 3B in FIG. 19A is the RC integral filter 110A of FIG. 20A or the RC differential filter 110B of FIG. 20B. In other words, the input and output terminals In and Out of each of the RC integral filter 110A and the RC differential filter 110B correspond to the input and output terminals In and Out of the electronic circuit 3B in FIG. 19A, respectively. Further, each resistance element R of the RC integral filter 110A and the RC differential filter 110B corresponds to the transistor TN (MOS resistance MR) of the resistance device 100 in FIG. 19A.

Physical quantities exhibiting the basic characteristics of the RC filter circuit 110X illustrated in FIGS. 20A and 20B include a cutoff frequency fc [Hz]. In the RC integral filter 110A of FIG. 20A, when the frequency of a sinusoidal voltage signal applied to the input terminal In is increased, a circuit gain (=Amplitude of output voltage Out/Amplitude of input voltage In) decreases when the frequency exceeds the cutoff frequency fc. Theoretically, the gain of the circuit at the cutoff frequency fc is 3 dB lower than that when the sine wave having the frequency sufficiently lower than the cutoff frequency fc is input, and is called a high cutoff frequency. In the RC differential filter 110B of FIG. 20B, when the frequency of the sinusoidal voltage signal applied to the input terminal In is reduced, the gain of the circuit decreases when the frequency falls below the cutoff frequency fc. Theoretically, the gain of the circuit at the cutoff frequency fc is 3 dB lower than that when the sine wave having the frequency sufficiently higher than the cutoff frequency fc is input, and is called a low cutoff frequency.

The cutoff frequency fc is common to the RC integral filter 110A and the RC differential filter 110B, and is represented by the resistance value R and the capacitance value C as in Equation (25). When the resistance element R of the RC filter circuit 110X is composed of the MOS resistance by the transistor TN, and the capacitor C of the RC filter circuit 110X is composed of a general parallel plate capacitance, the temperature dependence of the capacitor C is sufficiently lower than that of the MOS resistance. Therefore, regarding the temperature dependence, the cutoff frequency fc can be expressed as a function of the resistance value R having a high temperature dependence. In other words, as can be understood from Equation (25), the cutoff frequency fc is expressed as the reciprocal of the resistance value R (=1/R), and 1/R is multiplied by a constant $1/(2\pi C)$ with sufficiently low temperature dependence.

$$fc=1/(2\pi RC)=fc(R(T,Vgs0,\beta))$$  Equation (25):

Equation (25) expressing the cutoff frequency fc of the RC filter circuit 110X may be a function of temperature T, reference voltage Vgs0, and correction factor β, like Equation (24) generalizing the physical quantity G measurable from the electronic circuit 3B. Therefore, the physical quantity G measurable from the electronic circuit 3B and the cutoff frequency fc of the RC filter circuit 110X are the same as described with reference to Equation (24) and FIG. 19A. That is, the cutoff frequency fc is an example of the physical quantity G measurable from the electronic circuit 3B. Therefore, the reference voltage Vgs0 and the correction factor β at a desired cutoff frequency fd (hereinafter, may be referred to as a "target cutoff frequency fd") can be determined by measuring the cutoff frequency fc. The target cutoff frequency fd corresponds to an example of the "target physical quantity relating to the field-effect transistor". That is, the target cutoff frequency fd is a physical quantity containing the resistance value of the field-effect transistor TN, which is measurable from an electronic circuit (RC filter circuit 110X) including the field-effect transistor TN. The target cutoff frequency fd corresponds to a cutoff frequency fc that is set as the target value.

If the physical quantity on the vertical axis of the graphs of FIGS. 11 to 13 and 17 used in the explanation of the temperature correction procedure are converted into the cutoff frequency fc according to Equation (25), a graph illustrating the procedure of temperature correction by the cutoff frequency fc of the RC filter circuit 110X can be obtained. It can therefore be seen that the correction factor β and the reference voltage Vgs0 at the target cutoff frequency fd can be determined like the procedures described with reference to the graphs of FIGS. 11 to 13 and 17.

For example, if the value on the vertical axis in the graphs of, for example, FIGS. 11A, 12A, and 12B are changed to the reciprocal (1/R) of the resistance value R, the shape of the curve varies, whereas the value of the correction factor β(Rp) or β(Rr) at the intersection of the two curves at two different temperatures does not vary. In this case, the value of 1/R on the vertical axis at the intersection of the graph is 1/Rp or 1/Rr. In this case, even if the physical quantity on the vertical axis of the graph is converted to the cutoff frequency fc by multiplying 1/R by the constant $1/(2\pi C)$, the value of the correction factor β(Rp) or β(Rr) at the intersection of the two curves at two different temperatures does not change. The values of the cutoff frequency fc on the vertical axis at the intersection in the graphs is $1/(2\pi C \times Rp)$ or $1/(2\pi C \times Rr)$. $1/(2\pi C \times Rp)$ or $1/(2\pi C \times Rr)$ is a cutoff frequency without temperature dependence.

The reference voltage Vgs0 (fd) and the correction factor β (fd) at the target cutoff frequency fd without temperature dependence can be determined with respect to the cutoff frequency fc expressed as the reciprocal of the resistance value R by the procedures similar to the procedures described with reference to FIGS. 11 and 12.

For example, the physical quantity on the vertical axis in the graphs of FIGS. 13A, 13B, 17A, and 17B are converted into the cutoff frequency fc by Equation (25), whereby the reference voltage Vgs0 (fd) and the correction factor β (fd) at the target cutoff frequency fd without temperature dependence can be determined by the procedures described with reference to FIGS. 13A, 13B, 17A, and 17B.

As described above, the reference voltage Vgs0 (fd) and the correction factor β (fd) at the target cutoff frequency fd are determined. In this case, the method of determining the reference voltage Vgs0 and the correction factor β has been described with reference to FIGS. 11 to 13 and 17. In this method, the "resistance value R" of the transistor TN in the resistance device 100 is replaced with the "cutoff frequency fd" of the electronic circuit 3B including the transistor TN. Further, the "target resistance value Rd" is replaced with the "target cutoff frequency fd". Even in the case of the "cutoff frequency fd", the reference voltage Vgs0 and the correction factor β can be determined by the same procedures as in the case of the "resistance value R". In addition, in the method for determining the reference voltage Vgs0 and the correction factor β described with reference to FIGS. 11 to 13 and 17, the "resistance value" is replaced with the "cutoff frequency" and the "R-β curve" is replaced with the "fc-β curve". The fc-β curve represents the relationship between the cutoff frequency fc and the correction factor β.

An example of a method for measuring the cutoff frequency fc of the RC filter circuit 110X will be described with reference to FIG. 19A. The measuring equipment 400 of the measuring system SYS applies a sinusoidal voltage signal to the electronic circuit 3B, that is, the input terminal In of the RC filter circuit 110X of FIG. 20A or FIG. 20B via the terminal Mt1. At this time, the measuring equipment 400 of the measuring system SYS measures, via the terminal Mt2, the output waveform from the electronic circuit 3B, that is, the output terminal Out of the RC filter circuit 110X. The measuring equipment 400 repeats such measurement while varying the frequency of the sine wave, and measures (calculates) the cutoff frequency fc based on the relationship between the gain (=amplitude of output voltage Out/amplitude of input voltage In) of the RC filter circuit 110X and the input frequency.

The computer 300 varies the voltage value of the reference voltage Vgs0 to be set in the reference voltage generator 11 based on the measurement purpose of the cutoff frequency fc. The computer 300 also varies the value of the correction factor β to be set in the correction voltage generator 15 based on the measurement purpose of the cutoff frequency fc. Further, the computer 300 acquires measurement data from the measuring equipment 400 for calculating the cutoff frequency fc of the electronic circuit 3B, that is, the RC filter circuit 110X of FIG. 20A or FIG. 20B. The computer 300 then processes the measurement data to determine the reference voltage Vgs0 and the correction factor R.

Here, the RC filter circuit 110X in FIG. 20 is used and described as the most basic filter circuit and a specific example of the temperature correction method of the electronic circuit 3B including the transistor TN of the resistance device 100 in FIG. 19A. However, the configuration of the filter circuit is not particularly limited. For example, the temperature correction can be similarly performed by an active filter circuit 110C including an operational amplifier 90 in FIG. 21.

Figure 21:
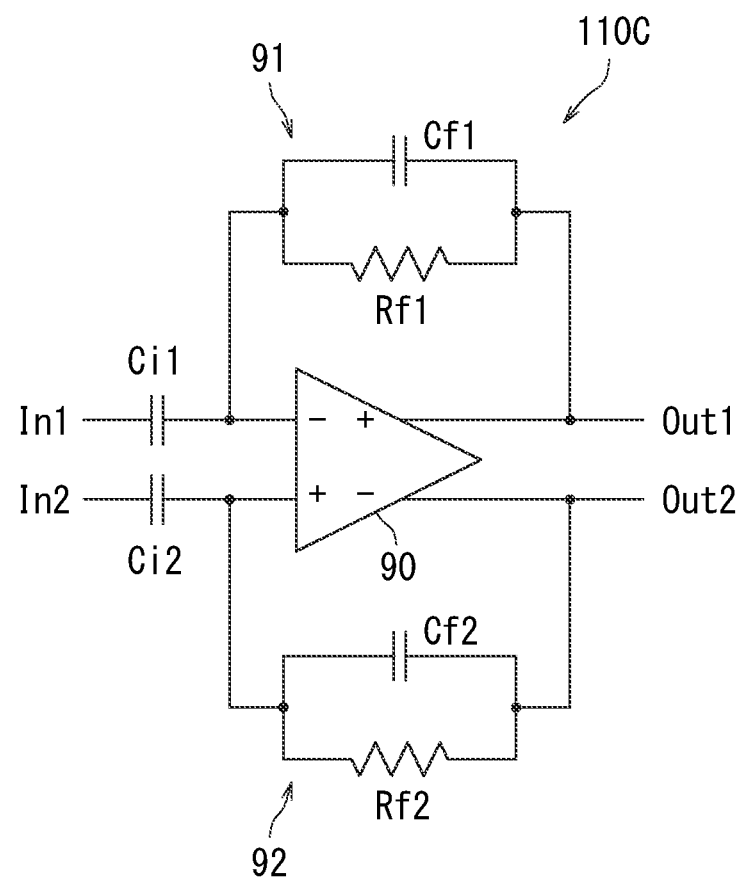
FIG. 21 is a circuit diagram of an active filter circuit in the first embodiment.

FIG. 21 illustrates an example of the active filter circuit 110C in the first embodiment. As illustrated in FIG. 21, the active filter circuit 110C includes the operational amplifier 90, input capacitors Ci1 and Ci2, feedback capacitors Cf1 and Cf2, and feedback resistors Rf1 and Rf2. Each of the feedback resistors Rf1 and Rf2 is composed of a transistor TN (MOS resistance MR) in a resistance device 100. As described above, the electronic circuit 3B in FIG. 19A may include two or more transistors TN (MOS resistance MR).

The example of FIG. 21 has a fully differential configuration with two inputs and two outputs. Input terminals In1 and In2 correspond to the input terminal In of the electronic circuit 3B in FIG. 19A. Output terminals Out1 and Out2 correspond to the output terminal Out of the electronic circuit 3B in FIG. 19A.

The operational amplifier 90 has a fully differential configuration, and inputs differential type voltage signals In1 and In2 via the input capacitors Cin1 and Cin2, and outputs differential type voltage signals Out1 and Out2.

A first feedback circuit 91 composed of the feedback capacitor Cf1 and the feedback resistor Rf1 is connected in parallel between an inverting input terminal and a positive output terminal of the operational amplifier 90.

A second feedback circuit 92 composed of the feedback capacitor Cf2 and the feedback resistor Rf2 is connected in parallel between a non-inverting input terminal and a negative output terminal of the operational amplifier 90.

In the case of the active filter circuit 110C having the fully differential configuration in FIG. 21, the circuit parameters on the side of the input and output terminals In1 and Out1 and the circuit parameters on the side of the input and output terminals In2 and Out2 are provided generally with the same numerical values and characteristics as much as possible. Therefore, respective capacitance values of the input capacitors Cin1 and Cin2 are generally set to be equal. Similarly, respective capacitance values of the feedback capacitors Cf1 and Cf2 are generally set to be equal, and respective resistance values of the feedback resistors Rf1 and Rf2 are generally set to be equal.

The active filter circuit 110C of FIG. 21 operates as a differential filter similar to the RC differential filter 110B of FIG. 20B. The cutoff frequency fc of the active filter circuit 110C is determined by the capacitance values of the feedback capacitors Cf1 and Cf2 and the resistance values of the feedback resistors Rf1 and Rf2. The cutoff frequency fc is expressed as Equation (26), where C denotes the capacitance value of the feedback capacitors Cf1 and Cf2, and R denotes the resistance value of the feedback resistors Rf1 and Rf2. Equation (26) corresponds to Equation (25) expressing the cutoff frequency fc of the RC filter circuit 110X of FIGS. 20A and 20B.

$$fc=1/(2\pi RC) \quad \text{Equation (26):}$$

Therefore, Equation (26) expressing the cutoff frequency of the active filter circuit 110C is the same as Equation (24) generalizing the physical quantity G measurable from the electronic circuit 3B, and is expressed as the function of temperature T, reference voltage Vgs0, and correction factor β. Accordingly, the physical quantity G measurable from the electronic circuit 3B and the cutoff frequency fc of the active filter circuit 110C are the same as described with reference to Equation (24) and FIG. 19A. As a result, the reference voltage Vgs0 and the correction factor β at the target cutoff frequency fd can be determined by measuring the cutoff frequency fc.

As described above, as an example in FIG. 19A, the electronic circuit 3B is composed of the RC filter circuit 110X of FIG. 20A or FIG. 20B, or of the active filter circuit 110C of FIG. 21, whose cutoff frequency fc corresponds to the physical quantity to be measured. Even in this case, it can be understood that the temperature correction to the transistor TN in the resistance device 100 included in the RC filter circuit 110X or the active filter circuit 110C can be performed.

It can be understood that the temperature of the transistor TN included in the electronic circuit 3B can be corrected when the physical quantity containing the resistance value R of the transistor TN is measurable from the electronic circuit 3B including the transistor TN in the resistance device 100 by further generalizing. In this case, it is not necessary to directly or indirectly measure the resistance value R of the transistor TN in the resistance device 100 as illustrated in FIGS. 18A and 18B.

Here, in FIG. 19A (in the present specification), the physical quantity relating to the transistor TN, that is, the physical quantity containing the resistance value R of the transistor TN measurable from the electronic circuit 3B including the transistor TN is not limited to the resistance value R and the cutoff frequency fc. Examples of the physical quantity relating to the transistor TN include resistance value, current value, voltage value, frequency, gain, phase, sound, light, pressure, and energy of a circuit element or a circuit included in an electronic circuit 3B. The physical quantity relating to the transistor TN is, for example, a physical quantity obtained by combining two or more of factors that include resistance value, current value, voltage value, frequency, gain, phase, sound, light, pressure, and energy of a circuit element or a circuit included in an electronic circuit 3B. The physical quantity relating to the transistor TN is, for example, frequency distribution, spatial distribution, or time distribution of one or more of factors that include resistance value, current value, voltage value, frequency, gain, phase, sound, light, pressure, and energy of a circuit element or a circuit included in an electronic circuit 3B.

For example, when an electronic circuit 3B includes a current source including a transistor TN, a "current value" as a physical quantity is a current value of the drain current Ids of the transistor TN. For example, when an electronic circuit 3B includes a current source including a transistor TN and an operational amplifier that is activated by the current source, a "physical quantity obtained by a combination of a voltage value and a current value" is slew rate of the operational amplifier. The slew rate is expressed as C×(Vout/Iout), where C denotes a constant, Vout denotes an output voltage of the operational amplifier, and Iout denotes an output current of the operational amplifier.

For example, when an electronic circuit 3B includes a current source including a transistor TN and an oscillator that is activated by the current source, a "frequency" as a physical quantity is an oscillating frequency of the oscillator. For example, when an electronic circuit 3B includes a current source including a transistor TN, an oscillator, and an electromagnetic buzzer connected to the oscillator, a "sound" as a physical quantity is pitch of sound that is output from the electromagnetic buzzer according to the oscillating frequency of the oscillator.

For example, when an electronic circuit 3B includes an operational amplifier and a phase compensation circuit that performs phase compensation of the arithmetic amplifier, "gain frequency distribution" as a physical quantity is a frequency characteristic of the gain of the operational amplifier. The phase compensation circuit includes, for example, a transistor TN and a capacitor. For example, when an electronic circuit 3B includes an operational amplifier and a phase compensation circuit, "phase frequency distribution" as a physical quantity is a phase frequency characteristic of the operational amplifier.

For example, when an electronic circuit 3B includes a current source including a transistor TN and a light emitting element (for example, a light emitting diode) that is activated by the current source, "light" as a physical quantity is a quantity of light emitted from the light emitting element. The quantity of light is denoted by, for example, luminous intensity (Cd), illuminance (lux), or irradiance (W/m$^2$).

For example, when an electronic circuit 3B includes a resistive network, "spatial distribution of voltage values" as a physical quantity is the distribution of output voltages from a plurality of output terminals of the resistive network. Specifically, the resistive network includes a plurality of input terminals to which different input voltages are input, and a plurality of output terminals from which different output voltages are output. The resistive network also includes a plurality of first MOS resistance elements and a plurality of second MOS resistance elements. Respective first terminals of the first MOS resistance elements are a plurality of input terminals, and respective second terminals of the first MOS resistance elements are a plurality of output terminals. On the other hand, the second MOS resistance elements are connected in series. A node between each adjacent second MOS resistance elements is connected with the output terminal, which is the second terminal, of a corresponding first MOS resistance element. Each first MOS resistance element and/or each second MOS resistance element is composed of a transistor TN. Note that, for example a spatial filter such as an image filter can be configured by a resistive network. In this case, the distribution of output voltages from the output terminals of the resistive network represents the spatial filter characteristics.

Next, a correction factor determining method according to the first embodiment of the present invention will be described with reference to FIGS. 22, 23A and 23B. The correction factor determining method determines a correction factor β for correcting a control voltage Vgs to be applied between the gate and source of a field-effect transistor TN as MOS resistance. The correction factor determining method is performed by, for example a measurement system SYS (FIGS. 18A to 19A).

In Equation (27) for the correction factor determining method, control voltage Vgs is denoted by "Vgs", correction voltage Vc is denoted by "Vc", correction factor β is denoted by "β", temperature T as a variable is denoted by "T", and first temperature T1, which is a temperature at which the correction voltage Vc becomes zero, is denoted by "T1". That is, Equation (27) is the same as Equation (1).

$$Vgs=Vgs0+Vc=Vgs0+\beta(T-T1) \quad \text{Equation (27):}$$

Figure 22:
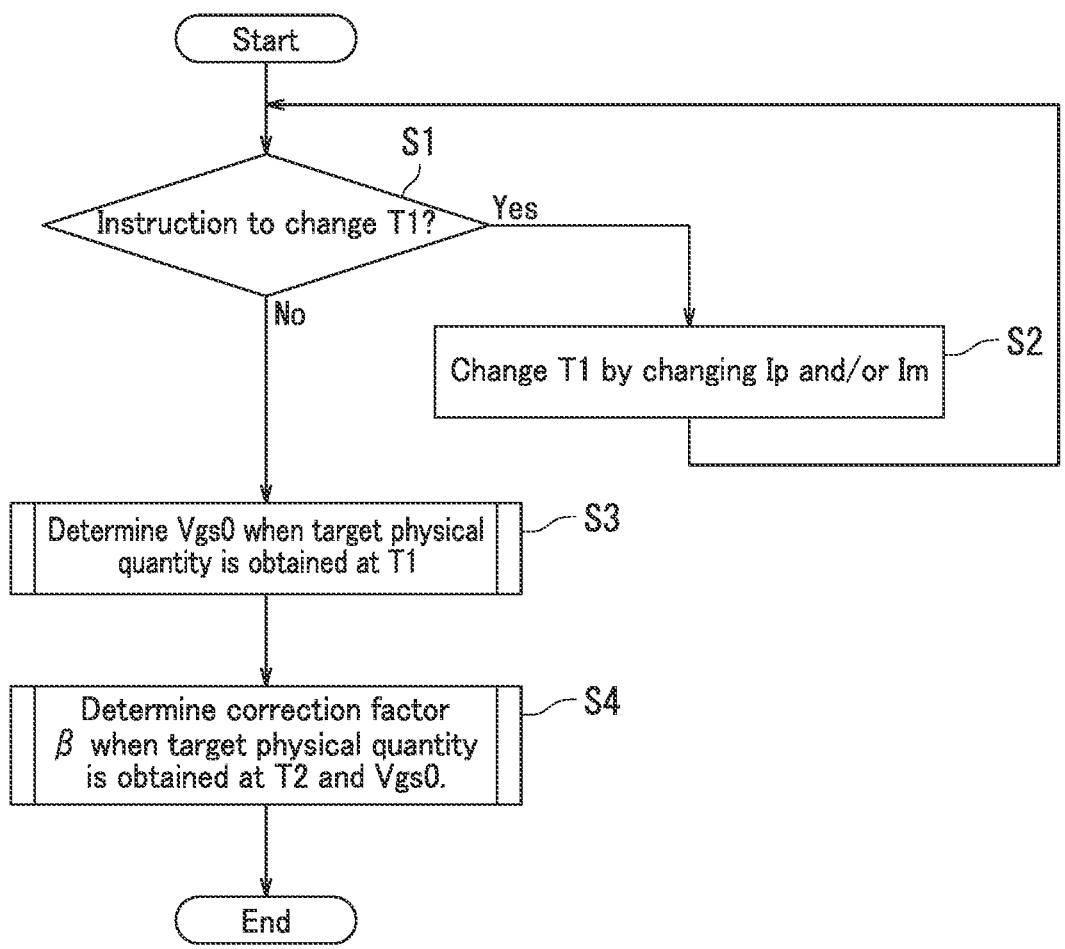
FIG. 22 is a flowchart illustrating a correction factor determining method according to the first embodiment.

FIG. 22 is a flowchart illustrating the correction factor determining method according to the first embodiment. As illustrated in FIG. 22, the correction factor determining method includes Steps S1 to S4.

In Step S1, the measurement system SYS determines whether or not an instruction to vary the first temperature T1 has been accepted.

If a negative determination is made in Step S1 (No), the process proceeds to Step S3.

On the other hand, if a positive determination is made in Step S1 (Yes), the process proceeds to Step S2.

In Step S2, the measurement system SYS controls a temperature detector 13 to vary at least one of current values including the current value of a first current Ip and the current value of a second current Im, thereby varying the temperature T1. The process then proceeds to Step S1.

In Step S3, the measurement system SYS determines a specific voltage value X that is the voltage value of the reference voltage Vgs0 when a target physical quantity Gd relating to the field-effect transistor TN is obtained at the first temperature T1. The target physical quantity Gd represents, for example, a target resistance value Rd of the field-effect transistor TN or a target cutoff frequency fd of a filter circuit (for example, RC filter circuit 110X or active filter circuit 110C) including the field-effect transistor TN. The reference voltage Vgs0 with the specific voltage value X is a reference voltage Vgs0 (Gd). The reference voltage Vgs0 (Gd) is, for example, a reference voltage Vgs0 (Rd) or a reference voltage Vgs0 (fd).

In Step S4, the measurement system SYS determines a specific factor value W that is the value of the correction factor β when the target physical quantity Gd is obtained at a second temperature T2 different from the first temperature T1 and the specific voltage value X of the reference voltage Vgs0. The correction factor β with the specific factor value W is a correction factor β (Gd). The correction factor β (Gd) is for example, a correction factor β (Rd) of a correction factor β (fd).

The correction factor determining method according to the first embodiment has been described above with reference to FIG. 22. In Step S3 by the method, the specific voltage value X of the reference voltage Vgs0 corresponding to the target physical quantity Gd is determined at the first temperature T1 where the correction voltage Vc becomes zero. Subsequently, in Step S4, the specific factor value W of the correction factor β corresponding to the target physical quantity Gd is determined in a state where the reference voltage Vgs0 has the specific voltage value X at the second temperature T2. It is therefore not required to repeatedly obtain a plurality of G-β curves (for example, a plurality of R-β curves or a plurality of fc-β curves) for each different reference voltage Vgs0. This make it possible to uniquely and quickly identify a combination of the specific factor value W of the correction factor β (correction factor β (Gd) (for example, correction factor β (Rd) or correction factor β (fd))) and the target physical quantity Gd without temperature dependence.

Further, in the correction factor determining method according to the first embodiment, the first current Ip and/or the second current Im is varied in Step S2, thereby making it possible to easily vary the first temperature T1 that is the temperature T at which the correction voltage Vc becomes zero.

Figure 23A:
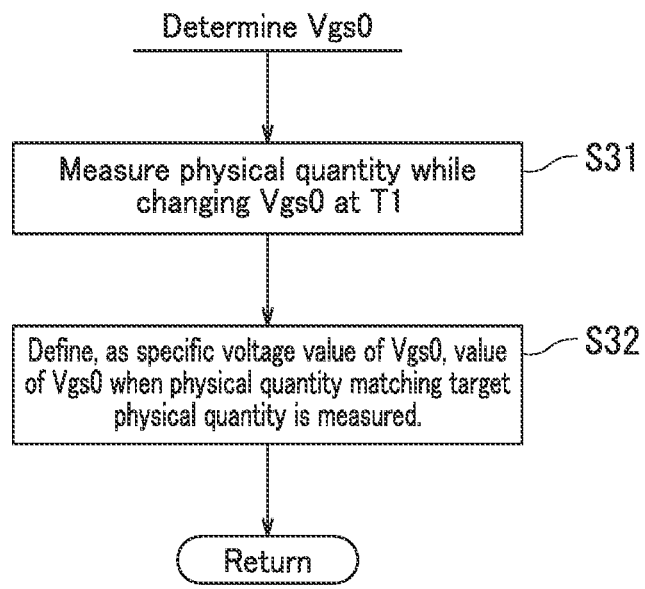
FIG. 23A is a flowchart illustrating Step S3 in FIG. 22.

FIG. 23A is a flowchart illustrating Step S3 in FIG. 22. As illustrated in FIG. 23A, Step S3 (step to determine reference voltage Vgs0) in FIG. 22 includes Steps S31 and S32.

In Step S31, a measuring equipment 400 of the measurement system SYS measures a physical quantity G relating to the field-effect transistor at the first temperature T1 while varying the voltage value of the reference voltage Vgs0.

In Step S32, a computer 300 of the measurement system SYS defines, as the specific voltage value X of the reference voltage Vgs0, the voltage value of the reference voltage Vgs0 when of a plurality of physical quantities G measured while varying the voltage value of the reference voltage Vgs0 in Step S31, the physical quantity G substantially matching the target physical quantity Gd is measured. The first embodiment therefore makes it possible to uniquely and quickly identify the specific voltage value X, which is the voltage value of the reference voltage Vgs0, when the target physical quantity Gd is obtained.

Figure 23B:
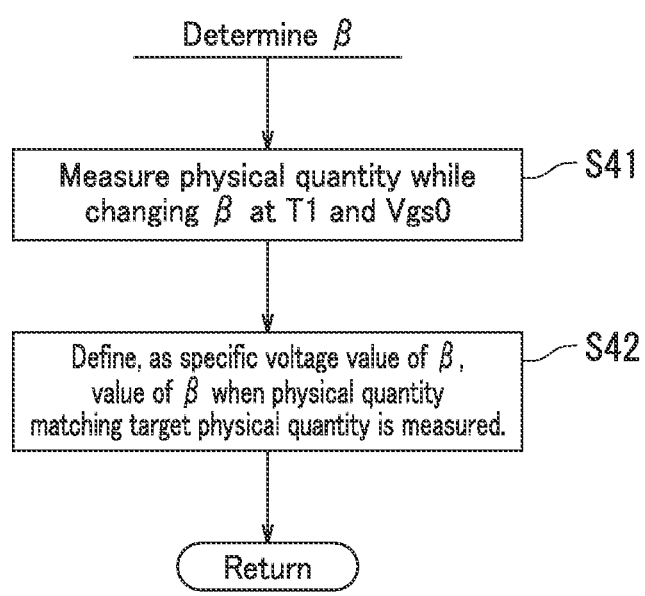
FIG. 23B is a flowchart illustrating Step S4 in FIG. 22.

FIG. 23B is a flowchart illustrating Step S4 in FIG. 22. As illustrated in FIG. 23B, Step S4 (step to determine correction factor β) in FIG. 22 includes Steps S41 and S42.

In Step S41, the measuring equipment 400 measures the physical quantity G relating to the field-effect transistor TN while varying the value of the correction factor β at the second temperature T2 and the specific voltage value X of the reference voltage Vgs0.

In Step S42, the computer 300 defines, as the specific factor value W of correction factor β, the value of the correction factor β when of a plurality of physical quantities G measured while varying the value of the correction factor β in Step S41, the physical quantity G substantially matching the target physical quantity Gd is measured. The first embodiment therefore makes it possible to uniquely and quickly identify the specific factor value W that is the value of the correction factor β corresponding to the target physical quantity Gd.

Modification Example

First to fourth modification examples according to the first embodiment of the present invention will be described with reference to FIGS. 24A to 24D. In FIGS. 24A to 24D, a control voltage generator 10 and a temperature detector 13 are omitted for the sake of simplification of the drawings. In the following first to fourth modification examples, components different from the resistance device 100 according to the first embodiment in FIG. 1 will be mainly described.

Figure 24A:
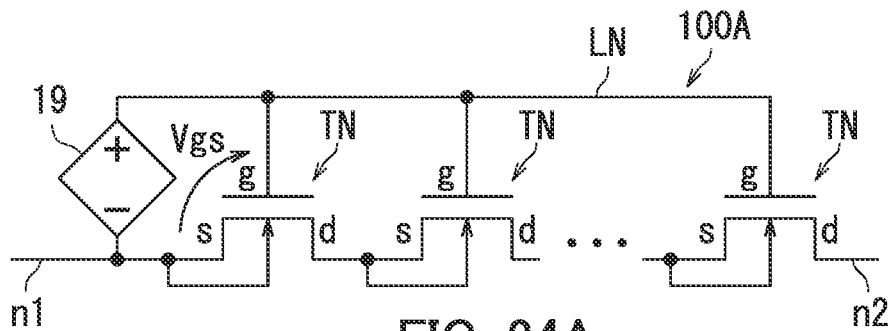
FIGS. 24A to 24D illustrate respective resistance devices of first to fourth modification examples according to the first embodiment.

FIG. 24A is a diagram illustrating a resistance device 100A of the first modification example according to the first embodiment. As illustrated in FIG. 24A, the resistance device 100A includes a voltage-controlled voltage source 19 and a plurality of transistors TN. The plurality of transistors TN are connected in series between a node n1 and a node n2. The voltage-controlled voltage source 19 is connected between a line LN to which respective gate terminals of the plurality of transistors TN are connected and the node n1. The voltage-controlled voltage source 19 therefore applies a control voltage Vgs between respective gate terminals of the plurality of transistors TN and a single source terminal connected to the node n1.

Further, respective back-gate terminals of the plurality of transistors TN are connected to their respective source terminals. Therefore, the source-drain voltage Vds of each transistor TN is lower than that in the case where the back-gate terminals are not connected to any source terminals. As a result, the linearity of the characteristics of each transistor TN is improved. In addition, the influence of the substrate bias effect can be suppressed.

Figure 24B:
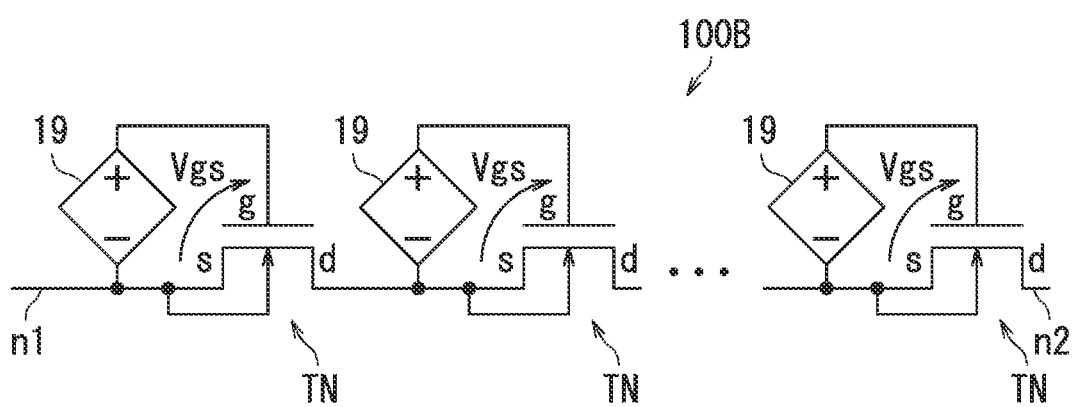

FIG. 24B is a diagram illustrating a resistance device 100B of the second modification example according to the first embodiment. As illustrated in FIG. 24B, the resistance device 100B includes a plurality of voltage-controlled voltage sources 19 and a plurality of transistors TN. The plurality of transistors TN are connected in series between a node n1 and a node n2. Respective back-gate terminals of the plurality of transistors TN are connected to their respective source terminals. Therefore, like the first modification example, the linearity of the characteristics of each transistor TN is improved, and the influence of the substrate bias effect can be suppressed.

The plurality of voltage-controlled voltage sources 19 are placed corresponding to the plurality of transistors TN. Each voltage-controlled voltage source 19 is connected between the gate and source terminals of a corresponding transistor TN. Each voltage-controlled voltage source 19 therefore applies a control voltage Vgs between the gate and source of the corresponding transistor TN. As a result, in the plurality of transistors TN, the difference in voltage between the gate and source due to the potential at the node n2 on the drain side of the transistor TN can be suppressed.

Figure 24C:
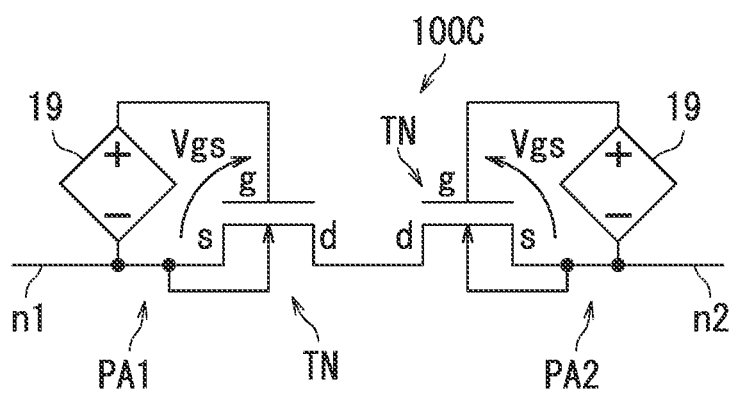

FIG. 24C is a diagram illustrating a resistance device 100C of the third modification example according to the first embodiment. As illustrated in FIG. 24C, the resistance device 100C includes two voltage-controlled voltage sources 19 and two transistors TN. The two transistors TN are connected in series between a node n1 and a node n2. In this case, the drain terminal of one transistor TN is connected to the drain terminal of the other transistor TN. Each of the voltage-controlled voltage sources 19 is placed between the gate and source terminals of a corresponding transistor TN. Further, respective back-gate terminals of the transistors TN are connected to their respective source terminals.

A pair PA1 of one voltage-controlled voltage source 19 and one transistor TN and a pair PA2 of the other voltage-controlled voltage source 19 and the other transistor TN are arranged symmetrically. As a result, the asymmetry with respect to the potential at the nodes n1 and n2 due to the connection destination of each back-gate terminal and/or the arrangement of the voltage-controlled voltage sources 19 can be suppressed.

Figure 24D:
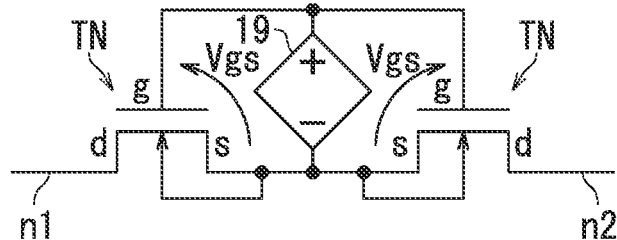

FIG. 24D is a diagram illustrating a resistance device 100D of the fourth modification example according to the first embodiment. As illustrated in FIG. 24D, the resistance device 100D includes one voltage-controlled voltage source 19 and two transistors TN. The two transistors TN are connected in series between a node n1 and a node n2. In this case, the source terminal of one transistor TN is connected to the source terminal of the other transistor TN. The voltage-controlled voltage source 19 is placed between the gate and source terminals of each transistor TN. The voltage-controlled voltage source 19 therefore applies a control voltage Vgs between the gate and source of each of the two transistors TN. Further, respective back-gate terminals of the transistors TN are connected to their respective source terminals.

One transistor TN and the other transistor TN are arranged symmetrically with respect to the voltage-controlled voltage source 19. As a result, the asymmetry with respect to the potential at the nodes n1 and n2 due to the connection destination of the back-gate terminals and/or the arrangement of the voltage-controlled voltage source 19 can be suppressed.

Note that although respective back-gate terminals of the transistors TN are connected to their respective source terminals in FIGS. 24A to 24D, each back-gate terminal may be connected to an earth or a ground (0 [V]). However, the linearity is inferior to the case where respective back-gate terminals of the transistors TN are connected to their respective source terminals.

Two or more of the first to fourth modification examples in FIGS. 24A to 24N may be combined. For example, the first and third modification examples may be combined to change each of the two transistors TN in FIG. 24C to a plurality of transistors TN in FIG. 24A. For example, the first and second modification examples may be combined to change each of the plurality of transistors TN in FIG. 24B to the plurality of transistors TN in FIG. 24A. For example, resistance devices in two or more modification examples of the first to fourth modification examples may be arranged in series or in parallel.

Second Embodiment

A resistance device 100Z according to a second embodiment of the present invention will be described with reference to FIGS. 25 to 32D. The resistance device 100Z according to the second embodiment uses a PMOS transistor as MOS resistance. In this respect, the second embodiment mainly differs from the first embodiment using an NMOS transistor as MOS resistance. Hereinafter, components of the second embodiment differing from those of the first embodiment will be mainly described.

Figure 25:
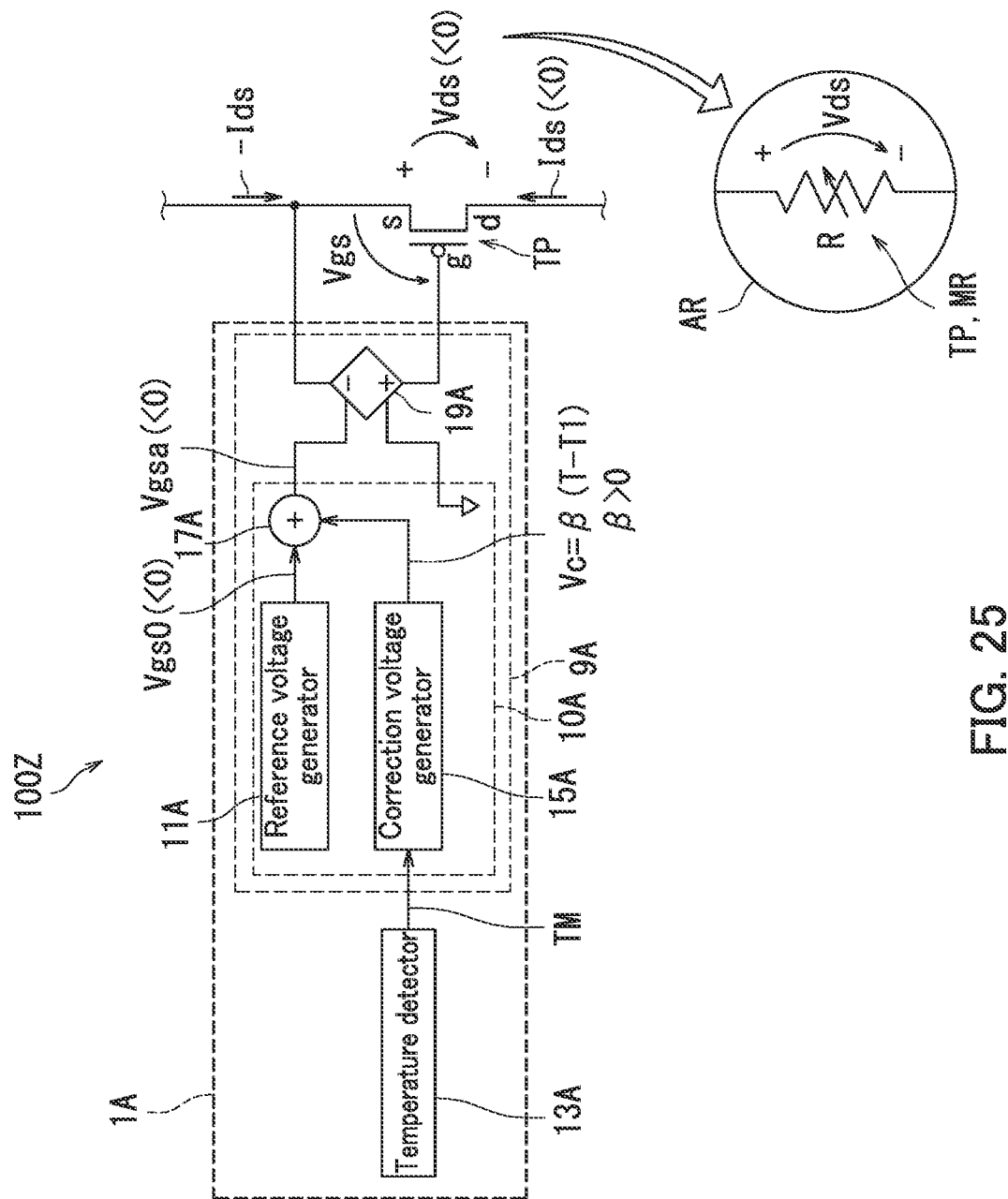
FIG. 25 is a diagram illustrating a resistance device according to a second embodiment of the present invention.

FIG. 25 is a diagram illustrating the resistance device 100Z according to the second embodiment. As illustrated in FIG. 25, the resistance device 100Z includes a field-effect transistor TP and a voltage applying circuit 1A. As illustrated in FIG. 25, the field-effect transistor TP in the second embodiment is a P-type field-effect transistor. Specifically, the field-effect transistor TP is a p-type metal-oxide-semiconductor field-effect transistor (p-type MOSFET), that is, a PMOS transistor.

Hereinafter, the field-effect transistor TP may be referred to as a "transistor TP".

Note that the back-gate terminal of the field-effect transistor TP may be connected to the source terminal of the field-effect transistor TN, or may be connected to a power source.

The field-effect transistor TP functions as a resistance element. Specifically, the field-effect transistor TP functions as a resistance element by utilizing the resistance between the drain and source of the field-effect transistor TP. That is, the field-effect transistor TP functions as MOS resistance. More specifically, the field-effect transistor TP functions as a resistance element by utilizing the resistance between the drain and source of the field-effect transistor TP in a region (linear region and saturation region) where the gate-source voltage is larger than the threshold voltage. The field-effect transistor TP also functions as a resistance element by utilizing the resistance between the drain and source of the field-effect transistor TP in a region (subthreshold region) where the gate source voltage is lower than the threshold voltage.

An equivalent circuit where the field-effect transistor TP functions as MOS resistance MR is illustrated in a region AR in FIG. 25.

Hereinafter, a resistance value R between the drain and source of the field-effect transistor TP may be described as a "resistance value R of the field-effect transistor TN".

The voltage applying circuit 1A applies a control voltage Vgs according to a temperature T between the gate and source of the field-effect transistor TP to control the resistance value R between the drain and source of the field-effect transistor TN. The "between the gate and source of the field-effect transistor TP" means "between the gate and source terminals of the field-effect transistor TP". The temperature T corresponds to the ambient temperature of the resistance device 100. The control voltage Vgs has a negative value. The control voltage Vgs represents a voltage between the gate and source of the field-effect transistor TP.

The control voltage Vgs corresponds to a voltage obtained by adding a correction voltage Vc to a reference voltage Vgs0. Specifically, the control voltage Vgs is expressed as Equation (28).

$$Vgs = Vgs0 + Vc \qquad \text{Equation (28):}$$

The correction voltage Vc is a voltage to be added to the reference voltage Vgs0 in order to reduce temperature dependence of a desired physical quantity relating to the field-effect transistor TP.

The physical quantity relating to the field-effect transistor TP is a physical quantity containing the resistance value R of the field-effect transistor TP that is measurable from an electronic circuit including the field-effect transistor TP. The "physical quantity containing the resistance value R" is a physical quantity depending on the resistance value R. For example, the physical quantity relating to the field-effect transistor TP is the resistance value R between the drain and source of the field-effect transistor TP, or a cutoff frequency fc of a filter circuit including the field-effect transistor TP. Note that the physical quantity relating to the field-effect transistor TP is not limited to the resistance value R and the cutoff frequency fc, like the physical quantity relating to the field-effect transistor TN in the first embodiment. An example of the physical quantity relating to the field-effect transistor TN is applied as an example of the physical quantity relating to the field-effect transistor TP. Hereinafter, a desired physical quantity relating to the field-effect transistor TP may be described as a "target physical quantity". Therefore, the target physical quantity is a physical quantity containing the resistance value R of the field-effect transistor TP, which is measurable from an electronic circuit including the field-effect transistor TP. The target physical quantity is a physical quantity that is set as a target value.

Specifically, the correction voltage Vc is expressed as Equation (29), where R denotes a correction factor, T denotes a temperature, and T1 denotes a first temperature. The correction factor β is a factor for determining the correction voltage Vc. In the second embodiment, the correction factor β has a positive value. The correction voltage Vc therefore increases as the temperature T rises. Specifically, the correction factor β is a factor for correcting the control voltage Vgs to be applied between the gate and source of the field-effect transistor TP in order to reduce the temperature dependence of a desired physical quantity relating to the field-effect transistor TP.

$$Vc = \beta(T - T1) \qquad \text{Equation (29):}$$

As in Equation (29), the correction voltage Vc depends on the temperature T and is set to be zero at the first temperature T1. In other words, the first temperature T1 is a temperature at which the correction voltage Vc becomes zero. A correction effect is therefore lost at the first temperature T1 in the second embodiment. It is possible to efficiently determine a combination of the correction factor β for correcting the control voltage Vgs to be applied between the gate and source of the field-effect transistor TP and a desirable physical quantity relating to the field-effect transistor TP by utilizing the voltage application circuit 1A such that the correction effect is eliminated at the first temperature T1. This is similar to the first embodiment.

Note that even in the second embodiment, the control voltage Vgs can be corrected by the linear function of Equation (29) even in the subthreshold region and the saturation and linear regions of the "|Vgs|>|Vth|".

In the second embodiment, the field-effect transistor TP is a PMOS transistor. The "|Vgs|>|Vth|" region is therefore an operating region of the PMOS transistor when the magnitude of the gate-source voltage Vgs is larger than the magnitude of the threshold voltage Vth. The "|Vgs|>|Vth|" region corresponds to an example of a "first operating region of the field-effect transistor". Of the "|Vgs|>|Vth|" region, a region corresponding to "|Vds|>|Vgs−Vth|" is a saturation region of the PMOS transistor. Of the "|Vgs|>|Vth|" region, a region corresponding to "|Vds|<|Vgs− Vth|" is a linear region of the PMOS transistor. A subthreshold region is an operating region (|Vgs|<|Vth|) of the PMOS transistor when the magnitude of the gate-source voltage Vgs is smaller than the magnitude of the threshold voltage Vth. The subthreshold region corresponds to an example of a "second operating region of the field-effect transistor".

Also in the second embodiment, the correction factor 3 can be determined in any of the saturation region of the "|Vgs|>|Vth|" region, the linear region of the "|Vgs|>|Vth|" region, and the subthreshold region by procedures similar to the procedures described with reference to FIGS. 11A to 13C and FIGS. 17A to 17C in the first embodiment.

This is because the transistor TP that is a PMOS transistor is different only in polarity from the transistor TN that is an NMOS transistor. The difference in polarity between the transistor TP and the transistor TN means a difference in polarity between gate-source voltages Vgs, a difference in polarity between drain-source voltages Vds, and a difference in polarity between drain currents Ids, as illustrated in FIGS. 1 and 25.

That is, the drain current Ids of the transistor TP in the saturation region of the "|Vgs|>|Vth|" region is expressed as Equation (30). As is clear from the comparison between Equations (30) and (10), the transistor TP and the transistor TN differ only in polarity in the saturation region. The temperature coefficient uth has a positive value.

[Math. 14]

$$I_{ds} = -\frac{1}{2}\mu_{n\_} T_0 \cdot (T/T_0)^{\alpha_\mu} \cdot \qquad \text{Equation (30)}$$

$$C_{ox}\frac{W}{L}(V_{gs} - V_{th\_}T_0 - \alpha_{th}(T - T_0))^2$$

Further, the drain current Ids of the transistor TP in the linear region of the "|Vgs| >|Vth|" region is expressed as Equation (31). As is clear from the comparison between Equations (31) and (9), the transistor TP and the transistor TN differ only in polarity in the linear region. The temperature coefficient uth has a positive value.

[Math. 15]

$$I_{ds} = -\mu_{n\_} T_0 \cdot (T/T_0)^{\alpha_\mu} \cdot \qquad \text{Equation (31)}$$

$$C_{ox}\frac{W}{L}\left[(V_{gs}-V_{th\_}T_0-\alpha_{th}(T - T_0))V_{ds}-\frac{1}{2}V_{ds}^2\right]$$

Further, the drain current Ids of the transistor TP in the subthreshold region (|Vgs| <|Vth|) is expressed as Equation (32). As is clear from the comparison between Equations (32) and (22), the transistor TP and the transistor TN differ only in polarity in the subthreshold region.

[Math. 16]

$$I_{ds} = -\mu_{n\_} T_0 \cdot (T/T_0)^{\alpha_\mu} \cdot \qquad \text{Equation (32)}$$

$$C_{ox}\frac{W}{L}(\eta - 1)V_t^2 e^{-\frac{V_{gs}-V_{th}}{\eta V_t}}\left(1 - e^{+\frac{V_{ds}}{V_t}}\right)$$

Figure 26:
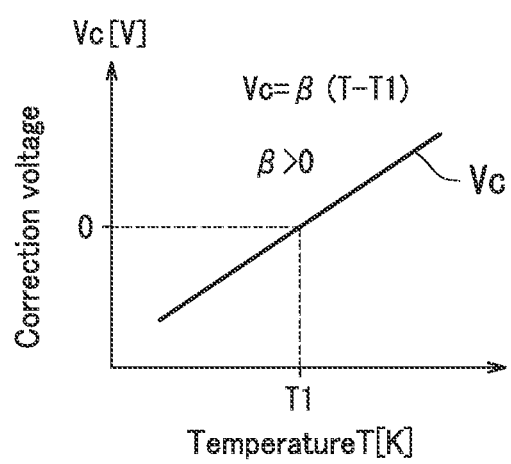
FIG. 26 is a graph illustrating temperature dependence of correction voltage in the second embodiment.

FIG. 26 is a graph illustrating the correction voltage Vc. Correction voltage Vc [V] is on the vertical axis, and temperature T [K] is on the horizontal axis. As illustrated in FIG. 26, the correction voltage Vc varies linearly with respect to the temperature T. The slope of the straight line of the correction voltage Vc corresponds to the correction factor β. However, since the transistor TP differs in polarity from the transistor TN, the slope of the straight line of the correction voltage Vc, that is, the correction factor β has a positive value unlike the graph illustrating the correction voltage Vc in FIG. 2 in the first embodiment.

Returning to FIG. 25, the details of the voltage applying circuit 1A will be described. The voltage applying circuit 1A is placed between the gate source terminals of the transistor TP. The potential (hereinafter, may be referred to as "source potential Vs") at the source terminal can take any value like the first embodiment.

The voltage applying circuit 1A includes a control voltage applying section 9A and a temperature detector 13A. The temperature detector 13A detects the temperature T and outputs a detection signal TM according to the temperature T to the control voltage applying section 9A. Other than that, the temperature detector 13A is the same as the temperature detector 13 in FIG. 1. For example, the temperature detector 13A may have the same configuration as the temperature detector 13 in FIG. 8.

The control voltage applying section 9A generates the control voltage Vgs containing the correction voltage Vc that varies linearly with respect to the temperature T according to the detection signal TM. The control voltage applying section 9A then applies the control voltage Vgs between the gate and source of the transistor TP. Other than that, the control voltage applying section 9A is the same as the control voltage applying section 9 in FIG. 1.

Specifically, the control voltage applying section 9A includes a control voltage generator 10A and a voltage-controlled voltage source 19A.

The control voltage generator 10A generates a control voltage Vgsa containing the correction voltage Vc that varies linearly with respect to the temperature T according to the detection signal TM. The control voltage Vgsa has a negative value. The control voltage Vgsa may be described as a "reference control voltage Vgsa". The control voltage Vgsa is expressed as Equation (33).

$$Vgsa=Vgs0+Vc \qquad \text{Equation (33):}$$

As is clear from Equations (28) and (33), the control voltage Vgsa and the control voltage Vgs have the same voltage component (reference voltage Vgs0 and correction voltage Vc) and the same voltage value. Also in Equation (33), the correction voltage Vc is expressed as Equation (29). Other than that, the control voltage generator 10A is the same as the control voltage generator 10 in FIG. 1.

The control voltage Vgsa is a voltage with a reference designated 0 [V] (that is, a potential difference with a reference designated 0 [V]) like the first embodiment. Therefore, the control voltage applying section 9A includes the voltage-controlled voltage source 19A for the same reason as in the first embodiment, The voltage-controlled voltage source 19A is connected between the gate and source terminals of the transistor TP. The voltage-controlled voltage source 19A is a voltage source in which the potential difference between two output terminals is determined according to the potential difference between two input terminals. The control voltage Vgsa with the reference designated 0 [V] and 0 [V] as the reference are input to the voltage-controlled voltage source 19A from the control voltage generator 10A, whereby the control voltage Vgsa is input as the potential difference. The two output terminals of the voltage-controlled voltage source 19A are connected to the gate and source terminals of the transistor TN, so that the control voltage Vgs having the same voltage value as the control voltage Vgsa is applied between the gate and source of the transistor TP. At this time, even if the source potential Vs fluctuates, the potential Vgs between the two output terminals of the voltage-controlled voltage source 19A does not fluctuate. Other than that, the voltage-controlled voltage source 19A is the same as the voltage-controlled voltage source 19 in FIG. 1. For example, the voltage-controlled voltage source 19A may have the same configuration as the voltage-controlled voltage source 19 in FIGS. 7A and 7B.

The control voltage Vgsa may be input to the voltage-controlled voltage source 19A as a potential difference, and therefore 0 [V] as the reference may be set to an arbitrary value like the first embodiment. In the case where Vref denotes the voltage as the reference, if the output voltage of the control voltage generator 10A is expressed as "Vgsa+Vref", the potential difference to be input to the voltage-controlled voltage source 19A becomes "Vgsa+Vref−Vref", namely Vgsa.

The control voltage generator 10A may be configured by an arbitrary control voltage generating circuit because the configuration of the control voltage generator 10A is not particularly limited as long as the control voltage Vgsa expressed as Equation (33) can be generated.

In the second embodiment, the control voltage generator 10A includes a reference voltage generator 11A, a correction voltage generator 15A, and an addition section 17A.

The reference voltage generator 11A generates the reference voltage Vgs0 to be output to the addition section 17A. The reference voltage Vgs0 has a negative value. On the other hand, the correction voltage generator 15A generates the correction voltage Vc based on the detection signal TM by the temperature detector 13A and outputs the correction voltage Vc to the addition section 17A. The addition section 17A adds the correction voltage Vc to the reference voltage Vgs0 to generate the control voltage Vgsa as the addition result. The addition section 17A then outputs the control voltage Vgsa to the voltage-controlled voltage source 19A.

Other than that, the reference voltage generator 11A, the correction voltage generator 15A, and the addition section 17A are the same as the reference voltage generator 11, the correction voltage generator 15, and the addition section 17 in FIG. 1, respectively. For example, the correction voltage generator 15A may have the same configuration as the correction voltage generator 15 in FIG. 8. Note that FIG. 25 illustrates the physical or logical configuration of the control voltage generator 10A like FIG. 1.

Next, the details of the temperature detector 13A and the correction voltage generator 15A will be described with reference to FIGS. 8 and 27A to 27C. The temperature detector 13A and the correction voltage generator 15A are the same as the temperature detector 13 and the correction voltage generator 15 in FIG. 8, respectively.

Figure 27A:
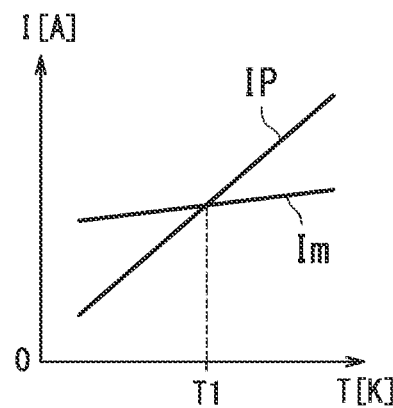
FIG. 27A is a graph illustrating temperature dependence of first current and temperature dependence of second current in the second embodiment.
Figure 27B:
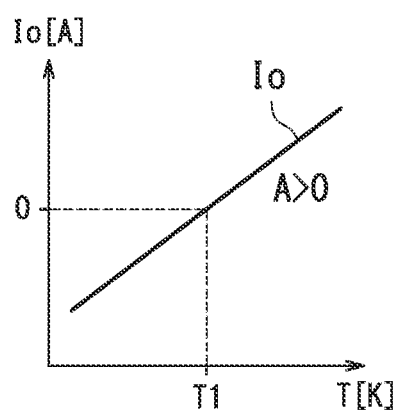
FIG. 27B is a graph illustrating temperature dependence of differential current in the second embodiment.
Figure 27C:
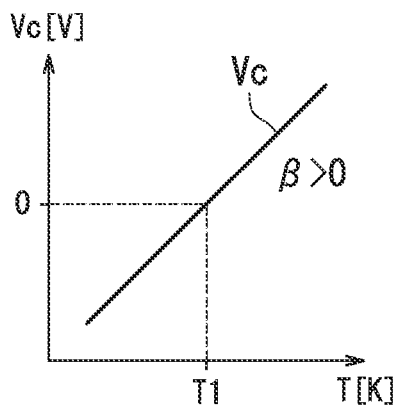
FIG. 27C is a graph illustrating temperature dependence of correction voltage in the second embodiment.

FIG. 27A is a graph illustrating the temperature dependence of a first current Ip and the temperature dependence of a second current Im. FIG. 27B is a graph illustrating the temperature dependence of a differential current Io. FIG. 27C is a graph illustrating the temperature dependence of the correction voltage Vc.

As illustrated in FIG. 27A, the temperature dependence of the first current Ip differs from the temperature dependence of the second current Im like the first embodiment. Each of the first and second currents Ip and Im varies linearly with respect to the temperature T.

In the example of FIG. 27A, the temperature dependence of the first current Ip is higher than the temperature dependence of the second current Im. That is, the temperature dependence of a first current source circuit 131 is higher than the temperature dependence of a second current source circuit 133.s A first temperature T1 is a temperature T when the first current Ip coincides with the second current Im. That is, the first temperature T1 is a temperature T when the differential current Jo becomes zero.

As illustrated in FIG. 27B, the differential current Jo (=Ip−Im) has a positive temperature characteristic. That is, the slope A of the straight line representing the difference current Jo has a positive value. The differential current Jo is therefore expressed as Equation (34). The differential current Jo is zero when the temperature T is the first temperature T1.

$$Io = A \times (T - T1) \qquad \text{Equation (34):}$$

Since the differential current Jo has a positive temperature characteristic, the correction voltage Vc also has a positive temperature characteristic as illustrated in FIG. 27C. The graph of FIG. 27C coincides with the graph of the temperature dependence of the correction voltage Vc in FIG. 26. The correction voltage Vc is expressed as Equation (35).

$$Vc = Ro \times Io = Ro \times A \times (T - T1) = \beta(T - T1) \qquad \text{Equation (35):}$$

As in Equation (35), "Ro×A" denotes the correction factor β. The correction factor β has a positive value. Further, the correction voltage Vc is zero when the temperature T is the first temperature T1.

Note that although the slopes of the straight lines representing the first and second currents Ip and Im have positive values in the example of FIG. 27A, they do not necessarily have positive values. In the second embodiment, the slope of the first current Ip should be larger than the slope of the second current Im in order that the correction factor β of the correction voltage Vc becomes positive for the correction to the temperature dependence of the transistor TP. The sign (positive/negative) of the slope is therefore irrelevant.

Note that even in the second embodiment, the first temperature T1 can be varied by varying the current value of the first current Ip and/or the current value of the second current Im, like the first embodiment.

Here, the correction factor β for correcting the temperature dependence of the transistor TP is reflected in Equation (30), and then the drain current Ids of the transistor TP is expressed as Equation (36) in the saturation region (|Vds|>|Vgs− Vth|) of the "|Vgs|>|Vth" region.

[Math. 17]

$$I_{ds} = -\frac{1}{2}\mu_{n\_} T_0 \cdot (T/T_0)^{\alpha_\mu} \cdot C_{ox}\frac{W}{L}(V_{gs0} + \beta(T-T_1) - V_{th\_}T_0 - \alpha_{th}(T-T_0))^2 \quad \text{Equation (36)}$$

Further, the correction factor β is reflected in Equation (31), and then the drain current Ids of the transistor TP is expressed as Equation (37) in the linear region (|Vds|<|Vgs− Vth|) of the "|Vgs|>|Vth|" region. The temperature coefficient uth has a positive value.

[Math. 18]

$$I_{ds} = -\mu_{n\_} T_0 \cdot (T/T_0)^{\alpha_\mu} \cdot C_{ox}\frac{W}{L}\left[(V_{gs0}+\beta(T-T_1)-V_{th\_}T_0-\alpha_{th}(T-T_0))V_{ds}-\frac{1}{2}V_{ds}^2\right] \quad \text{Equation (37)}$$

The correction factor β is also reflected in Equation (32), and then the drain current Ids of the transistor TP is expressed as Equation (38) in the subthreshold region. The temperature coefficient uth has a positive value.

[Math. 19]

$$I_{ds} = -\mu_{n\_} T_0 \cdot (T/T_0)^{\alpha_\mu} \cdot C_{ox}\frac{W}{L}(\eta-1)V_t^2 e^{-\frac{V_{gs0}+\beta(T-T_1)-V_{th}}{\eta V_t}}\left(1-e^{+\frac{V_{ds}}{V_t}}\right) \quad \text{Equation (38)}$$

The resistance value R of the transistor TP is expressed as Equation (39) in any of the saturation region, the linear region, and the subthreshold region.

$$R=V_{ds}/I_{ds} \quad \text{Equation (39):}$$

Figure 28A:
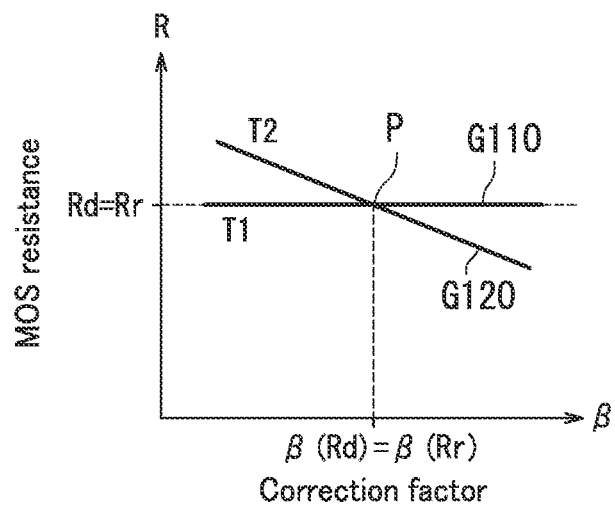
FIG. 28A is a graph illustrating R-β curves of resistance value of the transistor against correction factor at first temperature and second temperature in the second embodiment.

Next, an example of the correction factor (β) determining method will be described with reference to FIG. 28A. FIG. 28A is a graph illustrating the relationship between the correction factor β and the resistance value R of the transistor TP at the first temperature T1, and the relationship between the correction factor β and the resistance value R of the transistor TP at the second temperature T2. The first and second temperatures T1 and T2 are the same as the first and second temperatures T1 and T2 in the first embodiment, respectively.

As illustrated in FIG. 28A, an R-β curve G110 represents the resistance value R at the first temperature T1. An R-β curve G120 represents the resistance value R at the second temperature T2. A correction factor β (Rr) at an intersection P of the R-β curve G110 and the R-β curve G120 is acquired by the same procedures as those of the first embodiment described with reference to FIG. 12B. In the second embodiment, a resistance value Rr without temperature dependence corresponding to the correction factor β (Rr) always coincides with a target resistance value Rd like the first embodiment. At this time, the correction factor β (Rr) at the intersection P also coincides with a correction factor β (Rd) for the target resistance value Rd. Therefore, in the second embodiment, when the correction factor β (Rd) is set to the correction factor β of the correction voltage generator 15A in the resistance device 100A, the correction voltage Vc effectively reduces the temperature dependence of the resistance value R of the transistor TP. As a result, the resistance value R can be maintained at the target resistance value Rd.

Figure 28B:
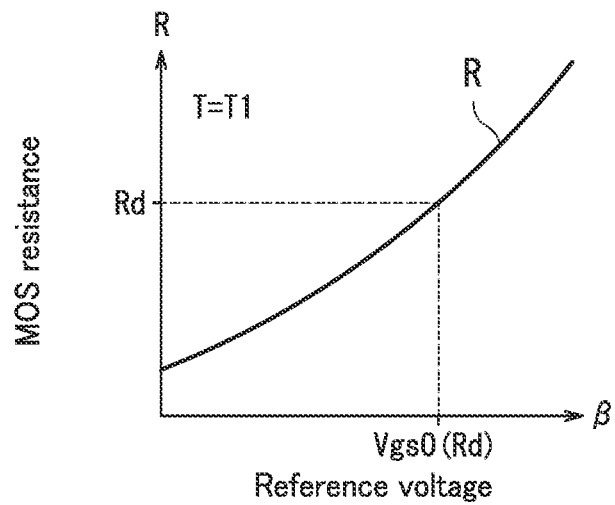
FIG. 28B is a graph illustrating the relationship between reference voltage and resistance value of the transistor at first temperature in the second embodiment.
Figure 28C:
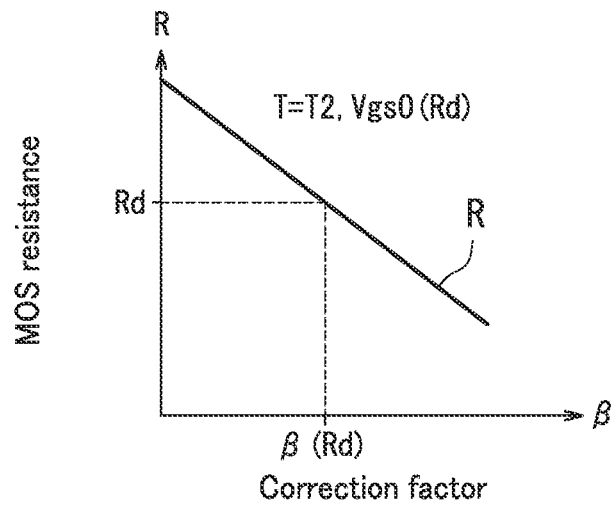
FIG. 28C is a graph illustrating the relationship between correction factor and resistance value of the transistor at second temperature in the second embodiment.

Next, a more preferable example of the correction factor (β) determining method will be described with reference to FIGS. 28B and 28C. FIG. 28B is a graph illustrating the relationship between the resistance value R of the transistor TP and the reference voltage Vgs0 at the first temperature T1. FIG. 28C is a graph illustrating the relationship between the resistance value R of the transistor TP and the correction factor β at the second temperature T2. The correction factor β is determined by (Procedure 1) and (Procedure 2) described below.

(Procedure 1)

As illustrated in FIG. 28B, a reference voltage Vgs0 (Rd) when the resistance value R corresponds to the target resistance value Rd is determined by measuring the resistance value R of the transistor TP in the resistance device 100A while varying the voltage value of the reference voltage Vgs0 at the first temperature T1 where the correction voltage Vc becomes zero. Note that since the correction voltage Vc is zero at the first temperature T1, the correction factor β may be any value, and the reference voltage Vgs0 (Rd) coincides with the control voltage Vgsa in FIG. 25 and Equation (33).

(Procedure 2)

As illustrated in FIG. 28C, in the resistance device 100A, the reference voltage Vgs0 is set to the reference voltage Vgs0 (Rd) determined by (Procedure 1). A correction factor β (Rd) when the resistance value R corresponds to the target resistance value Rd is then determined by measuring the resistance value R of the transistor TP while varying the value of the correction factor β at the second temperature T2 different from the first temperature T1. The target resistance value Rd coincides with the resistance value Rr without temperature dependence.

As described above with reference to FIGS. 28A and 28B, the correction factor β (Rd), at which the target resistance value Rd matching the resistance value Rr without temperature dependence is obtained, is determined by (procedure 1) and (procedure 2) in the second embodiment. The second embodiment therefore make it possible to uniquely and quickly identify the combination of the correction factor β (Rd) and the target resistance value Rd without temperature dependence like the first embodiment, The voltage applying circuit 1 that generates the correction voltage Vc such that the correction effect disappears at the first temperature T1 is suitable for realization of (procedure 1) and (procedure 2) in particular.

Note that the method for measuring the resistance value R of the transistor TP when determining the correction factor β is the same as that of the first embodiment described with reference to FIGS. 18A and 18B.

It can be understood from the above that even in the second embodiment in which the transistor TP, which is a PMOS transistor, is used as the MOS resistance, the temperature correction becomes possible in the same way as the first embodiment.

So far, in order to correct the temperature of the resistance value R of the transistor TP in the resistance device 100Z, the method of measuring the resistance value R of the target transistor TP has been described as an example. However, the temperature of the resistance value R of the transistor TN can be corrected by a physical quantity other than the resistance value R like the first embodiment. In other words, using a physical quantity (hereinafter referred to as a "physical quantity G") that is measurable from an electronic circuit including the resistance device 100Z that performs the temperature correction enables the determination of the reference voltage Vgs0 and the correction factor β for the temperature correction. Hereinafter, the physical quantity G measurable from the electronic circuit may be described as a "physical quantity G of the electronic circuit".

Also in the second embodiment, when the transistor TP (MOS resistance MR) of the resistance device 100Z is built in as a circuit element of the electronic circuit 3B in FIG. 19A, the physical quantity G measurable from the electronic circuit 3B can be generalized and expressed as a function of the resistance value R of the transistor TP, and further generalized as a function of the temperature T, the reference voltage Vgs0, and the correction factor β like Equation (24) in the first embodiment.

That is, as described in the first Embodiment with reference to FIGS. 19A, 19B, and Equation (24), in the second embodiment, the correction factor β (Gd) and the reference voltage Vgs0 (Gd) with respect to the target physical quantity Gd can be determined, and the temperature correction can be performed by measuring the physical quantity G containing the resistance value R of the transistor TP in the resistance device 100Z from the electronic circuit 3B including the transistor TP in the resistance device 100Z.

The first embodiment has been described with reference to FIGS. 19A, 20, and 21. Like the first embodiment, in the second embodiment as an example of FIG. 19A, the electronic circuit 3B is configured by the RC filter circuit 110X in FIG. 20A or 20B or by the active filter circuit 110C in FIG. 21, and the cutoff frequency fc is used as the physical quantity G to be measured. Even in this case, the temperature correction to the transistor TP in the resistance device 100Z, included in the RC filter circuit 110X or the active filter circuit 110C is possible.

Here, also in the second embodiment, the correction factor β for the transistor TP of the resistance device 100Z can be determined by the correction factor determining method according to the first embodiment described with reference to FIGS. 22 to 23B. Note that the method for determining the reference voltage Vgs0 and the correction factor R described with reference to FIGS. 11A and 12A can also be applied to the second embodiment.

Also in the second embodiment, the transistor TP and the voltage-controlled voltage source 19A can be arranged like the transistor TN and the voltage-controlled voltage source 19 in the first embodiment described with reference to FIGS. 24A to 24D.

Figure 29A:
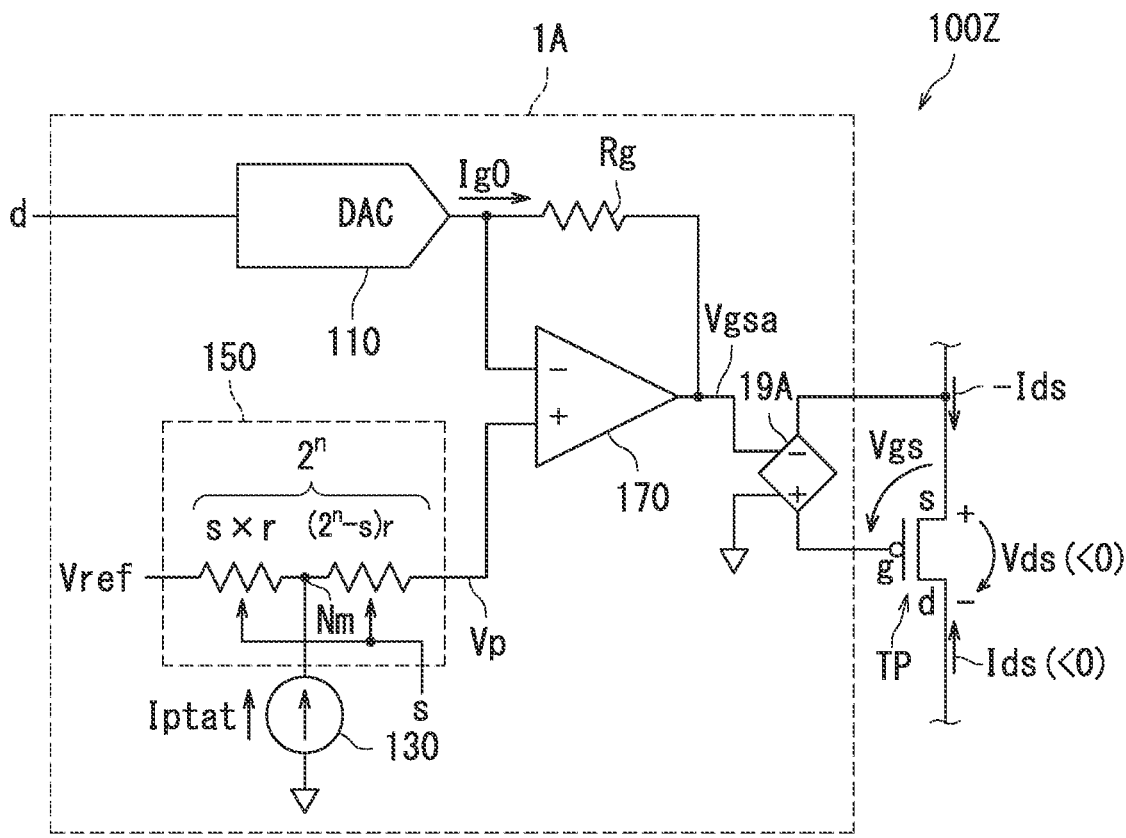
FIG. 29A is a circuit diagram illustrating an example of a voltage applying circuit in the second embodiment.

Next, an example of a voltage applying circuit 1A will be described as a specific circuit example in the second embodiment with reference to FIGS. 29A and 29B. FIG. 29A is a circuit diagram illustrating an example of the voltage applying circuit 1A. As illustrated in FIG. 29A, the voltage applying circuit 1A includes a digital to analog converter (DAC) 110, a resistance element Rg, a PTAT circuit 130, a variable resistor 150, a differential amplifier 170, and a voltage-controlled voltage source 19.

An output terminal of the DAC 110 is connected to a first terminal of the resistance element Rg and an inverting input terminal of the differential amplifier 170. A second terminal of the resistance element Rg is connected to an output terminal of the differential amplifier 170. A first terminal of the variable resistor 150 is connected to a non-inverting input terminal of the differential amplifier 170. A reference voltage Vref from a reference voltage generating circuit is input to a second terminal of the variable resistor 150

The DAC 110 in the second embodiment is, for example an R2-R ladder type m-bit DAC. An input code d is input to the DAC 110. The input code d is a digital code and is set in the range of "0<d≤2$^m$". The DAC 110 outputs a current Ig0 from the output terminal according to the input code d. The current Ig0 is expressed as Equation (40). In Equation (40), Ilsb denotes the minimum value of the current that the DAC 110 can output.

$$Ig0 = d \times Ilsb \qquad \text{Equation (40):}$$

The variable resistor 150 is, for example an n-bit resistance voltage divider (n-bit digital potentiometer). In FIG. 29, both ends of the variable resistor 150 are individually connected to the reference voltage Vref and the non-inverting input terminal of the differential amplifier 170. An intermediate node Nm located in the middle of both the ends of the variable resistor 150 is connected to the PTAT circuit 130. The variable resistor 150 has a structure in which $2^n$ resistors having the same resistance value are arranged in series, and the resistance value of one resistor is r. An input code s is input to the variable resistor 150. The input code s is a digital code and is set in the range of "0<s≤2$^n$". In FIG. 29, a node between the s-th resistor and the (s+1)-th resistor from the input side of the reference voltage Vref is connected to the intermediate node Nm of the variable resistor. Therefore, the resistance value from the input side of the reference voltage Vref to the intermediate node Nm is set to "s×r" according to the input code s.

The PTAT circuit 130 outputs a PTAT current Iptat according to the temperature T, and inputs the PTAT current Iptat to the intermediate node Nm of the variable resistor 150. Here, if no current flows through the non-inverting input terminal of the differential amplifier 170, the PTAT current Iptat all flows to the reference voltage Vref side because no current flows from the PTAT circuit 130 to the differential amplifier 170. At this time, no voltage drop occurs in a resistor between the intermediate node Nm of the variable resistor 150 and the non-inverting input terminal of the differential amplifier 170. As a result, the potential at the intermediate node Nm becomes equal to the potential Vp at the non-inverting input terminal of the differential amplifier 170. The potential at the intermediate node Nm becomes potential obtained by adding the reference voltage Vref to a voltage corresponding to the resistance value "s×r" from the intermediate node Nm to the input side of the reference voltage Vref and the PTAT current Iptat. From the above, the voltage Vp at the non-inverting input terminal of the differential amplifier 170 is expressed as Equation (41). The PTAT current Iptat corresponds to a detection signal TM. The PTAT circuit 130 therefore corresponds to a temperature detector 13.

$$Vp = s \times r \times Iptat + Vref \qquad \text{Equation (41):}$$

Figure 29B:
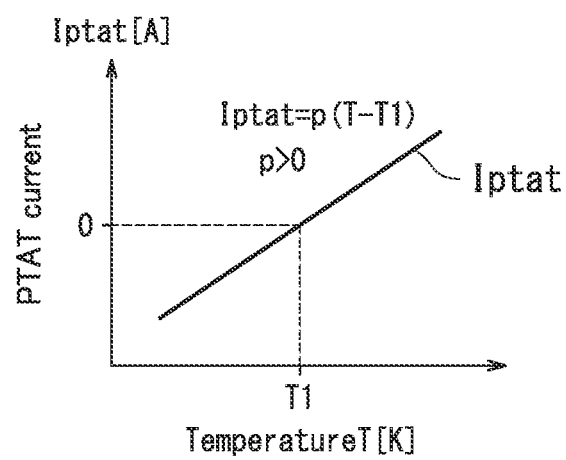
FIG. 29B is a diagram illustrating temperature dependence of PTAT current in the second embodiment.

FIG. 29B is a diagram illustrating the temperature dependence of the PTAT current Iptat. Temperature [K] is on the horizontal axis, and current values [A] is on the vertical axis. As illustrated in FIG. 29B, the PTAT current Iptat is proportional to the temperature T. The PTAT current Iptat is expressed as Equation (42), where p denotes a proportionality constant, and T1 denotes a first temperature. The p has a positive value. The PTAT circuit 130 is configured to include the first temperature T1 at which the current value of the PTAT current Iptat becomes zero.

$$Iptat = p(T - T1) \qquad \text{Equation (42):}$$

Returning to FIG. 29A, the differential amplifier 170 inputs a voltage determined by the resistance value Rg of the resistance element Rg and the current Ig0, and the voltage Vp, and outputs a control voltage Vgsa. The control voltage Vgsa is expressed as Equation (43), where Vgs0 {d} is expressed as Equation (44), and R {s} is expressed as Equation (45). Vgs0{d} corresponds to a reference voltage Vgs0, and β{s} corresponds to a correction factor β.

$$Vgsa = -Rg \times Ig0 + Vp \qquad \text{Equation (43)}$$
$$= -d \times Rg \times Ilsb + Vref + s \times r \times p(T - T1)$$
$$= Vgs0\{d\} + \beta\{s\} \times (T - T1)$$
$$Vgs\{d\} = -d \times Rg \times Ilsb + Vref \qquad \text{Equation (44)}$$
$$\beta\{s\} = s \times r \times p \qquad \text{Equation (45)}$$

As is clear from Equation (44), the value of the reference voltage Vgs0{d} is variable by the input code d. Further, as is clear from Equation (45), the value of the correction factor β{s} is variable by the input code s.

Figure 30:
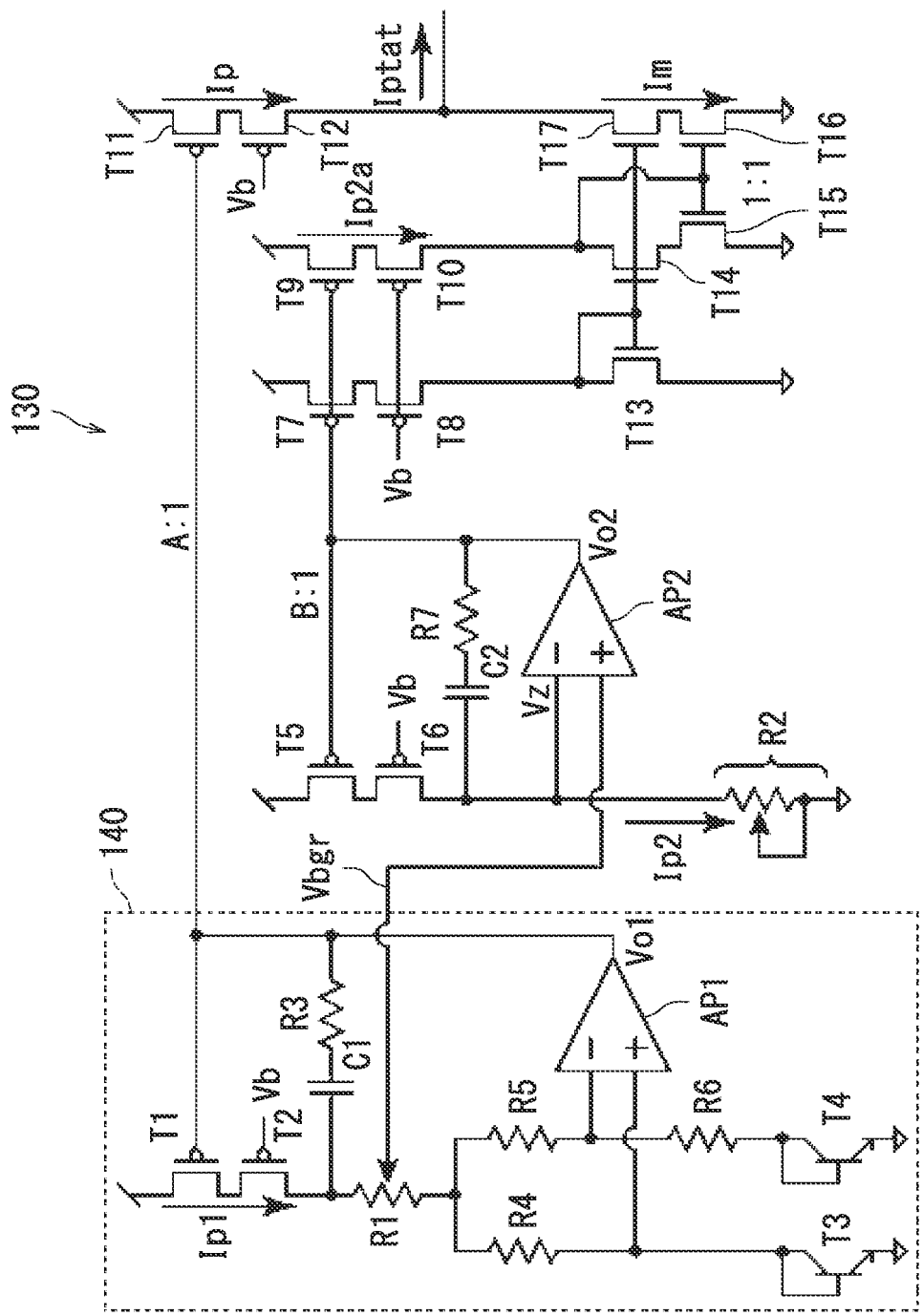
FIG. 30 is a circuit diagram illustrating an example of a PTAT circuit in the second embodiment.
Figure 31:
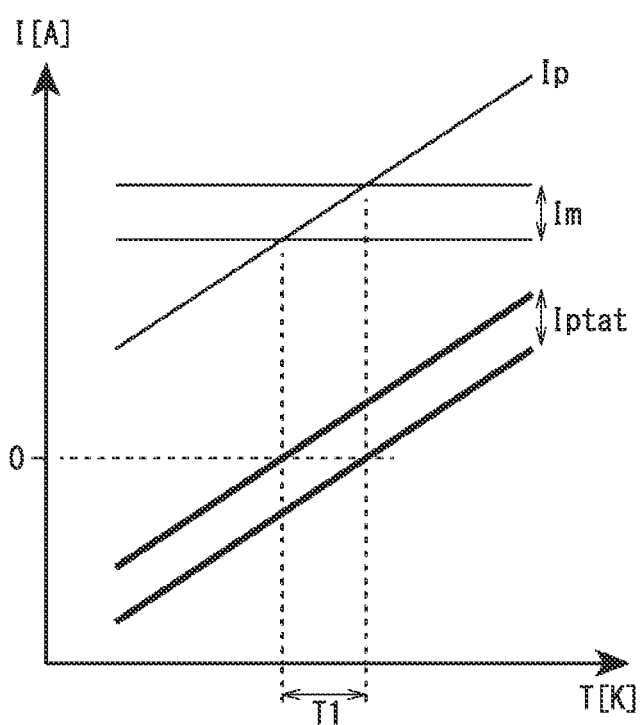
FIG. 31 is a graph illustrating a variable first temperature at which PTAT current becomes zero in the second embodiment.

An example of the PTAT circuit 130 in FIG. 29 will be described with reference to FIGS. 30 and 31. FIG. 30 is a circuit diagram illustrating an example of the PTAT circuit 130. FIG. 31 is a graph illustrating a PTAT current Iptat. Temperature [K] is on the horizontal axis, and current values [A] is on the vertical axis.

As illustrated in FIG. 30, the PTAT circuit 130 includes a band gap reference (BGR) circuit 140, PMOS transistors T5 to T12, NMOS transistors T14 to T17, a variable resistor R2, a resistance element R7, a capacitor C2, and an operational amplifier AP2. The BGR circuit 140 includes PMOS transistors T1 and T2, bipolar transistors T3 and T4, a variable resistor R1, resistance elements R3 to R6, a capacitor C1, and an operational amplifier AP1.

The PTAT circuit 130 outputs the PTAT current Iptat proportional to the temperature T.

Specifically, a current Ip1 flowing through the BGR circuit 140 has a positive linear temperature characteristic. A first current Ip flowing through the PMOS transistor T11 can be expressed as Ip=Ip1/A by a current mirror circuit. That is, A: 1=Ip1:Ip. Therefore, as illustrated in FIG. 31, the first current Ip has a positive temperature characteristic proportional to the current Ip1.

The BGR circuit 140 outputs a voltage Vbgr having a low temperature dependence. The voltage Vbgr having a low temperature dependence is input to a non-inverting input terminal of the operational amplifier AP2. In this case, due to the effect of the virtual short circuit of the operational amplifier AP2, a voltage Vz (≈Vbgr) having a low temperature dependence is obtained at an inverting input terminal of the operational amplifier AP2. When the voltage Vz is applied across the variable resistor R2, a current Ip2 (=R2× Vz) having a low temperature dependence flows through the variable resistor R2.

A second current Im flowing through the NMOS transistor T17 can be expressed as Im=Ip2a=Ip2/B by a current mirror circuit. That is, B: 1=Ip2:Ip2a. Therefore, as illustrated in FIG. 31, the second current Im is proportional to the low temperature-dependent current Ip2, and therefore has a low temperature dependence. A current value of the second current Im is variable by adjusting a resistance value of the variable resistor R2.

The PTAT circuit 130 outputs a difference current between the first current Ip and the second current Im as the PTAT current Iptat (=Ip–Im) to the variable resistor 150 in FIG. 29A. In this case, as illustrated in FIG. 31, the PTAT current Iptat becomes zero [A] at the first temperature T1 where the first current Ip coincides with the second current Im.

As illustrated in FIG. 31, the first temperature T1 at which the PTAT current Iptat becomes zero [A] can be adjusted by adjusting the resistance value of the variable resistor R2 to vary a current value of the second current Im, Note that a voltage Vb for operating the PTAT circuit 130 is input to respective gate terminals of the transistors T2, T6, T8, T10, and T12.

Modification Example

First to fourth modification examples according to the second embodiment of the present invention will be described with reference to FIGS. 32A to 32D. In FIGS. 32A to 32D, their respective control voltage generators 10A and temperature detectors 13A are omitted for the sake of simplification of the drawings. The following will describe respective components of the first to fourth modification examples different from those of the resistance device 100Z according to the second embodiment illustrated in FIG. 25.

Figure 32A:
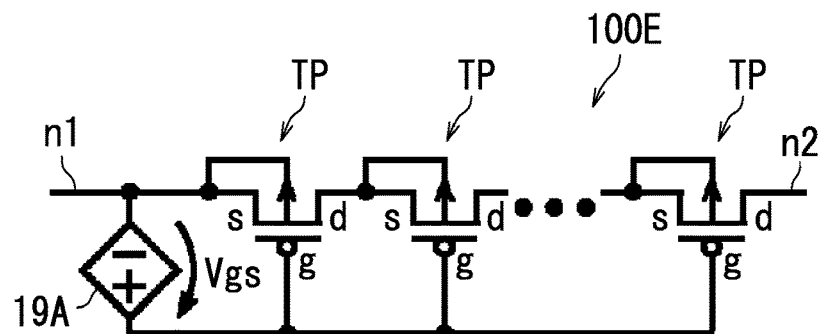
FIGS. 32A to 32D illustrate respective resistance devices of first to fourth modification examples according to the second embodiment.

FIG. 32A is a diagram illustrating a resistance device 100E of the first modification example according to the second embodiment. As illustrated in FIG. 32A, the resistance device 100E includes a voltage-controlled voltage source 19A and a plurality of transistors TP. The plurality of transistors TP are connected in series between a node n1 and a node n2. The voltage-controlled voltage source 19A is connected between a line LN to which respective gate terminals of the plurality of transistors TP are connected and the node n1. The voltage-controlled voltage source 19A therefore applies a control voltage Vgs between respective gate terminals of the plurality of transistors TP and a single source terminal connected to the node n1.

Further, respective back-gate terminals of the plurality of transistors TP are connected to their respective source terminals. Therefore, for the same reason as in the case of the resistance device 100A in FIG. 24A, the linearity of the characteristics of each transistor TP can be improved and the influence of the substrate bias effect can be suppressed.

Figure 32B:
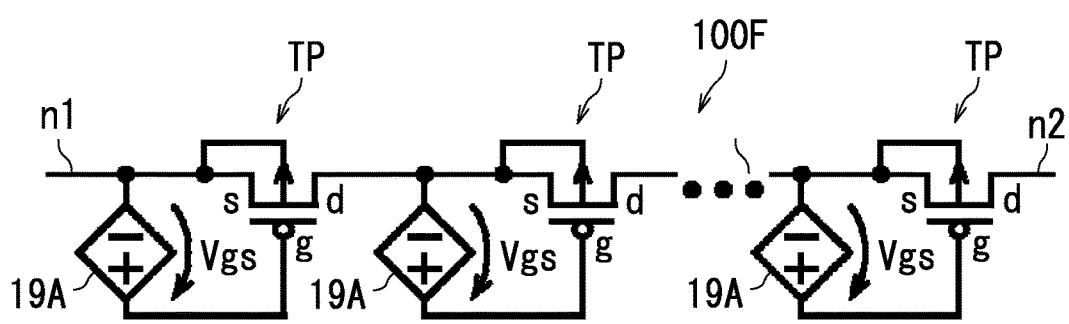

FIG. 32B is a diagram illustrating a resistor device 100F of a second modification example according to the second embodiment. As illustrated in FIG. 32B, the resistance device 100F includes a plurality of voltage-controlled voltage sources 19A and a plurality of transistors TP. The plurality of transistors TP are connected in series between a node n1 and a node n2. Respective back-gate terminals of the plurality of transistors TP are connected to their respective source terminals. Therefore, like the first modification, the linearity of the characteristics of each transistor TP is improved, and the influence of the substrate bias effect can be suppressed.

The plurality of voltage-controlled voltage sources 19A are individually connected to the plurality of transistors TP. That is, each voltage-controlled voltage source 19A is connected between the gate and source terminals of a corresponding transistor TP. Each voltage-controlled voltage source 19A therefore applies a control voltage Vgs between the gate and source of the corresponding transistor TP. It is consequently possible to suppress the difference in respective gate-source voltages of the plurality of transistors TP due to the potential at the node n2 on each drain side of the transistors TP.

Figure 32C:
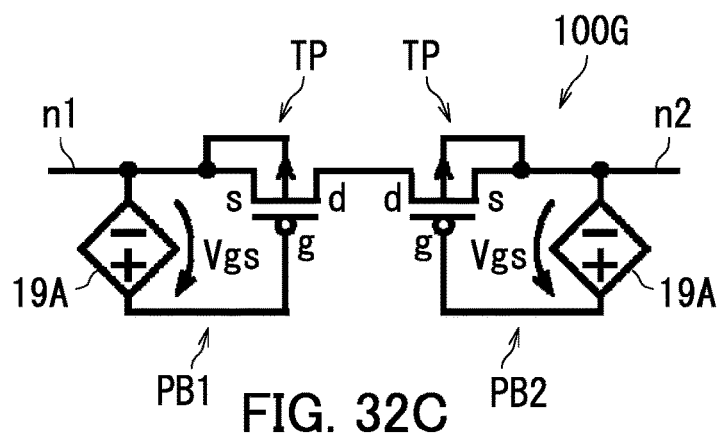

FIG. 32C is a diagram illustrating a resistance device 100G of a third modification example according to the second embodiment. As illustrated in FIG. 32C, the resistance device 100G includes two voltage-controlled voltage sources 19A and two transistors TP. The two transistors TP are connected in series between a node n1 and a node n2. In this case, a drain terminal of a first transistor TP is connected to a drain terminal of a second transistor TP. Each voltage-controlled voltage source 19A is placed between the gate and source terminals of a corresponding transistor TP. Respective back-gate terminals of the transistors TP are connected to their respective source terminals.

A pair PB1 of one voltage-controlled voltage source 19A and one transistor TP and a pair PB2 of the other voltage-controlled voltage source 19A and the other transistor TP are arranged symmetrically. As a result, the asymmetry with respect to the potential at the nodes n1 and n2 due to the connection destination of each back-gate terminal and/or the arrangement of the voltage-controlled voltage sources 19 can be suppressed.

Figure 32D:
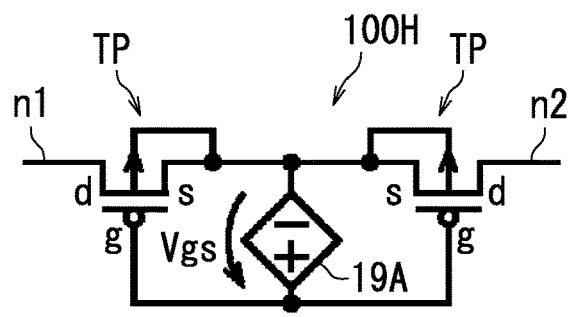

FIG. 32D is a diagram illustrating a resistance device 100H of the fourth modification example according to the second embodiment. As illustrated in FIG. 32D, the resistance device 100H includes one voltage-controlled voltage source 19A and two transistors TP. The two transistors TP are connected in series between a node n1 and a node n2. In this case, a source terminal of a first transistor TP is connected to a source terminal of a second transistor TP. The voltage-controlled voltage source 19A is placed between the gate and source terminals of each transistor TP. The voltage-controlled voltage source 19A therefore applies a control voltage Vgs between the gate and source of each of the two transistors TP. Further, respective back-gate terminals of the transistors TP are connected to their respective source terminals.

The one transistor TP and the other transistor TP are symmetrically arranged with respect to the voltage-controlled voltage source 19A. It is consequently possible to suppress the asymmetry with respect to the potential at the nodes n1 and n2 due to the connection destination of each back-gate terminal and/or the arrangement of the voltage-controlled voltage source 19A.

Note that although respective back-gate terminals of the plurality of transistors TP are connected to their respective source terminals in FIGS. 32A to 32D, they may be connected to a power supply voltage. The linearity is however inferior to the case where respective back-gate terminals of the plurality of transistors TP are connected to their respective source terminals.

Further, two or more of the first to fourth modification examples in FIGS. 32A to 32D may be combined. For example, with the first and third modification examples combined, each of the two transistors TP in FIG. 32C may be replaced with the plurality of transistors TP in FIG. 32A. For example, with the first and second modification examples combined, each of the plurality of transistors TP in FIG. 32B may be replaced with the plurality of transistors TP in FIG. 32A. For example, the resistance devices in two or more of the first to fourth modification examples may be arranged in series or in parallel.

Third Embodiment

A resistance device 100Q according to a third embodiment of the present invention will be described with reference to FIG. 33. The third embodiment is mainly different from the first and second embodiments in that the resistance device 100Q according to the third embodiment employs an NMOS transistor and a PMOS transistor, which differ in polarity from each other, as MOS resistance. Hereinafter, components of the third embodiment different from those of the first and second embodiments will be mainly described.

Figure 33:
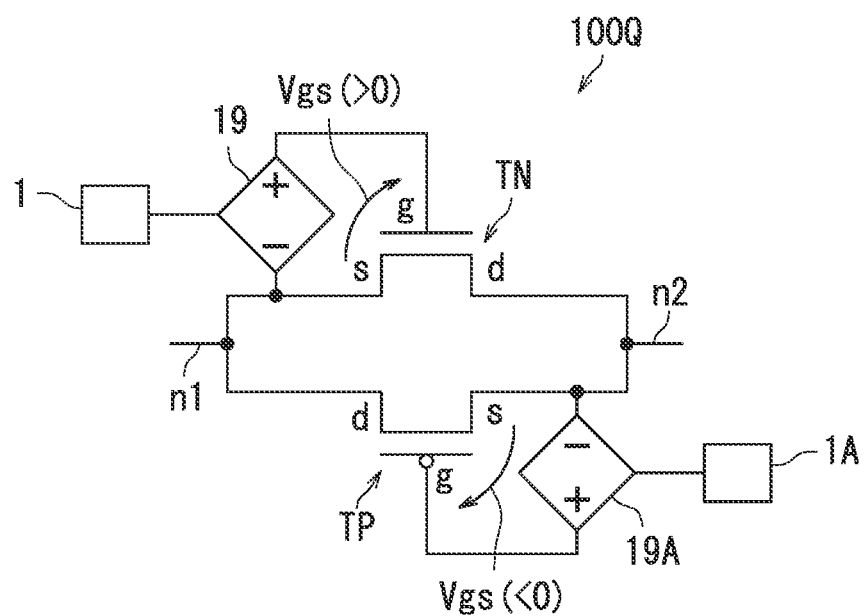
FIG. 33 is a diagram illustrating a resistance device according to a third embodiment of the present invention.

FIG. 33 is a diagram illustrating the resistance device 100Q according to the third embodiment. As illustrated in FIG. 33, the resistance device 100Q includes a voltage applying circuit 1, a voltage-controlled voltage source 19, an field-effect transistor TN, a voltage applying circuit 1A, a voltage-controlled voltage source 19A, and an field-effect transistor TN. The configurations of the voltage applying circuit 1, the voltage-controlled voltage source 19, and the field-effect transistor TN are the same as the configurations of the voltage applying circuit 1, the voltage-controlled voltage source 19, and the field-effect transistor TN described with reference to FIG. 1, respectively. The configurations of the voltage applying circuit 1A, the voltage-controlled voltage source 19A, and the field-effect transistor TP are the same as the configurations of the voltage applying circuit 1A, the voltage-controlled voltage source 19A, and the field-effect transistor TP described with reference to FIG. 25, respectively.

The voltage-controlled voltage source 19 is connected between the gate and source terminals of the transistor TN. The voltage-controlled voltage source 19A is connected between the gate and source terminals of the transistor TP.

The transistor TN and the transistor TP are connected in parallel between a node n1 and a node n2. Specifically, the source terminal of the transistor TN is connected to the node n1, and the drain terminal of the transistor TN is connected to the node n2. Further, the source terminal of the transistor TP is connected to the node n2, and the drain terminal of the transistor TP is connected to the node n1.

As described above with reference to FIG. 33, in the third embodiment, the transistor TP as PMOS resistance is connected in parallel with the transistor TN as NMOS resistance. Accordingly, the operating range of the resistance device 100Q is expanded, and the linearity of the resistance device 100Q can be further improved because the operating range of the transistor TP as the PMOS transistor is on the power supply voltage side, and the operating range of the transistor TN as the NMOS transistor is on the ground side. The operating range of the resistance device 100Q is the operating range of one MOS resistance element when the transistors TP and TN are regarded as one MOS resistance element. Similarly, the linearity of the resistance device 100Q is the linearity of the combined resistance of the transistors TP and TN when the transistors TP and TN are regarded as one MOS resistance element.

Modification Example

Modification examples according to the third embodiment will be described with reference to FIGS. 24A to 24D illustrating the first to fourth modification examples according to the first embodiment of the present invention, FIGS. 32A to 32D illustrating the first to fourth modification examples according to the second embodiment, and FIG. 33. In the third embodiment, the transistor TP and the transistor TN are connected in parallel and regarded as one MOS resistance element. That is, in FIG. 33, one MOS resistance element is composed of a single transistor TN and a single transistor TP. However, one MOS resistance element may be configured by combining a plurality of transistors TN and a plurality of transistors TP as illustrated in FIGS. 24A to 24D and 32A to 32D.

For example, the resistance device 100Q, instead of the voltage-controlled voltage source 19 and the transistor TN in FIG. 33, may include a voltage-controlled voltage source 19 and a plurality of transistor TNs of any of the first to fourth modification examples in FIGS. 24A to 24D, or may have a configuration in which two or more of the first to fourth modification examples in FIGS. 24A to 24D are combined. For example, the resistance device 100Q, instead of the voltage-controlled voltage source 19A and the transistor TP in FIG. 33, may include a voltage-controlled voltage source 19A and a plurality of transistors TP of any of the first to fourth modification examples in FIGS. 32A to 32D, or may have a configuration in which two or more of the first to fourth modification examples in FIGS. 32A to 32D are combined.

Fourth Embodiment

A brain-machine interface device BMI in the fourth embodiment of the present invention will be described with reference to FIGS. 34 and 35. The brain-machine interface device BMI in the fourth embodiment is provided with the resistance devices 100, 100A, 100B, 100C, 100D in the first embodiment (including the modification examples) and the resistance devices 100Z, 100E, 100F, 100G, 100H in the second embodiment (including the modification examples), or the resistance device 100Q in the third embodiment (including the modification examples). The brain-machine interface device BMI corresponds to an example of a "biological interface device". The biological interface device is a device that connects a biological body and a computer by detecting a biological signal or applying a stimulation signal to living tissue.

Figure 34:
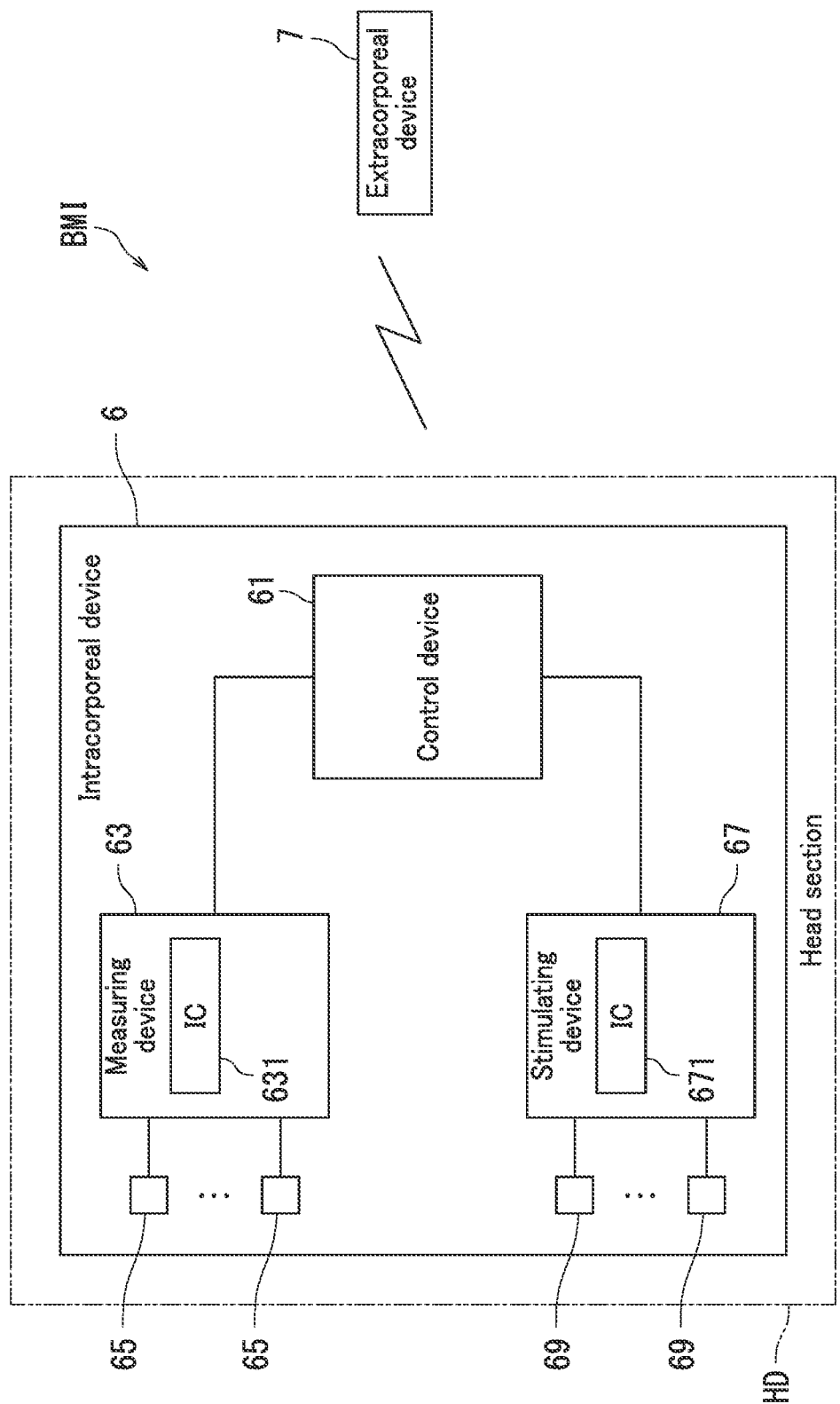
FIG. 34 is a diagram illustrating a brain-machine interface device in a fourth embodiment of the present invention.

FIG. 34 is a diagram illustrating the brain-machine interface device BMI in the fourth embodiment. As illustrated in FIG. 34, the brain-machine interface device BMI is a device that connects a brain and a computer by detecting an electrocorticogram or giving a stimulation signal to the brain.

The brain-machine interface device BMI includes an intracorporeal device 6 and an extracorporeal device 7. The intracorporeal device 6 is embedded in a head HD. The intracorporeal device 6 corresponds to an example of an "an implantable device that is allowed to be placed into a part of a body". The head HD corresponds to an example of "a part of a body". The intracorporeal device 6 detects an electrocorticogram and transmits brain information corresponding to the electrocorticogram to the extracorporeal device 7. Further, the intracorporeal device 6 gives a stimulation signal to the brain according to an instruction from the extracorporeal device 7. The extracorporeal device 7 performs an operation according to the brain information received from the intracorporeal device 6. The extracorporeal device 7 and the intracorporeal device 6 wirelessly communicate with each other.

The intracorporeal device 6 includes at least one of devices that include a measuring device 63 and a stimulating device 67. In the fourth embodiment, the intracorporeal device 6 includes the measuring device 63 and the stimulating device 67. The intracorporeal device 6 further includes a plurality of measurement electrodes 65, a plurality of stimulation electrodes 69, and a control device 61.

The control device 61 controls the measuring device 63 and the stimulating device 67. The control device 61 includes a communication device (not shown) that wirelessly communicates with the extracorporeal device 7. The control device 61 includes a processor such as a central processing unit (CPU) and storage such as semiconductor memory. For example, the control device 61 is a microcomputer.

The measuring device 63 measures an electrocorticogram via the plurality of measurement electrodes 65. Specifically, the plurality of measurement electrodes 65 are arranged at the brain, detects an electrocorticogram, and outputs the electrocorticogram to the measuring device 63. The measuring device 63 includes an integrated circuit (IC) device 631. The integrated circuit device 631 amplifies the electrocorticogram and outputs the amplified electrocorticogram to the control device 61. The control device 61 transmits brain information representing the electrocorticogram to the extracorporeal device 7. The measuring device 63 corresponds to an example of a "measuring device that is allowed to be placed into a part of a body to measure a biological signal". The electrocorticogram corresponds to an example of a "biological signal".

The stimulating device 67 gives a stimulating signal to the brain via the plurality of stimulation electrodes 69. Specifically, the stimulating device 67 generates a stimulation signal and outputs the stimulation signal to the plurality of stimulation electrodes 69. The plurality of stimulation electrodes 69 are arranged at the brain and gives a stimulation signal to the brain. The stimulating device 67 includes an integrated circuit (IC) device 671. The integrated circuit device 671 amplifies the stimulation signal while removing noise, and outputs the amplified stimulation signal to the plurality of stimulation electrodes 69. The stimulating device 67 corresponds to an example of a "stimulating device that is allowed to be placed into a part of a body to give a stimulation signal to living tissue". The brain corresponds to an example of "living tissue".

The field-effect transistors TN and the voltage applying circuits 1 of the resistance devices 100, 100A to 100D in the first embodiment (including the modification examples), the field-effect transistors TP and the voltage applying circuits 1A of the resistance devices 100Z, 100E to 100H in the second embodiment (including the modification examples), or the field-effect transistors TN and TP and the voltage applying circuits 1 and 1A of the resistance device 100Q in the third embodiment (including the modification examples) are integrated in each of the integrated circuit devices 631 and 671. In particular, the intracorporeal device 6 embedded in the head HD requires electrocorticograms from the plurality of measurement electrodes 65 and stimulation signals to the plurality of stimulation electrodes 69, and cannot increase the power supply voltage. Therefore, the integrated circuit of the resistance devices 100, 100A to 100H, 100Z, and 100Q is particularly effective.

Next, the reason why it is particularly effective to provide the integrated circuit devices 631 and 671 in the intracorporeal device 6 will be described. As an example, we focus on the measurement of electrocorticograms.

That is, in the measurement of the electrocorticograms, the measuring device 63 inputs, via the measurement electrodes 65, signals in each of which the electrocorticogram in the band of 1 Hz to several hundred Hz is imposed on the gradual fluctuation of the low frequency baseline level of 1 Hz or less. Generally, the electrocorticogram is at a level of several μV to several hundred μV. It is therefore required to amplify the electrocorticograms, for example, several hundred times to several thousand times in order to avoid being affected by extrinsic noise from the surrounding environment or intrinsic noise from the intracorporeal device 6.

On the other hand, the fluctuation of the baseline level is generally larger than the electrocorticogram. Therefore, if the signals acquired from the measurement electrodes 65 are simply amplified, the electrocorticograms cannot be acquired due to the excess of the input range of the measuring device 63. Therefore, a filter circuit for amplifying only the electrocorticograms in a desired frequency band from the signals from the measurement electrodes 65 is required. The filter circuit is mounted on the integrated circuit device 631.

An RC filter circuit 110X composed of a combination of a resistor R and a capacitance C as illustrated in FIG. 20, or an active filter circuit 110C as illustrated in FIG. 21 can be used as the above filter circuit. In this case, the cutoff frequency fc for band limiting is expressed as fc=1/(2π× RC). A configuration of the integrated circuit device 631 with a filter that cuts off a signal in the frequency band of 1 Hz or less requires the combination of a resistance R and a capacitance C that satisfies RC≥1/2π. It is however difficult to realize it in a realistic size with general high-resistance polysilicon and metal-insulator-metal (MIM) capacitance.

Therefore, MOS resistance using the transistors TN and TP of the resistance devices 100, 100A to 100H, 100Z, and 100Q according to the first to third embodiments is adopted as the resistance element constituting the filter circuit. It is accordingly possible to achieve a resistance value of 10 to $10^8$ times that of general high-resistance polysilicon with the same size as general high resistance polysilicon. The combination of the resistance R and the capacitance C satisfying RC≥1/(2π×1) becomes possible in a realistic size.

In addition, the temperature dependence of the resistance values R of the transistors TN and TP is reduced by integrating the resistance devices 100, 100A to 100H, 100Z, and 100Q according to the first to third embodiments in the integrated circuit device 631. As a result, the temperature dependence of the cutoff frequency fc is reduced. Thus, only the electrocorticograms in a desired frequency band can be amplified by integrating the filter circuit (for example, active filter circuit 110C of FIG. 21) including the transistors TN and/or TP in the first to third embodiments in the integrated circuit apparatus 631, suppressing the influence of temperature fluctuations on the head HD (brain) as much as possible, and accurately extracting only the electrocorticograms in the desired frequency band from the signals from the measurement electrodes 65. Similarly, it is effective to provide the integrated circuit device 671 in the intracorporeal device 6.

Figure 35:
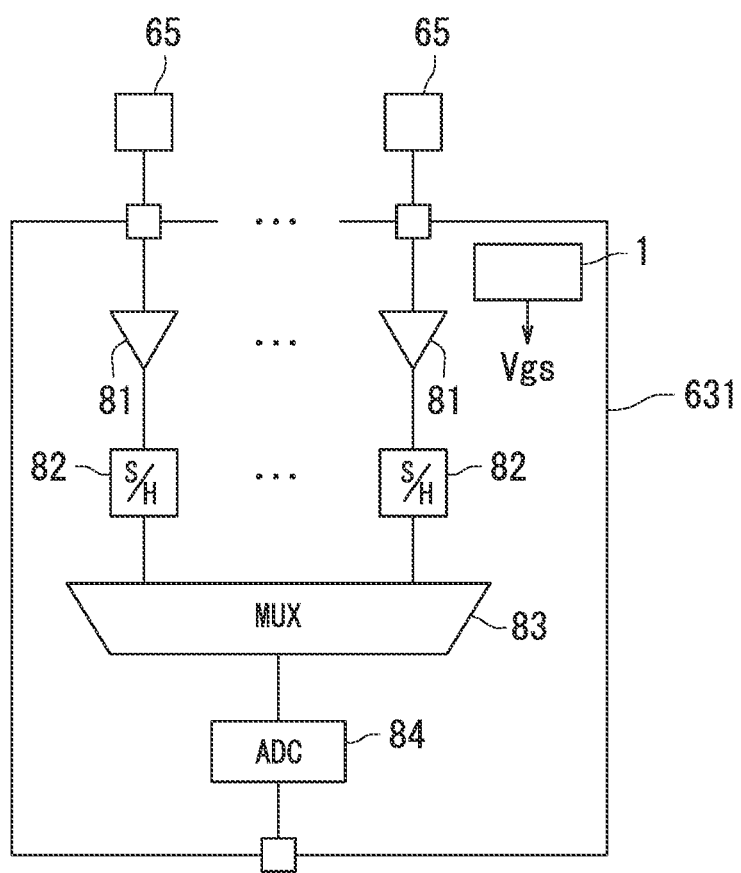
FIG. 35 is a circuit diagram illustrating an example of an integrated circuit device in the fourth embodiment.

FIG. 35 is a circuit diagram illustrating an example of the integrated circuit device 631. As illustrated in FIG. 35, the integrated circuit apparatus 631 includes a plurality of amplifiers 81, a plurality of sample hold circuits 82, a multiplexer 83, an analog-to-digital converter (ADC) 84, and the voltage applying circuit 1 in the first embodiment.

The plurality of amplifiers 81 receives the detection signals detected by the plurality of measurement electrodes 65, respectively. Each of the plurality of amplifiers 81 removes noise from the detection signal of a corresponding measurement electrode 65, extracts an electrocorticogram, amplifies the electrocorticogram, and outputs the amplified electrocorticogram to a corresponding sample hold circuit 82.

Specifically, each of the plurality of amplifiers 81 includes a filter circuit including the transistor TN as the MOS resistance in the first embodiment, for example, the active filter circuit 110C in FIG. 21. A voltage applying circuit 1 applies a control voltage Vgs between the gate and source of each transistor TN (MOS resistance MR) of the plurality of amplifiers 81. In this case, the voltage applying circuit 1 and the plurality of transistors TN form a resistance device 100. Note that the voltage-controlled voltage source 19 may be provided for each transistor TN. Further, for example, each of the plurality of amplifiers 81 may be configured by the RC filter circuit 110X in FIG. 20.

Note that each of the plurality of amplifiers 81 may include a filter circuit including a transistor TP as the MOS resistance in the second embodiment, or may include a filter circuit including transistors TN and TP as the MOS resistance in the third embodiment.

Each of the plurality of sample hold circuits 82 holds the electrocorticogram output from a corresponding amplifier 81, and outputs the held electrocorticogram to the multiplexer 83. The multiplexer 83 outputs a serial signal, in which the electrocorticograms output from the plurality of sample hold circuits 82 are multiplexed, to the ADC 84. The ADC 84 converts an analog serial signal into a digital signal and outputs the digital serial signal to the control device 61.

In the fourth embodiment, the brain-machine interface device BMI that measures and stimulates the brain of a living body has been described as one of application examples of the resistance devices 100, 100A to 100H, 100Z, and 100Q. However, the application of the resistance devices 100, 100A to 100H, 100Z, and 100Q can be applied to, for example a biological interface device, and is not limited to the brain-machine interface device BMI. Specifically, although the intracorporeal device 6 has been described in the fourth embodiment, the application of the resistance devices 100, 100A to 100H, 100Z, and 100Q is not limited to the intracorporeal device 6 embedded in the head HD. For example, it can be applied to an implantable device that is provided in the body of an animal such as a human being and that includes at least one of devices including a stimulating device that gives a stimulation signal to living tissue and a measuring device that measures a biological signal. Examples of the implantable device include a pacemaker or a cochlear implant.

The embodiments (including modification examples) of the present invention have been described above with reference to the drawings. However, the present invention is not limited to the above embodiments, and can be carried out in various embodiments without departing from the gist thereof. In addition, the plurality of components disclosed in the above embodiments can be appropriately modified. For example, a component of all the components in an embodiment may be added to another component of another embodiment. Alternatively, some of the components in an embodiment may be removed from the embodiment.

The drawings schematically illustrate respective components as a main body in order to make it easier to understand. The thickness, length, number, interval, etc. of each of the illustrated components may differ from the actual ones for the convenience of drawing. Further, each component illustrated in the above embodiments is an example and not particularly limited. Various modifications may be made without substantially deviating from the effects of the present invention.

INDUSTRIAL APPLICABILITY

The present invention provides a resistance device, an integrated circuit device, an implantable device, and a correction factor determining method, and has industrial applicability.

REFERENCE SIGNS LIST 1, 1A Voltage applying circuit
6 Intracorporeal device (Implantable device)
9, 9A Control voltage applying section
13, 13A Temperature detector
63 Measuring device
67 Stimulating device
100, 100A-100H, 100Q, 100Z Resistance device
131 First current source circuit
133 Second current source circuit
200, 200A, 200B Electronic circuit device (Integrated circuit device)
631, 671 Integrated circuit Device
TN, TP Field-effect transistor

The invention claimed is:

1. A resistance device comprising:
a field-effect transistor; and
a voltage applying circuit that applies a control voltage according to a temperature between a gate and a source of the field-effect transistor to control a resistance value between a drain and the source of the field-effect transistor, wherein
the control voltage is a voltage obtained by adding a correction voltage to a reference voltage, and
the correction voltage depends on the temperature and is set to be zero at a first temperature
the correction voltage being represented by $$Vc=\beta(T-T1),$$

where "Vc" represents the correction voltage, "β" represents a correction factor, "T" represents the temperature as a variable, and "T1" represents the first temperature.

2. The resistance device according to claim 1, wherein the voltage applying circuit includes:
a temperature detector that outputs a detection signal according to the temperature; and
a control voltage applying section that generates the control voltage so that the control voltage includes the correction voltage that varies linearly with respect to the temperature according to the detection signal and then applies the control voltage between the gate and the source of the field-effect transistor.

3. The resistance device according to claim 1, wherein the first temperature is a temperature when a physical quantity relating to the field-effect transistor is constant with respect to change in the correction factor that is a factor for determining the correction voltage.

4. The resistance device according to claim 1, wherein a value of the correction factor that is a value for determining the correction voltage is a value when a target physical quantity relating to the field-effect transistor is obtained at a second temperature different from the first temperature based on the reference voltage when the target physical quantity is obtained at the first temperature.

5. The resistance device according to claim 2, wherein the temperature detector includes:
a first current source circuit that generates a first current; and
a second current source circuit that generates a second current, wherein:
temperature dependence of the first current source circuit differs from temperature dependence of the second current source circuit;
the first current source circuit is connected in series to the second current source circuit;
a difference current between the first current and the second current is the detection signal;
the first temperature is varied by the first current source circuit varying a current value of the first current and/or the second current source circuit varying a current value of the second current.

6. The resistance device according to claim 1, wherein:
the voltage applying circuit applies the control voltage between the gate and the source of the field-effect transistor to control a resistance value between the drain and the source in a first operating region of the field-effect transistor; and
the first operating region is a region in which a magnitude of a voltage between the gate and the source of the field-effect transistor is larger than a magnitude of a threshold voltage.

7. The resistance device according to claim 1, wherein:
the voltage applying circuit applies the control voltage between the gate and the source of the field-effect transistor to control a resistance value between the drain and the source in a second operating region of the field-effect transistor; and
the second operating region is a region in which a magnitude of a voltage between the gate and the source of the field-effect transistor is smaller than a magnitude of a threshold voltage.

8. An integrated circuit device that integrates the field-effect transistor and the voltage applying circuit of the resistance device according to claim 1.

9. An implantable device that is allowed to be placed into a part of a body, the implantable device comprising at least one of devices that include a stimulating device that gives a stimulation signal to living tissue and a measuring device that measures a biological signal, wherein
the at least one of the devices includes the integrated circuit device according to claim 8.

10. A correction factor determining method that determines a correction factor for correcting a control voltage to be applied between a gate and a source of a field-effect transistor,
the correction factor determining method, in which the control voltage is represented by "Vgs" in an equation below $$Vgs=Vgs0+Vc=Vgs0+\beta(T-T1),$$

where "Vgs0" represents a reference voltage, "Vc" represents a correction voltage, "β" represents the correction factor, "T" represents a temperature as a variable, and "T1" represents a first temperature that is a temperature when the correction voltage Vc becomes zero, comprises:
determining a specific voltage value that is a voltage value of the reference voltage Vgs0 when a target physical quantity relating to the field-effect transistor is obtained at the first temperature T1; and
determining a specific factor value that is a value of the correction factor β when the target physical quantity is obtained at a second temperature different from the first temperature T1 and the specific voltage value of the reference voltage Vgs0.

11. The correction factor determining method according to claim 10, wherein
the determining a specific voltage value that is a voltage value of the reference voltage Vgs0 includes:
measuring a physical quantity relating to the field-effect transistor while varying a voltage value of the reference voltage Vgs0 at the first temperature T1; and defining, as the specific voltage value of the reference voltage Vgs0, the voltage value of the reference voltage Vgs0 when of a plurality of physical quantities measured while varying the voltage value of the reference voltage Vgs0, a physical quantity matching the target physical quantity is measured;

the determining a specific factor value that is a value of the correction factor β includes:

measuring a physical quantity relating to the field-effect transistor while varying a value of the correction factor B at the second temperature and the specific voltage value of the reference voltage Vgs0; and defining, as the specific factor value of the correction factor β, the value of the correction factor β when of a plurality of physical quantities measured while varying the value of the correction factor β, a physical quantity matching the target physical quantity is measured.

12. The correction factor determining method according to claim 10, wherein the first temperature T1 is a temperature when a physical quantity relating to the field-effect transistor is constant with respect to change in the correction factor β.

13. The correction factor determining method according to claim 10, wherein:

the correction voltage Vc has a value based on a difference current between a first current and a second current;

the first current is a current that varies linearly with respect to change in temperature;

the second current is a current that varies linearly with respect to the change in the temperature;

temperature dependence of the first current differs from temperature dependence of the second current; and the correction factor determining method further comprises varying the first temperature T1 by varying at least one of current values that include a current value of the first current and a current value of the second current.

14. The correction factor determining method according to claim 10, wherein the target physical quantity is a physical quantity containing a resistance value of the field-effect transistor, the physical quantity being measurable from an electronic circuit including the field-effect transistor, the target physical quantity being to be set as a target value.

* * * * *